(12) United States Patent
D'Souza et al.

(10) Patent No.: US 12,370,163 B2
(45) Date of Patent: *Jul. 29, 2025

(54) LEVODOPA DOSING REGIMEN

(71) Applicant: Amneal Pharmaceuticals, LLC, Bridgewater, NJ (US)

(72) Inventors: Richard D'Souza, Morristown, NJ (US); Hester Visser, Neshanic Station, NJ (US); Suneel Gupta, Hayward, CA (US)

(73) Assignee: Amneal Pharmaceuticals, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/022,531

(22) Filed: Jan. 15, 2025

(65) Prior Publication Data

US 2025/0152543 A1 May 15, 2025

Related U.S. Application Data

(63) Continuation of application No. 18/823,575, filed on Sep. 3, 2024, which is a continuation of application
(Continued)

(51) Int. Cl.
*A61K 9/20* (2006.01)
*A61K 9/50* (2006.01)
(Continued)

(52) U.S. Cl.
CPC .......... *A61K 31/198* (2013.01); *A61K 9/5005* (2013.01); *A61P 25/16* (2018.01)

(58) Field of Classification Search
None
See application file for complete search history.

(56) References Cited

U.S. PATENT DOCUMENTS 3,891,696 A    6/1975  Bodor et al.
4,021,555 A    5/1977  Seyfried et al.
(Continued)

FOREIGN PATENT DOCUMENTS

EP    0253490    1/1988
EP    0313845    5/1989
(Continued)

OTHER PUBLICATIONS

Nyholm, Dag, "Phamacotherapy for Parkinson's Disease—Observations and Innovations," Comprehensive Summaries of Uppsala Dissertations from the Faculty of Medicine 1236, May 2003.
(Continued)

*Primary Examiner* — Lakshmi S Channavajjala
(74) *Attorney, Agent, or Firm* — Florek & Endres PLLC

(57) ABSTRACT

The invention is a method for treating levodopa naïve patients with Parkinson's disease by orally administering a controlled release levodopa formulation twice a day to the levodopa naïve patient and the method provides an improvement of a patient's motor state as determined by patient's Parkinson's disease diary, provides a reduction of from about 10%-40% in the patient's tremor, dyskinesia, and/or mobility and/or provides a reduction in the patient's Movement Disorders Society version of the Unified Parkinson's Disease Rating Scale (MDS-UPDRS) scores by at least 3 points.

32 Claims, 21 Drawing Sheets

Related U.S. Application Data

No. 18/634,040, filed on Apr. 12, 2024, now Pat. No. 12,109,185, which is a continuation of application No. 17/967,332, filed on Oct. 17, 2022, now Pat. No. 11,986,449, which is a continuation-in-part of application No. 17/558,337, filed on Dec. 21, 2021, now Pat. No. 12,194,150.

(60) Provisional application No. 63/129,063, filed on Dec. 22, 2020, provisional application No. 63/150,121, filed on Feb. 17, 2021, provisional application No. 63/236,403, filed on Aug. 24, 2021, provisional application No. 63/247,639, filed on Sep. 23, 2021.

(51) Int. Cl.
*A61K 31/198* (2006.01)
*A61P 25/16* (2006.01)

(56) References Cited

U.S. PATENT DOCUMENTS

| | | |
|---|---|---|
| 4,160,020 A | 7/1979 | Ayer et al. |
| 4,367,217 A | 1/1983 | Gruber et al. |
| 4,424,235 A | 1/1984 | Sheth et al. |
| 4,427,648 A | 1/1984 | Brickl et al. |
| 4,438,091 A | 3/1984 | Grubet et al. |
| 4,826,875 A | 5/1989 | Chiesi |
| 4,839,177 A | 6/1989 | Colombo et al. |
| 4,849,227 A | 7/1989 | Cho |
| 4,855,326 A | 8/1989 | Fuisz |
| 4,900,755 A | 2/1990 | Dempski et al. |
| 4,938,968 A | 7/1990 | Mehta |
| 5,051,262 A | 9/1991 | Panoz et al. |
| 5,135,950 A | 8/1992 | Pippuri et al. |
| 5,188,840 A | 2/1993 | Iida et al. |
| 5,446,194 A | 8/1995 | Bäckström et al. |
| 5,532,274 A | 7/1996 | Wenzel et al. |
| 5,576,022 A | 11/1996 | Yang et al. |
| 5,594,030 A | 1/1997 | Conte et al. |
| 5,624,960 A | 4/1997 | Wenzel et al. |
| 5,637,320 A | 6/1997 | Bourke et al. |
| 5,650,169 A | 7/1997 | Conte et al. |
| 5,652,271 A | 7/1997 | Harris et al. |
| 5,681,583 A | 10/1997 | Conte et al. |
| 5,738,874 A | 4/1998 | Conte et al. |
| 5,773,031 A | 6/1998 | Shah et al. |
| 5,780,057 A | 7/1998 | Conte et al. |
| 5,840,756 A | 11/1998 | Cohen et al. |
| 5,945,424 A | 8/1999 | Schmidt |
| 6,024,981 A | 2/2000 | Khankari et al. |
| 6,027,748 A | 2/2000 | Conte et al. |
| 6,126,969 A | 10/2000 | Shah et al. |
| 6,183,778 B1 | 2/2001 | Conte et al. |
| 6,194,000 B1 | 2/2001 | Smith et al. |
| 6,221,392 B1 | 4/2001 | Khankari et al. |
| 6,238,699 B1 | 5/2001 | Rubin |
| 6,294,200 B1 | 9/2001 | Conte et al. |
| 6,309,666 B1 | 10/2001 | Hatano et al. |
| 6,372,252 B1 | 4/2002 | Blume et al. |
| 6,372,254 B1 | 4/2002 | Ting et al. |
| 6,376,545 B1 | 4/2002 | Levin |
| 6,500,867 B1 | 12/2002 | Virkki et al. |
| 6,531,153 B2 | 3/2003 | Seth |
| 6,602,521 B1 | 8/2003 | Ting et al. |
| 6,627,223 B2 | 9/2003 | Percel et al. |
| 6,630,162 B1 | 10/2003 | Nilvebrant et al. |
| 6,723,348 B2 | 4/2004 | Faham et al. |
| 6,730,321 B2 | 5/2004 | Ting et al. |
| 6,733,781 B2 | 5/2004 | Abu-Izza et al. |
| 6,793,936 B2 | 9/2004 | Devane et al. |
| 6,797,732 B2 | 9/2004 | Virkki et al. |
| 6,811,794 B2 | 11/2004 | Burnside et al. |
| 7,048,945 B2 | 5/2006 | Percel et al. |
| 7,094,427 B2 | 8/2006 | Han et al. |
| 8,377,474 B2 | 2/2013 | Hsu et al. |
| 8,591,913 B2 | 11/2013 | Miyazaki et al. |
| 10,098,845 B2 | 10/2018 | Hsu et al. |
| 10,292,935 B2 | 5/2019 | Hsu et al. |
| 10,688,058 B2 | 6/2020 | Hsu et al. |
| 10,973,769 B2 | 4/2021 | Hsu et al. |
| 10,987,313 B2 | 4/2021 | Hsu et al. |
| 11,357,733 B2 | 6/2022 | Hsu et al. |
| 11,622,941 B2 | 4/2023 | Hsu et al. |
| 11,666,538 B2 | 6/2023 | Hsu et al. |
| 2002/0155154 A1 | 10/2002 | Wong et al. |
| 2003/0147957 A1 | 8/2003 | Licht et al. |
| 2003/0152628 A1 | 8/2003 | Licht et al. |
| 2003/0224045 A1 | 12/2003 | Han et al. |
| 2004/0028613 A1 | 2/2004 | Quay |
| 2004/0166159 A1 | 8/2004 | Han et al. |
| 2005/0070608 A1 | 3/2005 | Remenar et al. |
| 2005/0147670 A1 | 7/2005 | Hsu et al. |
| 2005/0203185 A1 | 9/2005 | Remenar et al. |
| 2006/0013875 A1 | 1/2006 | Han et al. |
| 2006/0018965 A1 | 1/2006 | Moodley et al. |
| 2006/0045865 A1 | 3/2006 | Jacob et al. |
| 2006/0057197 A1 | 3/2006 | Han et al. |
| 2007/0003621 A1 | 1/2007 | Nangia et al. |
| 2007/0082048 A1 | 4/2007 | Warner |
| 2007/0148238 A1 | 6/2007 | Nangia et al. |
| 2007/0190145 A1 | 8/2007 | Venkatesh et al. |
| 2007/0275060 A1 | 11/2007 | Befumo et al. |
| 2008/0131492 A1 | 6/2008 | Nangia et al. |
| 2008/0299204 A1 | 12/2008 | Nangia et al. |
| 2009/0004229 A1 | 1/2009 | Pastini et al. |
| 2009/0220611 A1 | 9/2009 | Dargelas et al. |
| 2010/0298268 A1 | 11/2010 | Hsu et al. |
| 2010/0331244 A1 | 12/2010 | Miyazaki |
| 2011/0111024 A1 | 5/2011 | Mao et al. |
| 2012/0177731 A1 | 7/2012 | Hsu et al. |
| 2013/0195973 A1 | 8/2013 | Gupta et al. |
| 2016/0250170 A1 | 9/2016 | Hsu et al. |
| 2016/0287523 A1 | 10/2016 | Hsu et al. |
| 2019/0254978 A1 | 8/2019 | Hsu et al. |
| 2020/0009062 A1 | 1/2020 | Hsu et al. |
| 2020/0253881 A1 | 8/2020 | Hsu et al. |
| 2021/0128480 A1 | 5/2021 | Hsu et al. |
| 2021/0338591 A1 | 11/2021 | Hsu et al. |
| 2023/0301923 A1 | 9/2023 | Hsu et al. |

FOREIGN PATENT DOCUMENTS

| | | |
|---|---|---|
| EP | 0320051 | 6/1989 |
| EP | 0393572 | 10/1990 |
| EP | 1262198 | 12/2002 |
| EP | 1964566 | 9/2008 |
| EP | 2508174 | 10/2012 |
| WO | 1995001781 | 1/1995 |
| WO | 1999004765 | 2/1999 |
| WO | 199917745 | 4/1999 |
| WO | 1999017745 | 4/1999 |
| WO | 1999051209 | 10/1999 |
| WO | 2000015197 | 3/2000 |
| WO | 2000018447 | 4/2000 |
| WO | 2002000213 | 1/2002 |
| WO | 2003000018 | 1/2003 |
| WO | 2003005967 | 1/2003 |
| WO | 2003101432 | 12/2003 |
| WO | 2004062577 | 7/2004 |
| WO | 2005023185 | 3/2005 |
| WO | 2005099678 | 10/2005 |
| WO | 2006026556 | 3/2006 |
| WO | 2007002516 | 1/2007 |
| WO | 2007002518 | 1/2007 |
| WO | 2007022956 | 3/2007 |
| WO | 2007090091 | 8/2007 |
| WO | 2009085306 | 7/2009 |
| WO | 2010134074 | 11/2010 |
| WO | 2010140531 | 12/2010 |

(56) References Cited

FOREIGN PATENT DOCUMENTS

| WO | 2012136819 | 10/2012 |
|---|---|---|
| WO | 2015054302 | 4/2015 |

OTHER PUBLICATIONS

Lewitt, Peter et al., "New Developments in Levodopa Therapy," Neurology, 62(1 suppl. 1):S9-S16, Jan. 2004.
Han, Chien-Hsuan, Declaration Under 37 C.F.R. §1.132, Oct. 14, 2004.
Hiroshi, et al., "The Effect of Ascorbic Acid on the Pharmacokinetics of Levodopa in Elderly Patients with Parkinson's Disease," Clinical Neuropharmacology, Nov. 2004, 27:270-3.
Fincher, "Particle Size of Drugs and its Relationship to Absorption and Activity," Journal of Pharmaceutical Sciences, 1968, 57:1825-35.
Actavis Laboratories FL, Inc., Notification of Certification for U.S. Pat. Nos. 9,089,607 and 9,089,608 Pursuant to § 505(j)(2)(B)(ii) of the Federal Food, Drug, and Cosmetic Act, Aug. 13, 2015.
Actavis Laboratories FL, Inc., Notification of Certification for U.S. Pat. Nos. 8,377,474; 8,557,283; 8,454,998; and 7,094,427 Pursuant to § 505(j)(2)(B)(ii) of the Federal Food, Drug, and Cosmetic Act, Aug. 4, 2015.
Impax Laboratories, Inc., Complaint against Actavis Laboratories FL, Inc. and Actavis Pharma Inc., Action for Patent Infringement under the Food and Drug Laws and Patent Laws of the United States, Sep. 17, 2015.
Mark, et al., "Controlled-Release Carbidopa-Levodopa (Sinemet) in Combination with Standard Sinimet in Advanced Parkinson's Disease," 19 Annals Clinical Laboratory Sci. vol. 19, No. 2, 101-106(1989).
Hoffman, et al., "Pharmacokinetic and Pharmacodynamic Aspects of Gastroretentive Dosage Forms," Intl. J. of Pharmaceutics, 227, 141-153. (2004).
Yeh, et al., "Pharmacokinetics and Bioavailability of Sinimet CR; A Summary of Human Studies," Neurology vol. 39, 25-38 (Supp. 2 1989).
Cedarbaum, et al., "A Pharmacokinetic and Pharmacodynamic Comparison of Sinemet CR (50/200) and Standard Sinimet (25/100)," 39 Neurology 38-44 (Supp. 2 1989).
Grahnen, et al., "Comparative Multiple-Dose Pharmacokinetics of Controlled-Release Levodopa Products," 32 European Neurology 343-348 (1992).
Young, Rosabel, "Update on Parkinson's Disease," 59 American Family Physician vol. 59, 2155-2167 (1999).
Sasahara, et al., "Dosage Form Design for Improvement of Bioavailability of Levodopa II: Bioavailability of Marketed Levodopa Preparations in Dogs and Parkinsonian Patients," Journal of Pharmaceutical Sciences, 69(3), 261-265 (1980).
Klausner, et al., "Novel Levodopa Gastroretentive Dosage Form: In-Vivo Evaluation in Dogs," J. Controlled Release, 88, 117-126 (2003).
Klausner, et al., "Novel Gastroretentive Dosage Form: Evaluation of Gastroretentivity and its Effect on Levodopa Absorption in Humans," Pharm. Res., 20(9), 1466-1473 (2003).
Sandoz Notification pursuant to Section 505 (j) (2) (B) (iv) of the Federal Food Drug and Cosmetic Act, Feb. 14, 2017.
Akhgari et al. "Statistical Optimization of Indomethacin Pellets Coated with pH-Dependent Methacrylic Polymers for Possible Colonic Drug Delivery." International Journal of Pharmaceutics, 305:22-30 (2005).
Badawy, et al., "Microenvironmental pH Modulation in Solid Dosage Forms." Journal of Pharmaceutical Sciences, vol. 96, No. 5, 948-59 (2007).
Bredenberg et al., "An Automatic Dose Dispenser for Microtablets—A New Concept for Individual Dosage of Drugs in Tablet Form." International Journal Pharmaceutics, 261:137-146 (2003).
Cedarbaum, "Clinical Pharmacokinetics of Anti-Parkinsonian Drugs." Clinical Pharmacokinetics, 13(3): 141-178 (1987).
Cedarbaum, "The Promise and Limitations of Controlled-Release Oral Levodopa Administration." Clinical Neuropharmacology, 12(3): 147-166 (1989).
Chourasia, et al. "Pharmaceutical Approaches to Colon Targeted Drug Delivery Systems." Journal of Pharmacy and Pharmaceutical Sciences, 6(1); 33-66 (2003).
Cole et al., "Enteric Coated HPMC Capsules Designed to Achieve Intestinal Targeting." International Journal Pharmaceutics, 231(1): 83-95 (2002).
Contin et al., "Pharmacokinetic Optimisation in the Treatment of Parkinson's Disease." Clinical Pharmacokinetics, Jun. 30(6): 463-481 (1996).
Crevoisier et al., "Bioavailability of L-Dopa after Madopar HBS Administration in Healthy Volunteers." European Neurology, 27 (Suppl. 1): 36-46 (1987).
Crevoisier et al., "Comparative Single- and Multiple-Dose Pharmacokinetics of Levodopa and 3-O-Methyldopa Following a New Dual-Release and a Conventional Slow-Release Formulation of Levodopa and Benserazide in Healthy Volunteers." European Neurology, 49(1): 39-44 (2003).
Dave et al., "Expression of Heteromeric Amino Acid Transporters along the Murine Intestine." J Physiol 558.2, 597-610 (2004).
Dingemanse, et al. "Pharmacokinetic Studies with a Dual-Release Formulation of Levodopa, a Novel Principle in the Treatment of Parkinson's Disease." European Neurology, 39(2): 119-124 (1998).
Espinoza et al., "Influence of Admixed Citric Acid on the Release Profile of Pelanserin Hydrochloride from HPMC Matrix Tablets." International Journal Pharmaceutics, 201(2): 165-173 (2000).
Gomes, et al., "Na+ Independent Transporters, LAT-2 and B0,+, Exchange L-DOPA with Neutral and Basic Amino Acids in Two Clonal Renal Cell Lines." Journal Membrane Biology, 186(2): 63-80 (2002).
Gomes, et al., "L-DOPA Transport Properties in an Immortalised Cell Line of Rat Capillary Cerebral Endothelial Cells, RBE 4." Brain Research, 829 (1-2): 143-150 (1999).
Goole et al., "Developmental and Evaluation of New Multiple-Unit Levodopa Sustained-Release Floating Dosage Forms." International Journal of Pharmaceutics, 334(1-2): 35-41 (2007).
Goole et al., "Evaluation and Floating Enhancement of Levodopa Sustained Release Floating Minitablets Coated with Insoluble Acrylic Polymer." Drug Development and Industrial Pharmacy, 34(8): 827-833 (2008).
Guthmann et al., "Development of A Multiple Unit Pellet Formulation for a Weakly Basic Drug." Drug Development and Industrial Pharmacy, 33(3): 341-349 (2007).
Horter, et al., "Influence of Physicochemical Properties on Dissolution of Drugs in the Gastrointestinal Tract." Advance Drug Delivery Reviews, 46(1-3): 75-87 (2001).
Iida, et al., "Improvement of Intestinal Absorption of P-glycoprotein Substrate by D-Tartaric Acid." Drug Metabolism and Pharmacokinetics, 21(5): 424-428 (2006).
Jenner, "Avoidance of Dyskinesia: Preclinical Evidence for Continuous Dopaminergic Stimulation." Neurology, 62 (Suppl. 1): S47-55 (2004).
Kendall, et al., "The Role of Polymers in Solid Oral Dosage Forms." Polymers in Drug Delivery, 35-48 (Ijeoma F. Uchebbo and Andres G. Schatzlein eds., 2006).
Khor, et al., "The Pharmacokinetics and Pharmacodynamics of Levodopa in the Treatment of Parkinson's Disease." Current Clinical Pharmacology, 2(3): 234-243 (2007).
Knop, et al., "Pharmaceutical Pellets." ExAct, No. 15 (Nov. 2005).
Kranz, et al., "Development of a Single Unit Extended Release Formulation for Zk 811 752, a Weakly Basic Drug." European Journal of Pharmaceutics Sciences, 26(1): 47-53 (2005).
Lees, "The On-Off Phenomenon." Journal of Neurology, Neurosurgery, and Psychiatry, Special Supplement 29-37 (1989).
Lewitt, "Clinical Studies with and Pharmacokinetic Considerations of Sustained-Release Levodopa." Neurology, 42 (Suppl. 1): 29-32 (1992).
Lewitt, "Levodopa Therapeutics: New Treatment Strategies." Neurology, 43 (Suppl. 6): S31-37 (1993).

(56) References Cited

OTHER PUBLICATIONS

Li et al., "Enteric-Coated Layered Double Hydroxides as a Controlled Release Drug Delivery System." International Journal of Pharmaceutics, 287(1-2): 89-95 (2004).
Lorenzo-Lamosa et al., "Design of Microencapsulated Chitosan Microspheres for Colonic Drug Delivery." Journal of Control Release, 52 (1-2): 109-118 (1998).
Macmahon et al., "A Comparison of the Effects of Controlled-Release Levodopa (Madopar CR) with Conventional Levodopa in late Parkinson's Disease." Journal of Neurology, Neurosurgery, and Psychiatry, 53(3): 220-223 (1990).
Malcom et al., "Single-Dose Pharmacokinetics of Madopar HBS in Patients and Effect of Food and Antacid on the Absorption of Madopar HBS in Volunteers," European Neology, 27 (Suppl. 1): 28-35 (1987).
FDA Bioequivalence Review for ANDA 75-091 (1998).
Nyholm, et al., "Levodopa Infusion Therapy in Parkinson Disease: State of the Art in 2004." Clinical Neuropharmacology, 27(5): 245-256 (2004).
Nyholm, "Pharmacokinetic Optimisation in the Treatment of Parkinson's Disease: An Update." Clinical Pharmacokinetics, 45(2): 109-136 (2006).
Nyholm et al., "Optimizing Levodopa Pharmacokinetics: Intestinal Infusion Versus Oral Sustained-Release Tablets." Clinical Neuropharmacology, 26(3): 156-163 (2003).
Nykanen et al., "Citric Acid as Excipient in Multiple Unit Enteric-Coated Tablets for Targeting Drugs on the Colon." International Journal Pharmaceuticas, 229(1-2): 155-162 (2001).
Ogawa, "Factors Affecting Levodopa Effects in Parkinson's Disease." Acta Med Okayama, 54(3): 95-101 (2000).
Pinho et al., "Over Expression of Renal LAT1 and LAT2 and Enhanced LDOPA Update in SHR Immortalized Renal Proximal Tubular Cells." Kidney International, 66(1): 216-226 (2004).
Poewe et al., "Treatment of Motor Fluctuations in Parkinson's Disease with an Oral Sustained-Release Preparation of L-Dopa: Clinical and Pharmacokinetic Observations." Clinical Neuropharmacology, 9(5): 430-439 (1986).
Quinones et al., "The Dopamine Precursor L-Dihydroxyphenylalanine is Transported by the Amino Acid Transporters rBAT and LAT2 in Renal Cortex." American Journal of Physiology Renal Physiology, 287(1): F74-80 (2004).
Rao et al., "Parkinson's Disease: Diagnosis and Treatment." American Family Physician, 74(12): 2047-2054 (2006).
Scattergood et al., "Comparative Study of Theoretical Versus Actual Weight Gain for a Surelease® Barrier Membrane on Coated Pellets." www.colorcon.com, mr/poster/SureSpheres/stud_comp_wt_gain_REV/Rev1.2009 (2004).
Seipe et al., "Strategies for the Design of Hydrophilic Matrix Tablets with Controlled Microenvironmental pH." International Journal of Pharmaceutics, 316 (1-2): 14-20 (2006).
Simon et al., "The Effects of a Normal Protein Diet on Levodopa Plasma Kinetics in Advanced Parkinson's Disease." Parkinsonism Related Disorders, 10(3): 137-142 (2004).
Sinemet® Package Insert, 2002.
Tang et al., "Coating of Multiparticulates for Sustained Release." American Journal of Drug Delivery, 3(1): 17-28 (2005).
"Treatment of Early Parkinson's Disease." American Family Physician, 72(3): 497-500 (2005), http://aafp.org/afp/2005/0801/p497.html.
HSU Declaration, Under 37 C.F.R. 1.132 (Sep. 24, 2012).
Bettini et al. "Influence of Layer Position on In Vitro and In Vivo Release of Levodopa Methyl Ester and Carbidopa from Three-Layer Matrix Tablets," European Journal of Pharmaceutics and Biopharmaceutics, 53:227-232 (2002).
Deleu, et al., "Clinical and Pharmacokinetic Comparison of Oral and Dodental Delivery of Levodopa/Carbidopa in Patients with Parkinson's Disease with a Fluctuating Response to Levodopa," European Journal of Clinical Pharmacology, 41:453-458 (1991).

Pahwa et al., "Early Morning Akinesia in Parkinson's Disease: Effect of Standard Carbidopa/Levodopa and Sustained-Release Carbidopa/Levodopa," Neurology, 46: 1059-1062 (1996).
Pahwa et al., "Comparison of Standard Carbidopa-Levodopa and Sustained-Release Carbidopa-Levodopa in Parkinson's Disease: Pharmacokinetic and Quality of Life Measures," Movement Disorders, 12:677-681 (1997).
Kurlan et al., "Duodenal and Gastric Delivery of Levodopa in Parkinsonism," Annals of Neurology, 23:589-595 (1988).
Kurlan et al., "Erratic Gastic Emptying of Lvodopa May Cause Random Fluctuations of Parkinsonian Mobility," Neurology, 38:419-421 (1988).
Baruzzi et al., "Influence of Meal Ingestion Time on Pharmacokinetics of Orally Administered Levodopa in Parkinsonian Patients," Clinical Neuropharmacolgy, 10:527-537 (1987).
Sinemet® CR Package Insert, Jan. 2011.
Rytary® Package Insert, Jan. 2015.
Stalevo® Package Insert, Sep. 2010.
FDA Draft Guidance for Carbidopa Levodopa Extended Release Capsule Sep. 2015.
Yao, et al. "Clinical Pharmacokinetics of IPX066: Evaluation of Dose Proportionality and Effect of Food in Healthy Volunteers," Clinical Neuropharmacol., 29:10-17 (2016).
Hsu, et al., "Comparison of the Pharmacokinetics of an Oral Extended-Release Capsule Formulation of Carbidopa-Levodopa (IPX066) with Immediate-Release Carbidopa-Levodopa (Sinemet®), Sustained-Release Carbidopa-Levodopa (Sinemet® CR), and Carbidopa-Levodopa-Entacapone (Stalevo®)" J. Clinical Pharmacology 55 (9):995-1001 (2015).
Brooks, "Optimizing Levodopa Therapy for Parkinson's Disease with Levodopa/Carbidopa/Entacapone: Implications from a Clinical and Patient Perspective," Neuropsychiatr Dis Treat 4:39-47 (2008).
Chana, et al., "Delayed Early Morning Turn "ON" in Response to a Single Dose of Levodopa in Advanced Parkinson's Disease: Pharmacokinetics Should be Considered," J. Neurol Neurosurg Psychiaty 75:1782-1783 (2004).
Hauser, "Levodopa: Past, Present, and Future," Eur. Neurol. 62:1-8 (2009).
Kempster et al., "Levodopa Peripheral Pharmacokinetics and Duration of Motor Response in Parkinson's Disease," J. Neurol Neurosurg Psychiatry, 52:718-723 (1989).
Mao et al., "Population Pharmacodynamics of IPX066: An Oral Extended-Release Capsule Formulation of Carbidopa-Levodopa, and Immediate-Release Carbidopa-Levodopa in Patients with Advanced Parkinson's Disease," J. Clin. Pharm. 53:523-531 (2013).
Fahn, "Parkinson Disease, the Effect of Levodopa and the ELLDOPA Trial, Earlier vs Later L-DOPA," Arch Neurol. 56 (5):529-535 (1999).
Stocchi, et al., "Intermittent vs Continuous Levodopa Administration in Patients with Advanced Parkinson Disease: a Clinical and Pharmacokinetic Study," Arch Neurol. 62(6):905-910 (2005).
Goetz, et al., "Handling Missing Values in the NDS-UPDRS," Mov. Disord. 30(12):1632-1638 (2015).
Modi, et al., "Single-Dose Pharmacokinetics and Pharmacodynamics of IPX203 in Patients With Advanced Parkinson Disease: A Comparison with Immediate-Release Carbidopa-Levodopa and with Extended-Release Carbidopa-Levodopa Capsules," Clinical Neuropharmacology 42(1):4-8 (2019).
Chen, et al., "Pharmacokinetics and Pharmacodynamics of Gastroretentive Delivery of Levodopa/Carbidopa in Patients with Parkinson Disease," Clin Neuropharmacol 35:67-72 (2012).
Hauser, et al., "Crossover Comparison of IPX066 and a Standard Levodopa Formulation in Advanced Parkinson's Disease," Mov. Disord, 26:2246-2252 (2011).
Stacy et al., "Motor Effects and Safety of IPX203, an Investigational Extended-Release Formulation of Carbidopa-Levodopa, in Advanced Parkinson's Disease: A Single-Dose Phase 2 Study," Aug. 21, 2017.
Stacy et al., "Motor Effects and Safety of IPX203, an Investigational Extended-Release Formulation of Carbidopa-Levodopa, in Advanced Parkinson's Disease: A Single-Dose Phase 2 Study," Neurology, 2017; 89, e99 (2017 Emerging Science Abstracts), Aug. 21, 2017.

(56) References Cited

OTHER PUBLICATIONS

Impax Laboratories, "Impax Laboratories (IPXL) to Present Data on Neurology Development Programs at AAN" StreetInsider.com, Apr. 21, 2017.

Pena, "IPX203 Extended-Release Capsules Reduce 'Off' Time In Advanced Parkinson's," parkinsonsnewtoday.com/2019/07/18/ipx203-extended-release-capsules-reuced-off-time-advanced-parkinsons/ Jul. 18, 2019.

Modi et al., "Pharmacodynamics, Efficacy, and Safety of IPX203 in Parkinson Disease Patients With Motor Fluctuations," Clinical Neuropharmacology, 42(5) pp. 149-156 Sep. 2019 (published on line Jul. 12, 2019).

Mittur et al., "Multiple-Dose Pharmacodynamics of IPX203," Annals of Neurology, vol. 84 (suppl 22) 2018, S324LBA (abstract presented during the 143 rd Annual Meeting of American Neurological Association Oct. 21-23, 2018 Atlanta, GA) Oct. 5, 2018.

Impax Laboratories, LLC, "An Randomized Controlled Study to Compare the Safety and Efficacy of IPX203 with Immediate-Release Carbidopa-Levodopa in Parkinson's Disease Patients with Motor Fluctuations," Clinicaltrialsregister.eu, EudraCT No. 2018-002233-37 (UK) Feb. 14, 2019 6 pages.

Impax Laboratories, LLC, "An Randomized Controlled Study to Compare the Safety and Efficacy of IPX203 with Immediate-Release Carbidopa-Levodopa in Parkinson's Disease Patients with Motor Fluctuations," Clinicaltrialsregister.eu, EudraCT No. 2018-002233-37 (Germany) Jan. 8, 2018 6 pages.

Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Spain) Jun. 11, 2019 8 pages.

Decision in Opposition Proceedings for European Patent No. 3 054 929 dated Nov. 18, 2022.

Notice of Opposition to Columbian Patent Application No. NC20230009085 dated Nov. 29, 2023.

Mao et al., "Dose-Response Analysis of the Effect of Carbidopa-Levodopa Extended-Release Capsules (IPX066) in Levodopa-Naïve Patients with Parkinson Disease," J. Clin. Pharm. 2016; 56: 974-82.

Clinical Trial NCT00880620, "A Study to Evaluate the Safety and Efficacy of IPX066 in Subjects With Parkinson's Disease" Oct. 25, 2019.

LeWitt et al., et al., "Pharmacokinetic-Pharmacodynamic Crossover Comparison of Two Levodopa Extension Strategies," Mov. Disord. 2009; 24: 1319-24 (LeWitt).

Nyholm, et al., "Frequent Administration of Levodopa/Carbidopa Microtablets vs. Levodopa/Carbidopa/Entacapone in Healthy Volunteers," Acta Neurol. Scand. 2013: 127:124-32.

Waters et al.,"Long-Term Treatment With Extended-Release Carbidopa-Levodopa (IPX066) in Early and Advanced Parkinson's Disease: a 9-Month Open-Label Extension Trial," CNS drugs. Apr. 2015;29:341-50.

Pahwa et al., "Randomized Trial of IPX066, Carbidopa/Levodopa Extended Release, in Early Parkinson's Disease," Parkinsonism & Related Disorders. Feb. 1, 2014;20(2):142-8.

Hauser et al., "Extended-Release Carbidopa-Levodopa (IPX066) Compared with Immediate-Release Carbidopa-Levodopa in Patients with Parkinson's Disease and Motor Fluctuations: a Phase 3 Randomised, Double-Blind Trial," The Lancet Neurology. Apr. 1, 2013;12(4):346-56.

Espay et al., "Optimizing Extended-Release Carbidopa/Levodopa in Parkinson Disease: Consensus on Conversion From Standard Therapy," Neurology: Clinical Practice. Feb. 2017;7(1):86-93.

European Patent Application Publication No. 4267113 (application No. 21912079.7) Supplemental Search Report Oct. 23, 2024.

Obenewaa et al., "Chitosan-Coated Hydroxypropylmethyl Cellulose Microparticles of Levodopa (and Carbidopa): In Vitro and Rat Model Kinetic Characteristics," Current Therapeutic Research, Excerpta Medica, vol. 93, Jan. 1, 2020.

Impax Laboratories, LLC, "A Study to Assess the PK and Pharmacodynamics of IPX203 in Patients With Advanced Parkinson's Disease," ClinicalTrials.gov archive (identifier NCT02271530), Oct. 22, 2014, 9 pages.

Impax Laboratories, LLC, "A Study to Evaluate the Safety and Efficacy of IPX203 in Parkinson's Disease Patients With Motor Fluctuations," ClinicalTrials.gov archive (identifier NCT03670953), Sep. 14, 2018, 7 pages.

Impax Laboratories, LLC, "Open Label Extension (OLE) Study of the Safety and Clinical Utility of IPX203 in PD Patients With Motor Fluctuations," ClinicalTrials.gov archive (identifier NCT03877510), Mar. 15, 2019, 14 pages.

Impax Laboratories, LLC, "A Study to Assess the PK and Pharmacodynamics of IPX203 in Subjects With Advanced Parkinson's Disease," ClinicalTrials.gov archive (identifier NCT03007888) Jan. 2, 2017, 7 pages.

Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Germany) May 16, 2019 8 pages.

Impax Laboratories, LLC, "An Open-Label Extension Study of the Safety and Clinical Utility of IPX203 in Parkinson's Disease Patients with Motor Fluctuations," Clinicaltrialsregister.eu, EudraCT No. 2018-002234-21 (Czech Republic) May 30, 2019 8 pages.

Stacy et al., "Motor Effects and Safety of IPX203, an Investigational Extended-Release Formulation of Carbidopa-Levodopa, in Advanced Parkinson's Disease: A Single Dose Study," Poster presented at the American Academy of Neurology (AAN) Annual Meeting, Boston, MA Apr. 22-28, 2017 (Pos 005).

Stacy et al., "Motor Effects and Safety of IPX203, an Investigational Extended-Release Formulation of Carbidopa-Levodopa, in Advanced Parkinson's Disease: A Single Dose Study," Poster presented at the 21st International Congress of Parkinson's Disease and Movement Disorders, Vancouver, BC, Canada, Jun. 4-7, 2017 (Pos1412).

Mittur et al., "Multiple-Dose Pharmacodynamics of IPX203: A New Investigational Oral Extended-Release Formulation of Carbidopa-Levodopa, in Patients with Advanced Parkinson's Disease," Poster presented at the Annual Meeting of the American Neurological Association, Atlanta, GA, Oct. 21-23, 2018.

Opposition submission against European Patent No. 2 234 963 filed by Dr. Luigi Rumi, Jan. 7, 2021.

Hayashi et al., "Physiological Mechanism for Enhancement of Paracellular Drug Transport," Journal of Controlled Release 62 (1999) pp. 141-148.

Nagayama et al., "Effect of Ascorbic Acid on the Pharmacokinetics of Levodopa in Elderly Patients with Parkinson Disease," Clin. Neuropharmacol., vol. 27, No. 6, Nov.-Dec. 2004, pp. 270-273.

Opposition submission against European Patent No. 2 234 963 filed by Teva Pharmaceutical industries, Limited, Jan. 7, 2021.

Carbidopa and Levodopa Tablet, extended release, Package Insert, Mylan Pharmaceuticals Inc., Feb. 2020 revision (original publication 1999).

LeWitt et al., "Controlled-Release Carbidopa/Levodopa (Sinemet 50/200 CR4) Clinical and Pharmacokinetic Studies," Neurology 1989; 39 (Suppl. 2); pp. 45-53.

Response to Oppositions of European Patent No. 2 234 967 filed by Impax Laboratories LLC Jun. 8, 2021.

Goodman & Gilman's: The Pharmacological Basis of Therapeutics, 9th ed. (1996), pp. 509-511.

Opposition submission against European Patent No. 3 054 929 filed by Dr. Luigi Rumi, May 5, 2021.

Summons and Preliminary Non-Binding Opinion of the Opposition Division in the opposition of European Patent No. 2 234 963 dated Dec. 23, 2021.

Summons and Preliminary Non-Binding Opinion of the Opposition Division in the opposition of European Patent No. 3 054 929 dated Dec. 16, 2021.

Roy et al., "Polymers in Mucoadhesive Drug-Delivery Systems: A Brief Note," Designed Monomers and Polymers 12 (2009) pp. 483-495.

Inbrija (levodopa inhalation powder) Prescribing Information, Aug. 2020.

(56) References Cited

OTHER PUBLICATIONS

Impax Laboratories, LLC, "A Study to Evaluate the Safety and Efficacy of IPX203 in Parkinson's Disease Patients With Motor Fluctuations," ClinicalTrials.gov archive (identifier NCT03670953), Jul. 26, 2021 update, 7 pages.
PCT International Search Report for PCT/US2014/059554, Jan. 13, 2015.
PCT International Written Opinion for PCT/US2014/059554, Jan. 13, 2015.
PCT International Preliminary Report on Patentability for PCT/US2014/059554, Apr. 12, 2016.
Armstrong et al., Diagnosis and Treatment of Parkinson's Disease: A Review. JAMA. Feb. 2020;323:548-560.
Bibbiani et al., "Continuous Dopaminergic Stimulation Reduces Risk of Motor Complications in Parkinsonian P," Exp Neurol. Jan. 2005;192(1):73-8.
Cilia et al., "The Modern Pre-Levodopa Era of Parkinson's Disease: Insights Into Motor Complications From Sub-Saharan Africa," Brain. Jul. 2014;137(10):2731-42.
Freitas et al., "Motor Complications of Dopaminergic Medications in Parkinson's Disease," Semin Neurol. Apr. 2017;37:147-157.
Jankovic et al., "Therapies in Parkinson's Disease," Curr Opin Neurol. Aug. 2012;25(4):433-47.
LeWitt et al., "Levodopa Therapy for Parkinson Disease a Look Backward and Forward," Neurology. Apr. 2016;86 (Suppl 1):S3-12.
Mittur et al., "Pharmacokinetics of Rytary, an Extended-Release Capsule Formulation of Carbidopa-Levodopa," Clin Pharmacokinet. Feb. 2017;56:999-1014.
Nilsson et al., "Duodenal Levodopa Infusion in Parkinson's Disease-Long-Term Experience," Acta Neurologica Scandinavica. Jun. 2001;104:343-348.
Nyholm et al., "Duodenal Levodopa Infusion Monotherapy vs Oral Polypharmacy in Advanced Parkinson Disease," Neurology. Jan. 2005;64:216-223.
Olanow et al. "Double-Blind, Double-Dummy, Randomized Study of Continuous Intrajejunal Infusion of Levodopa-Carbidopa Intestinal Gel in Advanced Parkinson's Disease," Lancet Neurol. Feb. 2014;13:141-149.
Othman et al., "Levodopa-Carbidopa Intestinal Gel Pharmacokinetics: Lower Variability Than Oral Levodopa-Carbidopa," J Parkinson's Dis. Jan. 2017;7:275-8.
Pfeiffer et al. "Clinical Implications of Gastric Complications on Levodopa Treatment in Parkinson's Disease," Parkinsonism Relat Disord. May 2020;76:63-71.
Stocchi et al., "Intermittent vs Continuous Levodopa Administration in Patients with Advanced Parkinson Disease: a Clinical and Pharmacokinetic Study," Arch Neurol. Jun. 2005;62(6):905-910.
Zhang et al., "The Advantages of Levodopa-Carbidopa Intestinal Gel for Patients with Advanced Parkinson's Disease: a Systematic Review," Drug Des Devel Ther. Feb. 2020;14:845-54.
Response to opposition of European Patent No. 3 054 929 dated Sep. 17, 2021.
Response to opposition of European Patent No. 2 234 963 dated Jun. 8, 2021.
Inbrija (levodopa inhalation powder) Prescribing Information, Dec. 2018.
Margolesky et al., "Extended-Release Oral Capsule of Carbidopa-Levodopa in Parkinson Disease," Therapeutic Advances in Neurological Disorders 2018, vol. 11, pp. 1-12.
PCT International Search Report for PCT/US2021/064693, Mar. 17, 2022.
PCT International Written Opinion for PCT/US2021/064693, Mar. 17, 2022.
Response to Summons to Attend Oral Proceedings in opposition of European Patent No. 3 054 929 dated Jul. 29, 2022.
Declaration of Richard D'Souza submitted on Jul. 29, 2022 in response to Summons to Attend Oral Proceedings in opposition of European Patent No. 3 054 929.
Response to Summons to Attend Oral Proceedings in opposition of European Patent No. 2 234 963 dated Jul. 15, 2022.
Declaration of Anita Kumar submitted on Jul. 15, 2022 in response to Summons to Attend Oral Proceedings in opposition of European Patent No. 2 234 963.

Note: Values are normalized to 100 mg LD for IR CD-LD and 280 mg LD for IPX203.

LEVODOPA DOSING REGIMEN

This application is a continuation of U.S. Ser. No. 18/823,575 filed Sep. 3, 2024 which is a continuation of U.S. Ser. No. 18/634,040 filed Apr. 12, 2024, now U.S. Pat. No. 12,109,185, which is a continuation of U.S. Ser. No. 17/967,332 filed on Oct. 17, 2022, now U.S. Pat. No. 11,986,449, which is a continuation-in-part of U.S. Ser. No. 17/558,337, filed on Dec. 21, 2021, now U.S. Pat. No. 12,194,150, which claim the benefit of U.S. Ser. No. 63/129,063 filed on Dec. 22, 2020, U.S. Ser. No. 63/150,121 filed on Feb. 17, 2021, U.S. Ser. No. 63/236,403 filed on Aug. 24, 2021 and U.S. Ser. No. 63/247,639 filed on Sep. 23, 2021, the contents of all are hereby incorporated by reference in their entireties into the present application.

FIELD OF THE INVENTION

The present invention relates to oral dosing regimens of levodopa (hereinafter "LD") and specifically oral dosing regimens that employ controlled release pharmaceutical compositions of LD. The dosing regimens are useful for the treatment of conditions such as neurological diseases associated with reduced or impaired dopamine levels and are particularly useful in treating patients with Parkinson's disease (hereinafter "PD"), post-encephalitic parkinsonism, and parkinsonism that may follow carbon monoxide intoxication or manganese intoxication.

BACKGROUND OF THE INVENTION

Patients suffering from PD frequently have periods in which their mobility becomes difficult, often resulting in an inability to move. Abnormally low levels of dopamine, a neurotransmitter that affects mobility and control of the skeletal-muscular system, is commonly believed to be the main cause of these motor symptoms in PD patients. However, administration of dopamine is not effective to treat the motor symptoms of Parkinson's disease because dopamine does not cross the blood-brain barrier. To resolve this problem, PD patients are administered levodopa, the metabolic precursor of dopamine, but levodopa is not without its issues.

Over time patients treated with LD exhibit symptoms of "wearing off," where a single dose of levodopa no longer lasts as long as in the early days of levodopa therapy (usually 5-10 years after start of levodopa therapy). Such patients may develop motor fluctuations characterized by end-of-dose failure, peak dose dyskinesia, and akinesia. The advanced form of motor fluctuations (also commonly referred to as the 'on-off' phenomenon) is characterized by unpredictable swings from mobility to immobility. Although the causes of these motor fluctuations are not completely understood, advanced patients generally benefit from treatment regimens that produce steady plasma levels of LD, such as through intestinal infusion of LD as such delivery method may mimic normally tonic endogenous dopamine. However, intestinal infusion of LD is restrictive, invasive and cumbersome. Oral delivery of LD is preferred, but plasma concentration levels remain difficult to control via oral delivery.

Combinations of LD and a decarboxylase inhibitor (typically carbidopa (hereinafter "CD")) to treat PD are known in the pharmaceutical arts. Currently, several formulations containing a combination of LD and CD are commercially available, e.g., SINEMET®, SINEMET® CR, STALEVO®, PARCOPA®, RYTARY® and their corresponding generic products. In addition, a decarboxylase inhibitor approved for use outside of the United States, is benserazide, which may be given in combination with LD.

Although many oral LD dosage forms are described in the literature, the successful development of a once or twice daily oral dosage form of LD has been elusive. LD is rapidly metabolized. LD has a plasma half-life of about 50 minutes when orally administered without CD and a plasma half-life of about 1.5 hours when orally administered with CD. Due to this short plasma half-life numerous efforts have been made to provide extended release versions of LD that will allow once or twice daily oral dosing. Although in vitro data suggests LD can be released from oral controlled release dosage forms in a manner that could allow for once and twice daily dosing, the in vivo data has proven that once and twice daily oral dosing is extremely difficult to obtain due in part to absorption issues with LD from a patient's gastrointestinal tract. LD is only absorbed from a very small portion of the patient's upper gastrointestinal tract. If the LD is not released from the dosage form in this narrow absorption window, the dosage form passes through the narrow window and the LD is released in the lower gastrointestinal tract with very low absorption. Not only is the absorption of LD limited to a small portion of the patient's upper gastrointestinal tract, LD competes with other compounds, such as dietary amino acids, at the absorption site. Even if the LD is released in the patient's narrow absorption window, the absorption could be prevented by other molecules interacting with the absorption site. This competition may cause the released levodopa to move past the narrow absorption window via normal gastric motility and be excreted without reaching a patient's bloodstream.

There remains a need for an oral LD dosage form and dosing regimen that can provide for twice or thrice daily dosing, provide steady plasma concentrations of LD with minimal 'peak-to-trough' fluctuations during daily dosing and that provides a longer duration-of-effect than the commercially available oral dosage forms of LD.

There also remains a need for an oral LD dosage form and dosing regimen that reduces or eliminates the amount of "Off" time or increases the amount of "On" and "Good On" time particularly when dosed every 6, 7, 8, 9, 10, 11 or 12 hours in a twenty-four hour time period.

There further remains a need for an oral LD dosage form and dosing regimen that reduces or eliminates the amount of "Off" time or increases the amount of "On" and "Good On" time per dose, per day and/or per waking hours in a day compared to commercially available oral LD dosage forms such as immediate release CD-LD tablets and particularly when dosed every 6, 7, 8, 9, 10, 11 or 12 hours in a twenty-four hour time period.

There also remains a need for an oral LD dosage form and dosing regimen that can be dosed prior to bedtime and provide a therapeutic benefit throughout the patient's sleep and continue to provide a therapeutic benefit when waking about 6-9 hours after the bedtime dose.

SUMMARY OF THE INVENTION

The present invention accomplishes the forgoing needs and other needs.

The present invention provides a dosing regimen that will allow for twice a day dosing to PD patients that take 500 mg or less of LD per day preferably from an immediate release LD formulation. The dosing regimen allows twice a day dosing, i.e. one dose about every six to twelve hours of an oral controlled release LD composition wherein each dose comprises about 140 to about 700 mg of LD, preferably about 210 mg LD to about 560 mg of LD and most preferably about 280 mg to about 420 mg of LD. The dose administered about every six to twelve hours may be administered as a single dosage form or multiple dosage forms. For example, a total daily dose of 560 mg of levodopa may be administered as a single dose of 280 mg of LD twice a day, i.e., every 6 to 12 hours, wherein each single dose of 280 mg of LD may be administered as two capsules per dose wherein each capsule contains 140 mg of LD or as one capsule per dose containing 280 mg of LD. In certain embodiments the total daily dose for the twice a day doing regimen will be about 400 mg to about 1200 mg LD or a dose of about 200 mg to about 600 mg every 6 to 12 hours.

The present invention also provides a dosing regimen that will allow for twice or thrice a day dosing to newly diagnosed PD patients that have not begun LD treatment or are LD naïve patients. The dosing regimen for the newly diagnosed PD patients or LD naïve patients allows twice or thrice a day dosing, i.e. one dose about every 6 to 12 hours of an oral controlled release LD composition wherein each dose comprises about 140 to about 1200 mg of LD, preferably about 210 mg LD to about 450 mg of LD and most preferably about 280 mg to about 420 mg of LD. The one dose may be administered about every six to twelve or eight hours as a single dosage form or multiple dosage forms. For example, a total daily dose of 560 mg of levodopa may be administered as a single dose of 280 mg of LD twice a day, i.e., every 12 hours, wherein each single 12 hour dose of 280 mg of LD may be administered as two capsules per dose wherein each capsule contains 140 mg of LD or as one capsule per dose containing 280 mg of LD. In certain embodiments the total daily dose for the twice a day doing regimen will be about 200 mg to about 2400 mg LD or a dose of about 140 mg to about 1200 mg every six to 12 hours. In some embodiments, the dosing regimen comprises a starting twice a day dose of a controlled release LD formulation, wherein each dose comprises about 140 mg of LD. The dose is administered for the first three days and is gradually increased as required from the fourth day onwards. The dosing frequency may change from twice daily to four times daily based on individual patients' response to achieve optimal balance of efficacy and tolerability. The patients are maintained on the lowest dosage required to achieve symptomatic control and to minimize adverse reactions such as dyskinesia and nausea. The maximum recommended daily dose comprises about 600 mg of CD and about 2400 mg of LD.

The present invention also provides a dosing regimen that will allow for dosing every 4-12 hours, preferably every 6-12 hours i.e. dosing 2, 3, 4 or 5 times a day, with substantially no "Off" time or zero "Off" time between doses.

The present invention further provides a dosing regimen that will allow for dosing every 4-12 hours, preferably every 6-12 hours i.e. dosing 2, 3, 4 or 5 times a day, with an increased "On" time or increased "Good On" time with each dose, per day and/or per waking hours in a day compared to an oral immediate release CD-LD dose or the total immediate release CD-LD doses per day or per waking hours.

The present invention also provides a dosing regimen that allows the controlled release dosage forms described herein to be taken before bedtime and thereby provide therapeutic benefits to the patient upon awaking six to nine hours, preferably seven to eight hours after administration. In certain embodiments, the controlled release dosage forms useful in the present invention are administered every six to seven or seven to eight hours in a twenty-four hour period and after 7 to 15 days of consecutive treatment, the patient will obtain a steady state minimum LD plasma level of at least 250 ng/mL, preferably at least 500 ng/mL and most preferably at least 1000 ng/mL between doses and will exhibit therapeutic benefits for the seven to eight hours prior to administration of the next dose.

The present invention further provides a dosing regimen that will allow for dosing every 6-12 hours i.e. dosing 2, 3, or 4 times a day, and will reduce the number of motor fluctuations per dose, per day and/or per waking hours in a day compared to an oral immediate release CD-LD dose or the total immediate release CD-LD doses per day or per waking hours.

The present invention also provides a dosing regimen that will allow for dosing every 6-12 hours i.e. dosing 2, 3, or 4 times a day, and will increase the patients emotional well-being per dose, per day and/or per waking hours in a day compared to an oral immediate release CD-LD dose or the total immediate release CD-LD doses per day or per waking hours.

The present invention also further provides a dosing regimen that will allow for dosing every 6-12 hours i.e. dosing 2, 3, or 4 times a day, and will reduce the patients perceptual problems and/or hallucinations per dose, per day and/or per waking hours in a day compared to an oral immediate release CD-LD dose or the total immediate release CD-LD doses per day or per waking hours.

In certain embodiments, the controlled release dosage form used in the dosing regimen of the present invention is a multi-particulate dosage form comprising an immediate release amount of LD and a modified or controlled release amount of LD. The modified or controlled release amount of LD may be present as a modified or controlled release component, such as a bead, pellet, granule or mini-tablet, comprising a core containing LD that is mixed, coated or layered with a controlled release material and/or a mucoadhesive material and may optionally be coated with an enteric material, preferably an enteric polymer.

The controlled release dosage forms used in present invention may also comprise a decarboxylase inhibitor, such as CD. The decarboxylase inhibitor, such as CD, may be present in an immediate release form, a modified or controlled release form or both.

DETAILED DESCRIPTION OF THE INVENTION

Figure 1:
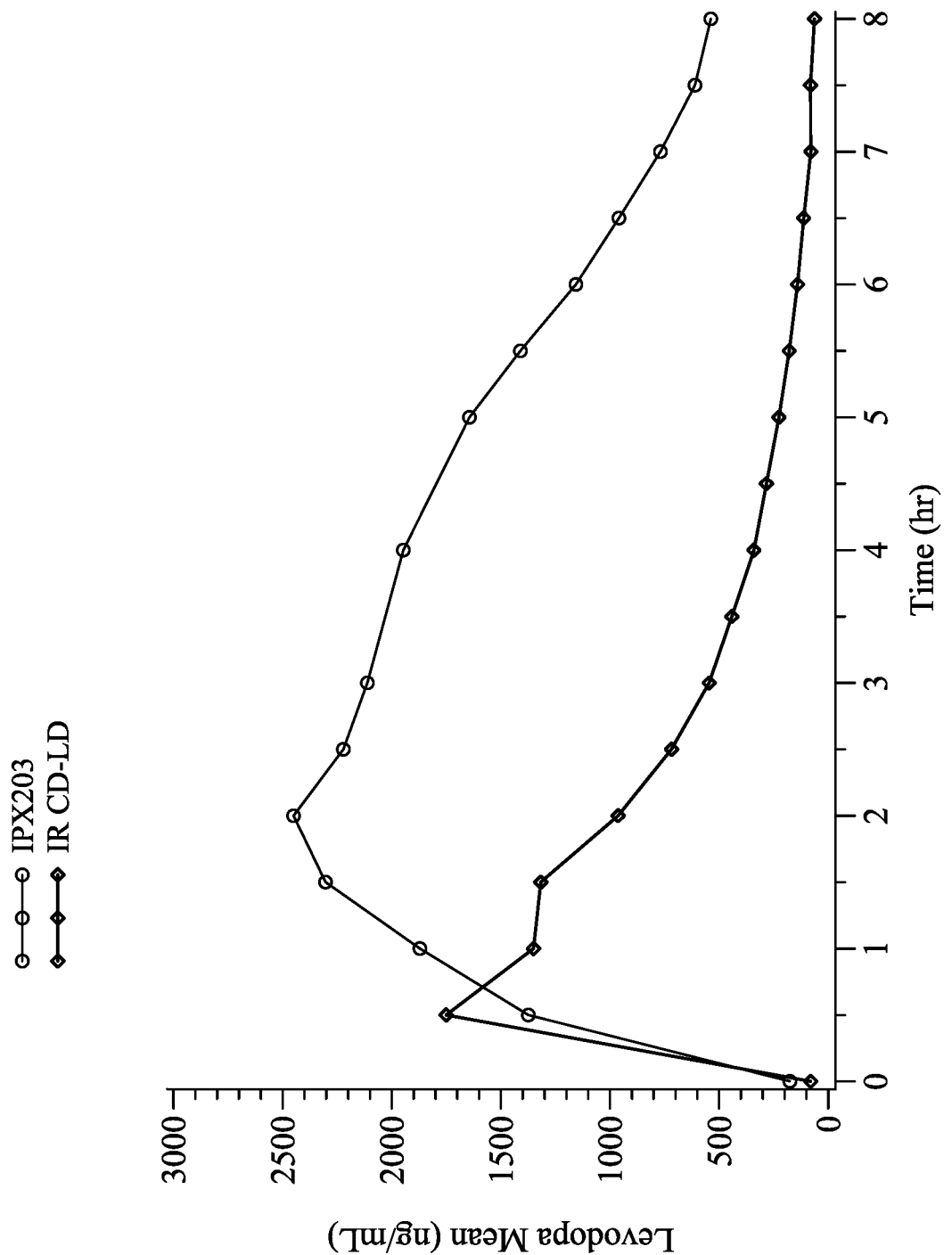
FIG. 1 shows the Day 1 in vivo levodopa plasma profiles for the formulations tested in Example 8 under fasted conditions.

Unless defined otherwise, all technical and scientific terms used herein have the same meaning as commonly understood by one of ordinary skill in the art to which the present disclosure belongs.

It must be noted that as used herein and in the appended claims, the singular forms "a," "an," and "the" include plural referents unless the context clearly dictates otherwise. Thus, for example, reference to "a formulation" includes a plurality of formulations.

As used herein, the term "about" when used before a numerical designation, e.g., temperature, time, amount, concentration, and such other, including a range, indicates approximations which may vary by (+) or (−) 10%, 5% or 1%.

As used herein, the term "immediate release" refers to a dosage form or composition that releases the specified amount of the active ingredient such as LD and/or CD within 30 minutes or less, 25 minutes or less, 20 minutes or less, 15 minutes or less following administration to a patient or subject or when tested in a United States Pharmacopeia Type I or Type II dissolution apparatus using 500-900 ml of an aqueous media. A representative example of an immediate release LD dosage form is the U.S. Food and Drug Administration (FDA) approved and commercially available tablet product, SINEMET®, sold by Merck Sharpe & Dohme Corp. or a U.S. FDA "AB" rated generic to SINEMET® such as the U.S. FDA approved tablets sold by Actavis Elizabeth, LLC, Apotex Inc., Mayne Pharma LLC, Mylan Pharmaceuticals Inc., Sciegen Pharmaceuticals Inc. or Sun Pharmaceutical Industries, Inc.

As used herein the term "component" is used in its broadest conventional interpretation unless dictated by context or specifically stated. More specifically, a component may be an element, a constituent part, a single ingredient or a mixture of ingredients. For example, an immediate release component may include a single ingredient such as a drug itself or it may be a combination of a drug and one or more pharmaceutically acceptable excipients provided the "immediate release component" will release the drug immediately upon administration.

Target Patient Populations

The present invention provides controlled release levodopa compositions that are useful for all PD patients, including PD patients with primary parkinsonism/idiopathic parkinsonism, post-encephalitic parkinsonism, parkinsonism that may follow carbon monoxide intoxication, or parkinsonism that may follow manganese intoxication. The compositions are recommended to be dosed 2 to 4 times a day and are specifically useful for the following target patient populations.

A first target patient population comprises PD patients, including PD patients with primary parkinsonism/idiopathic parkinsonism, post-encephalitic parkinsonism, parkinsonism that may follow carbon monoxide intoxication, or parkinsonism that may follow manganese intoxication, that are currently being treated with a total daily immediate-release LD dose of 500 mg or less, wherein the 500 mg or less total daily dose is administered in two, three, four or more divided doses throughout a 24 hour period. In some embodiments, the PD patients in the first target patient population are being administered an immediate release oral LD composition such as an immediate release oral tablet comprising about 100 mg 150 mg, or 200 mg of LD three, four or five times a day In some embodiments, the PD patients in the first target patient population that are on a total daily LD dose of less than 500 are being administered a combination LD composition such as an oral capsule or tablet comprising an immediate release LD component and a controlled release LD component. In some embodiments, dose conversion from the immediate release LD dose to the combination LD composition comprises multiplying the most frequent single dose of immediate release LD by 2.8 as recommended in Table 1.

TABLE 1

| Most Frequent Immediate Release LD Single Dose (mg) | Recommended Starting Dose of Controlled Release Composition (mg) | Recommended Dosing Frequency of Controlled release Composition |
|---|---|---|
| 100 | 280 | 2 times daily |
| 150 | 420 | 2 times daily |
| 200 | 560 | 2 times daily |

In another embodiment the PD patients in the first target patient population that are on most frequent immediate release LD single dose of 100 mg are administered a combination LD composition comprising a starting LD dose of 280 mg twice daily. In another embodiment the PD patients in the first target patient population that are on most frequent immediate release LD single dose of 150 mg are administered a combination LD composition comprising a starting LD dose of 420 mg twice daily. In another embodiment the PD patients in the first target patient population that are on most frequent immediate release LD single dose of 200 mg are administered a combination LD composition comprising a starting LD dose of 560 mg twice daily.

In another embodiment a first target patient population comprises PD patients that are currently being treated with a most frequent single daily dose of immediate release levodopa of greater than 200 mg, wherein the dose is administered 2, 3, 4, or 5 times daily, and wherein the dose is administered in single or multiple dosage units. In another embodiment the PD patients on a most frequent single dose of immediate-release levodopa of greater than 200 mg are administered a combination LD composition including an immediate release component and a controlled release component. In some embodiments, PD patients on a most frequent single daily dose of immediate-release levodopa of greater than 200 mg dose are administered the combination LD composition with a starting LD dose of 700 mg, administered thrice daily, wherein the dose is administered in single or multiple dosage units.

In yet another embodiment the PD patient in the first target patient population is a newly diagnosed PD patient and/or PD patients that have not begun treatment with LD/LD naïve patients. In another embodiments, the LD naïve patients are administered with a twice daily starting dose of a combination LD composition comprising an immediate release component and a controlled release component, wherein the combination LD composition comprise about 140 mg of LD/dose, and wherein the dose in administered as single or multiple dosage units. In another embodiment, the starting LD dose of 140 mg is administered for the first three days and gradually increased as required from the fourth day onwards. The dosing frequency may change from twice daily to four times daily based on individual patients' response to achieve optimal balance of efficacy and tolerability. The patients are maintained on the lowest dosage required to achieve symptomatic control and to minimize adverse reactions such as dyskinesia and nausea. The maximum recommended daily dose comprises about 600 mg of CD and about 2400 mg of LD.

A second target patient population comprises LD experienced PD patients, including PD patients with primary parkinsonism/idiopathic parkinsonism, post-encephalitic parkinsonism, parkinsonism that may follow carbon monoxide intoxication, or parkinsonism that may follow manganese intoxication, with motor fluctuations. A subset of the second target patient population includes PD patients that have been receiving LD therapy for at least 4, 5, 6, 7, 8 or more years and is experiencing motor complications or motor fluctuations while receiving LD therapy, particularly immediate release oral LD therapy. This subset of the second target patient population may be referred to as advanced PD patients. The second target patient population comprises PD patients that are currently being treated with a total daily immediate-release LD dose of 500 mg or less, wherein the 500 mg or less total daily LD dose is administered in two, three, four or more divided doses throughout a 24 hour period. In some embodiments, the PD patients in the first target patient population are being administered an immediate release oral LD composition such as an immediate release oral tablet comprising about 100 mg 150 mg, or 200 mg of LD three, four or five times a day. In some embodiments, the PD patients in the second target patient population that are on a total daily LD dose of less than 500 are being administered a combination LD composition such as an oral capsule or tablet comprising an immediate release LD component and a controlled release LD component. In some embodiments, dose conversion from the immediate release LD dose to the combination LD composition comprises multiplying the most frequent single dose of immediate release LD by 2.8 as recommended in Table 1. In another embodiment the PD patients in the first target patient population that are on a most frequent immediate release LD single dose of 100 mg are administered a combination LD composition comprising a starting LD dose of 280 mg twice daily. In another embodiment the PD patients in the second target patient population that are on a most frequent immediate release LD single dose of 150 mg are administered a combination LD composition comprising a starting LD dose of 420 mg twice daily. In another embodiment the PD patients in the second target patient population that are on a most frequent immediate release LD single dose of 200 mg are administered a combination LD composition comprising a starting LD dose of 560 mg twice daily.

In another embodiment a second target patient population comprises PD patients that are currently being treated with a most frequent single daily dose of immediate-release levodopa of greater than 200 mg, wherein the dose is administered 2, 3, 4, or 5 times daily, and wherein the dose is administered in single or multiple dosage units. In another embodiment the PD patients on a most frequent single dose of immediate-release levodopa of greater than 200 mg are administered a combination LD composition including an immediate release component and a controlled release component. In another embodiment, the combination LD composition comprises a starting LD dose of 700 mg, administered thrice daily, wherein the dose is administered in single or multiple dosage units.

In yet another embodiment the PD patient in the second target patient population is a newly diagnosed PD patient and/or PD patients that have not begun treatment with LD/LD naïve patients. In another embodiments, the LD naïve patients are administered with a twice daily starting dose of a combination LD composition comprising an immediate release component and a controlled release component, wherein the combination LD composition comprise about 140 mg of LD/dose, and wherein the dose in administered as single or multiple dosage units. In another embodiment, the starting LD dose of 140 mg is administered for the first three days and gradually increased as required from the fourth day onwards. The dosing frequency may change from twice daily to four times daily based on individual patients' response to achieve optimal balance of efficacy and tolerability. The patients are maintained on the lowest dosage required to achieve symptomatic control and to minimize adverse reactions such as dyskinesia and nausea. The maximum recommended daily dose comprises about 600 mg of CD and about 2400 mg of LD. A third target patient population comprises all PD patients including those patients in the first and second target patient population as well as patients with advanced PD, unless specifically stated. A third target patient population comprises PD patients that are currently being treated with a total daily immediate-release LD dose of 500 mg or less, wherein the 500 mg or less total daily LD dose is administered in two, three, four or more divided doses throughout a 24 hour period. In some embodiments, the PD patients in the third target patient population are being administered an immediate release oral LD composition such as an immediate release oral tablet comprising about 100 mg 150 mg, or 200 mg of LD three, four or five times a day In some embodiments, the PD patients in the third target patient population that are on a total daily LD dose of less than 500 are being administered a combination LD composition such as an oral capsule or tablet comprising an immediate release LD component and a controlled release LD component. In some embodiments, dose conversion from the immediate release LD dose to the combination LD composition comprises multiplying the most frequent single dose of immediate release LD by 2.8 as recommended in Table 1. In another embodiment the PD patients in the third target patient population that are on a most frequent immediate release LD single dose of 100 mg are administered a combination LD composition comprising a starting LD dose of 280 mg twice daily. In another embodiment the PD patients in the third target patient population that are on a most frequent immediate release LD single dose of 150 mg are administered a combination LD composition comprising a starting LD dose of 420 mg twice daily. In another embodiment the PD patients in the third target patient population that are on a most frequent immediate release LD single dose of 200 mg of immediate release LD are administered a combination LD composition comprising a starting LD dose of 560 mg twice daily.

In another embodiment a third target patient population comprises PD patients that are currently being treated with a most frequent single daily dose of immediate-release levodopa of greater than 200 mg, wherein the dose is administered 2, 3, 4, or 5 times daily, and wherein the dose is administered in single or multiple dosage units. In another embodiment the PD patients on a most frequent single dose of immediate-release levodopa of greater than 200 mg are administered a combination LD composition including an immediate release component and a controlled release component. In another embodiment, the combination LD composition comprises a starting LD dose of 700 mg, administered thrice daily, wherein the dose is administered in single or multiple dosage units.

In yet another embodiment the PD patient in the third target patient population is a newly diagnosed PD patient and/or PD patients that have not begun treatment with LD/LD naïve patients. In another embodiments, the LD naïve patients are administered with a twice daily starting dose of a controlled release combination LD composition comprising an immediate release component and a controlled release component, wherein the controlled release combination LD composition comprise about 140 mg of LD/dose, and wherein the dose in administered as single or multiple dosage units. In another embodiment, the starting LD dose of 140 mg is administered for the first three days and gradually increased as required from the fourth day onwards. The dosing frequency may change from twice daily to four times daily based on individual patients' response to achieve optimal balance of efficacy and tolerability. The patients are maintained on the lowest dosage required to achieve symptomatic control and to minimize adverse reactions such as dyskinesia and nausea. The maximum recommended daily dose comprises about 600 mg of CD and about 2400 mg of LD. Most patients require one or two titration steps to reach a stable total daily dose of the controlled release combination composition of the disclosure. The dose strength and frequency is adjusted based on individual patient response to achieve the optimal balance of efficacy and tolerability.

Contraindications

The LD compositions of the disclosure are contraindicated in patients that are currently taking a nonselective monoamine oxidase (MAO) inhibitor (e.g., phenelzine and tranylcypromine) or have recently (within 2 weeks) taken a nonselective MAO inhibitor. Hypertension can occur if taken concurrently with nonselective MAO inhibitor. The LD compositions of the disclosure are also contraindicated in patients who have demonstrated hypersensitivity to drug and ingredients present in the composition.

Dosing Regimen

The present disclosure provides controlled release LD compositions comprising capsules or tablets comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD. In a preferred embodiment, the disclosure provides LD compositions comprising capsules comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD.

The present invention allows twice a day oral dosing of LD to above-described first target patient population and thereby controlling the patient's PD symptoms. More specifically, the twice a day dosing will control or manage the patient's motor fluctuations symptoms and in certain embodiments will reduce the patient's total "Off" time to less than 5 hours, less than 4 hours, less than 3 hours, less than 2 hours, less than 1 hour and less than 0.5 hours a day. The twice a day dosing will control or manage the patient's motor fluctuations symptoms and in certain embodiments will also reduce the patient's total "Off" time per dose, per day and/or during waking hours to less than 5 hours, less than 4 hours, less than 3 hours, less than 2 hours, less than 1 hour and less than 0.5 hours per dose, per day and/or during waking hours in a 24 hour period. The twice a day dosing will control or manage the patient's motor fluctuations symptoms and in certain embodiments will increase the patient's total "On" time to at least about 5 hours, e.g., more than 5 hours, more than 6 hours, more than 7 hours, more than 8 hours, more than 9 hours, more than 10 hours or more than 11 hours during the 12 hour dose interval (i.e., per dose). The twice a day dosing will control or manage the patient's motor fluctuations symptoms and in certain embodiments will also increase the patient's total "Good On" time to at least about 5 hours, e.g., more than 5 hours, more than 6 hours, more than 7 hours, more than 8 hours, more than 9 hours, more than 10 hours or more than 11 hours during the 12 hour dosing time interval (per dose). The terms "Off", "On" and "Good On" time with respect to PD patients are well known terms to those skilled in the treatment of PD patients and a general description is provided in Example 8 below.

The first target patient population will take or be administered a total daily dose of LD of about 140 mg to about 2500 mg of LD, preferably about 280 mg to about 2400 mg, o about 420 mg to about 2400 mg, or 560 mg to 2400 of LD. This total daily LD dose may be divided into two equal or unequal doses administered twice a day wherein the dose taken or administered every six to twelve hours is from about 200 mg LD to about 600 mg of LD, preferably about 200 mg to about 560 mg of LD, and most preferably about 280 mg LD to about 560 mg LD. The LD will be taken by or administered to the PD patient in the form of an oral controlled release dosage form, preferably a multiparticulate dosage form comprising an immediate release LD component and a controlled release LD component as described in greater detail below.

In certain embodiments, the LD dose taken or administered twice a day by the first target patient population will comprise about 140 mg of LD, 210 mg of LD, 280 mg of LD, 350 mg LD, 410 mg LD, or 420 mg of LD. In certain embodiments, the LD dose taken or administered twice a day will comprise one or more tablets or capsules comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD. In a preferred embodiment, the LD composition comprises capsules comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD. The tablets or capsules may be swallowed whole or alternatively, the tablets may be crushed and sprinkled onto food, such as yogurt or applesauce or the contents of the capsule may be sprinkled onto food such as yogurt or applesauce and the food swallowed by the patient.

The present invention further allows for thrice daily dosing of the controlled release compositions of the disclosure for patients on five times daily dosing of immediate release LD compositions. In certain embodiments, the total daily LD dose may be divided into three equal or unequal doses administered about every six to eight hours, wherein the dose taken or administered every six to eight hours is from about 200 mg LD to about 600 mg of LD, preferably about 200 mg to about 560 mg of LD, and most preferably about 280 mg LD to about 560 mg LD. The LD will be taken by or administered to the PD patient in the form of an oral controlled release dosage form/composition, preferably a multiparticulate dosage form comprising an immediate release LD component and a controlled release LD component.

In certain embodiments, the LD dose taken or administered every six to eight hours by the first target patient population will comprise about 140 mg of LD, 210 mg of LD, 280 mg of LD, 350 mg LD, 410 mg LD, or 420 mg of LD. In certain embodiments, the LD dose taken or administered every six to eight hours will comprise one or more tablets or capsules comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD. In a preferred embodiment, the LD composition comprises capsules comprising: (i) about 35 mg CD and about 140 mg LD; (ii) about 52.5 mg CD and about 210 mg LD; (iii) about 70 mg CD and about 280 mg LD; and (iv) 87.5 mg CD and about 350 mg LD. The tablets or capsules may be swallowed whole or alternatively, the tablets may be crushed and sprinkled onto food, such as yogurt or applesauce or the contents of the capsule may be sprinkled onto food such as yogurt or applesauce and the food swallowed by the patient.

In certain embodiments of the twice or thrice daily dosing regimen of the present invention for the first target patient population provides a LD plasma level of at least about 200 ng/mL within about 0.25 hours to about 1 hour after administration based on a single or multiple dose administration. In some embodiments of the dosing regimen of the present invention for the first target patient population provides a LD plasma level of from about 200 ng/mL to about 2000 ng/ml within about 0.25 hours to about 1 hour after administration based on a single dose or multiple dose administration. In certain embodiments of the dosing regimen of the present invention for the first target patient population provides a LD plasma level of at least about 300 ng/mL, at least about 350 ng/mL, at least about 400 ng/mL, at least about 425 ng/mL, at least about 450 ng/mL, at least about 475 ng/mL, at least about 500 ng/mL, at least about 525 ng/mL, at least about 550 ng/mL, at least about 575 ng/mL, at least about 600 ng/mL, at least about 625 ng/mL, at least about 650 ng/mL, at least about 675 ng/mL, at least about 700 ng/mL, at least about 725 ng/mL, at least about 750 ng/mL, at least about 775 ng/mL, at least about 800 ng/mL, at least about 825 ng/mL, at least about 850 ng/mL, at least about 875 ng/mL, at least about 900 ng/mL, at least about 925 ng/mL, at least about 950 ng/mL, at least about 975 ng/mL, at least about 1000 ng/mL, at least about 1050 ng/mL, at least about 1100 ng/mL, at least about 1150 ng/mL, at least about 1200 ng/mL, about 1225 ng/mL, about 1250 ng/mL, about 1275 ng/mL, about 1300 ng/mL, about 1375 ng/mL, about 1400 ng/mL, about 1425 ng/mL, about 1500 ng/mL, about 1525 ng/mL, about 1550 ng/mL, about 1575 ng/mL, about 1600 ng/mL, about 1650 ng/mL, about 1700 ng/mL, about 1800 ng/mL, about 1900 ng/mL, about 2000 ng/mL, or intermediate values therein within about 0.25 hours to about 1 hour after administration, based on a single or a multiple dose administration. In certain embodiments of the dosing regimen of the present invention for the first target patient population provides a LD plasma level of at least about 400 ng/mL within about 0.25 hours to about 1 hour after administration, based on a single or multiple dose administration.

In certain embodiments of the dosing regimen of the present invention for the first target patient population a provides a LD plasma level of at least about 300 ng/mL at least about 310 ng/mL, at least about 315 ng/mL at least about 320 ng/mL, at least about 325 ng/mL, at least about 330 ng/mL, at least about 335 ng/mL, at least about 340 ng/mL, at least about 345 ng/mL, at least about 350 ng/mL, at least about 355 ng/mL, about 360 ng/mL, about 365 ng/mL, about 370 ng/mL, at least about 375 ng/mL, at least about 380 ng/mL, at least about 385 ng/mL at least about 390 ng/mL, at least about 395 ng/mL at least about 400 ng/mL at least about 405 ng/mL, at least about 410 ng/mL, at least about 415 ng/mL, at least about 420 ng/mL, at least 425 ng/mL, at least about 430 ng/mL, at least about 435 ng/mL, at least about 440 ng/mL, at least about 445 ng/ml, about 450 ng/ml, or any intermediate values therein, within about 60 minutes about 55 minutes, about 50 minutes, about 45 minutes, about 40 minutes, about 35 minutes, about 30 minutes, about 25 minutes, about 20 minutes, about 15 minutes, about 10 minutes, or any intermediate periods thereinafter administration based on a single or multiple dose administration. The dosage form administered further provides a CD plasma level of at least about 30 ng/mL, about 35 ng/ml, about 40 ng/mL, about 45 ng/mL, about 50 ng/mL, about 55 ng/mL, about 60 ng/mL, about 65 ng/mL, about 70 ng/mL, 75 ng/mL, 80 ng/mL, 85 ng/mL, 90 ng/mL, 95 ng/mL or 100 ng/mL or any intermediate values therein within 0.25 to 1 hour, preferably within 0.25 to 0.75 hours after administration based on a single or multiple dose administration and maintains the CD plasma level above about 75 ng/mL, about 85 ng/mL, about 95 ng/mL, about 100 ng/mL, about 110 ng/mL, about 120 ng/mL, about 125 ng/mL, about 130 ng/mL, about 135 ng/mL, about 140 ng/mL, about 145 ng/mL, about 150 ng/mL from about 1 hour after dosing to about 7 or 8 hours after dosing.

In certain embodiments of the twice or thrice daily dosing regimen of the present invention to the first target patient population provides a steady state minimum LD plasma level of at least about 250 ng/mL, at least about 275 ng/mL, at least about 300 ng/mL, at least about 325 ng/mL, at least about 350 ng/mL, at least about 375 ng/mL, at least about 400 ng/mL, at least about 425 ng/mL, 450, ng/mL, 47 ng/mL, at least about 475 ng/mL, at least about 500 ng/mL, at least about 525 ng/mL, at least about 550 ng/mL, at least about 575 ng/mL, at least about 600 ng/mL, at least about 625 ng/mL, at least about 650 ng/mL, at least about 675 ng/mL, at least about 700 ng/mL, at least about 725 ng/mL, at least about 750 ng/mL, at least about 775 ng/mL, at least about 800 ng/mL, at least about 825 ng/mL, at least about 850 ng/mL, at least about 875 ng/mL, at least about 900 ng/mL, at least about 925 ng/mL, at least about 950 ng/mL, at least about 975 ng/mL, at least about 1000 ng/mL, at least about 1050 ng/mL, at least about 1100 ng/mL, at least about 1150 ng/mL, at least about 1200 ng/mL, at least about 1250 ng/mL, at least about 1300 ng/mL, at least about 1350 ng/mL, at least about 1400 ng/mL, at least about 1450 ng/mL, at least about 1500 ng/mL, or intermediate values therein after six to eight hours of dosing. The dosing regimen of the present invention should also obtain a steady state minimum CD plasma level of at least about 40 ng/mL, at least about 45 ng/mL, at least about 50 ng/mL, at least about 55 ng/mL, at least about 60 ng/mL, at least about 65, ng/mL, at least about 70 ng/mL at least about 75 ng/mL, at least about 80 ng/mL at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, or any intermediate values therein after six to eight hours of dosing.

The dosing regimen of the present invention allows the PD patient in the first target patient population to experience improved therapeutic benefits after dosing and before the next dose compared to the patient's symptoms without the administration of the controlled release dosage forms or compared to treatment with an immediate release CD-LD oral dosage form. An improved therapeutic benefit may be:

(i) an improvement or increase of at least 10%, 15%, 20%, 25%, 30%, 35%, 40%, 45% or 50% in the patient's motor state as determined by a qualified clinician;

(ii) an improvement or increase of at least 10%, 15%, 20%, 25%, 30%, 35%, 40%, 45% or 50% in the patient's motor state as determined by a patient's PD diary;

(iii) an improvement or increase of at least 10%, 15%, 20%, 25%, 30%, 35%, 40%, 45% or 50% in the subjects tremor, dyskinesia and/or mobility as measured by a Kinesia 360 Sensor;

(iv) a reduction of the Movement Disorders Society version of the Unified Parkinson's Disease Rating Scale ("MDS-UPDRS") scores by 2, 3, 4, 5, 6, 7, 8, 9, 10, 11, 12, 13, 14, 15, 16, 17, 18, 19 20 or more points;

(v) an increase of at least 10%, 15%, 20%, 25%, 30%, 35%, 40%, 45% or 50% in the patient's total "On" time per day or during waking hours compared to a comparable total immediate release CD-LD doses per day or per waking hours;

(vi) an increase of at least 10%, 15%, 20%, 25%, 30%, 35%, 40%, 45% or 50% in the patient's total "Good On" time per day or during waking hours compared to a comparable total immediate release CD-LD doses per day or per waking hours;

(vii) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "On" time per dose, per day and/or during waking hours per day compared to a comparable oral dose of an immediate release CD-LD dosage form or the total immediate release CD-LD doses per day or per waking hours;

(viii) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "Good On" time per dose, per day and/or during waking hours per day compared to a comparable oral dose of an immediate release CD-LD dosage form or the total immediate release CD-LD doses per day or per waking hours;

(ix) a decrease of at least 10%, 15%, 20%, 25%, 30%, 35%, 40%, 45% or 50% in the patient's total "Off" time per day or during waking hours compared to a comparable oral dose of an immediate release CD-LD dosage form or the total immediate release CD-LD doses per day or per waking hours;

(x) a decrease of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "Off" time per dose, per day and/or during waking hours per day compared to a comparable oral dose of an immediate release CD-LD dosage form or the total immediate release CD-LD doses per day or per waking hours;

(xi) an increase of at least 10%, 15%, 20%, 25%, 30%, 35%, 40%, 45% or 50% in the patient's Patient Global Impression of Change ("PGI-C") score, Clinical Global Impression of Change ("CGI-C") score and/or the 39-Item Parkinson's Disease Questionnaire ("PDQ-39") score compared to a comparable oral dose of an immediate release CD-LD dosage form or the total immediate release CD-LD doses per day or per waking hours;

(xii) a decrease of at least 10%, 15%, 20%, 25%, 30%, 35%, 40%, 45% or 50% in the average number of motor fluctuations per day compared to a comparable oral dose of an immediate release CD-LD dosage form or the total immediate release CD-LD doses per day or per waking hours;

(xiii) a decrease of at least 10%, 15%, 20%, 25%, 30%, 35%, 40%, 45% or 50% in the perceptual problems and/or hallucinations per day compared to a comparable oral dose of an immediate release CD-LD dosage form or the total immediate release CD-LD doses per day or per waking hours; or (xiv) any combination of the foregoing.

In certain embodiments the improved therapeutic benefit includes at least 10%, 15%, 20%, 25%, 30%, 35%, 40%, 45% or 50% improvement in MDS-UPDRS Part III scores.

A more detailed explanation of the motor states, PD diaries, MDS-UPDRS, PGI-C, CGIC and PDQ-39 is provided below in Examples 8, 9 and 11 herein.

The invention also provides dosing regimens for treating a subject with PD, idiopathic PD/primary parkinsonism, post-encephalitic parkinsonism, parkinsonism that may follow carbon monoxide intoxication, or parkinsonism that may follow manganese intoxication in the second or third target patient populations. The dosing regimen comprise orally administering to a patient in need of such treatment a controlled release dosage form as described herein to provide an effective amount of LD to improve and/or treat the symptoms of PD, Idiopathic PD/primary Parkinsonism, post-encephalitic parkinsonism, parkinsonism that may follow carbon monoxide intoxication, or parkinsonism that may follow manganese intoxication for at least 6 to 14 hours, preferably 7 to 12 hours post dose.

In certain embodiments of the present invention, the dosing regimen for the second or third target patient populations comprise orally administering to the subject a controlled release dosage form described herein every six, seven eight, nine, ten, eleven, or twelve hours in a twenty four hour period (i.e., a day) to provide an effective amount of LD to improve and/or treat symptoms of PD, Idiopathic PD/primary Parkinsonism, post-encephalitic parkinsonism, parkinsonism that may follow carbon monoxide intoxication, or parkinsonism that may follow manganese intoxication. The controlled release dosage form administered should provide an LD plasma level of at least about 200 ng/mL, at least about 225 ng/mL, at least about 250 ng/mL, at least about 275 ng/mL, at least about 300 ng/mL, at least about 325 ng/mL, at least about 350 ng/mL, at least about 375 ng/mL, at least about 400 ng/mL at least about 425 ng/mL, at least about 475 ng/mL, at least about 500 ng/mL, at least about 525 ng/mL, at least about 550 ng/mL, at least about 575 ng/mL, at least about 600 ng/mL, at least about 625 ng/mL, at least about 650 ng/mL, at least about 675 ng/mL, at least about 700 ng/mL, at least about 725 ng/mL, at least about 750 ng/mL, at least about 775 ng/mL, at least about 800 ng/mL, at least about 825 ng/mL, at least about 850 ng/mL, at least about 875 ng/mL, at least about 900 ng/mL, at least about 925 ng/mL, at least about 950 ng/mL, at least about 975 ng/mL, at least about 1000 ng/mL, at least about 1050 ng/mL, at least about 1100 ng/mL, at least about 1150 ng/mL, at least about 1200 ng/mL, about 1225 ng/mL, about 1250 ng/mL, about 1275 ng/mL, about 1300 ng/mL, about 1375 ng/mL, about 1400 ng/mL, about 1425 ng/mL, about 1500 ng/mL, about 1525 ng/mL, about 1550 ng/mL, about 1575 ng/mL, about 1600 ng/mL, about 1650 ng/mL, about 1700 ng/mL, about 1800 ng/mL, about 1900 ng/mL, about 2000 ng/mL, or intermediate values therein, within 0.25 to 1 hour, preferably within about 0.25 to about 0.75 hours after administration based on a single or multiple dose administration. The controlled release dosage form administered should also provide a CD plasma level of at least about 30 ng/mL, about 40 ng/mL, about 50 ng/mL, about 60 ng/mL, about 70 ng/mL, about 75 ng/mL, about 80 ng/mL, about 85 ng/mL, about 90 ng/mL, about 95 ng/mL or about 100 ng/mL within about 0.25 to about 1 hour, preferably within about 0.25 to about 0.75 hours after administration based on a single or multiple dose administration and should maintain the CD plasma level above 75 ng/mL, 85 ng/mL, 95 ng/mL, 100 ng/mL, 110 ng/mL, 120 ng/mL, 125 ng/mL, 130 ng/mL, 135 ng/mL, 140 ng/mL, 145 ng/mL, 150 ng/mL, or any intermediate values therein after about six to eight hours of dosing.

In certain embodiments of the present invention, the dosing regimen for the second or third target patient populations comprise orally administering to the subject a controlled release dosage form described herein every 6 to 12 hours, preferably about every 6 to 9 hours, for at least 7, 8, 9, 10, 11, 12, 13, 14, or 15 days to obtain a steady state minimum LD plasma level of at least about 250 ng/mL, at least about 275 ng/mL, at least about 300 ng/mL, at least about 325 ng/mL, at least about 350 ng/mL, at least about 375 ng/mL, at least about 400 ng/mL, at least about 425 ng/mL, 450, ng/mL, 47 ng/mL, at least about 475 ng/mL, at least about 500 ng/mL, at least about 525 ng/mL, at least about 550 ng/mL, at least about 575 ng/mL, at least about 600 ng/mL, at least about 625 ng/mL, at least about 650 ng/mL, at least about 675 ng/mL, at least about 700 ng/mL, at least about 725 ng/mL, at least about 750 ng/mL, at least about 775 ng/mL, at least about 800 ng/mL, at least about 825 ng/mL, at least about 850 ng/mL, at least about 875 ng/mL, at least about 900 ng/mL, at least about 925 ng/mL, at least about 950 ng/mL, at least about 975 ng/mL, at least about 1000 ng/mL, at least about 1050 ng/mL, at least about 1100 ng/mL, at least about 1150 ng/mL, at least about 1200 ng/mL, at least about 1250 ng/mL, at least about 1300 ng/mL, at least about 1350 ng/mL, at least about 1400 ng/mL, at least about 1450 ng/mL, at least about 1500 ng/mL, or intermediate values therein after 6 to 9 hours, preferably about 7 to about 8 hours of dosing and before the next dose. The controlled release dosage forms should also be administered every 6 to 12 hours, preferably about 6 to about 8 hours for at least 7, 8, 9, 10, 11, 12, 13, 14, or 15 days to obtain a steady state minimum CD plasma level of at least 40 ng/mL, 45 ng/mL, 50 ng/mL, 55 ng/mL, 60 ng/mL, 65, ng/mL, 70 ng/mL or 75 ng/mL after six to nine hours, preferably about seven to about eight hours of dosing and before the next dose.

The dosing regimens of the present invention to the first, second and third target patient populations may further include the step of orally administering the controlled release dosage forms described herein so at least one of the administrations of the controlled release dosage forms occurs within 30 minutes, 15 minutes, 10 minutes, 5 minutes before or at bedtime and provides a therapeutic benefit upon awakening six, seven or eight hours after the bedtime administration and in the first target patient population up to about 7, 8, 9, 10, 11, or 12 hours after the bedtime administration. In certain embodiments of this bedtime treatment method, after dosing the controlled release dosage forms described herein every six, seven, eight, nine, ten, eleven or twelve hours in a twenty-four hour period for at least 7, 8, 9, 10, 11, 12, 13, 14, or 15 days, the awakening LD plasma level, i.e. LD plasma level before the next dose, should be at least 250 ng/mL, 275 ng/mL, 285 ng/mL, 290 ng/mL, 300 ng/mL, 310, ng/mL, 320 ng/mL or 330 ng/mL and the awakening CD plasma level should be at least 40 ng/mL, 45 ng/mL, 50 ng/mL, 55 ng/mL, 60 ng/mL, 65, ng/mL, 70 ng/mL or 75 ng/mL.

The dosing regimen of the present invention allows the second and third target patient populations to experience improved therapeutic benefits six, seven or eight hours after dosing and before the next dose compared to the patient's symptoms without the administration of the controlled release forms of described herein or compared to treatment with an immediate release CD-LD oral dosage form. An improved therapeutic benefit may be:

(i) an improvement or increase of at least 10%, 15%, 20%, 25%, 30%, 35%, 40%, 45% or 50% in the patient's motor state as determined by a qualified clinician;

(ii) an improvement or increase of at least 10%, 15%, 20%, 25%, 30%, 35%, 40%, 45% or 50% in the patient's motor state as determined by a patient's PD diary;

(iii) an improvement or increase of at least 10%, 15%, 20%, 25%, 30%, 35%, 40%, 45% or 50% in the subjects tremor, dyskinesia and/or mobility as measured by a Kinesia 360 Sensor;

(iv) a reduction of the MDS-UPDRS scores by 2, 3, 4, 5, 6, 7, 8, 9, 10, 11, 12, 13, 14, 15, 16, 17, 18, 19 20 or more points;

(v) an increase of at least 10%, 15%, 20%, 25%, 30%, 35%, 40%, 45% or 50% in the subject's total "On" time per day or during waking hours compared to a comparable total immediate release CD-LD doses per day or per waking hours;

(vi) an increase of at least 10%, 15%, 20%, 25%, 30%, 35%, 40%, 45% or 50% in the patient's total "Good On" time per day or during waking hours compared to a comparable total immediate release CD-LD doses per day or per waking hours;

(vii) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "On" time per dose, per day and/or during waking hours per day compared to a comparable oral dose of an immediate release CD-LD dosage form or the total immediate release CD-LD doses per day or per waking hours;

(viii) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "Good On" time per dose, per day and/or during waking hours per day compared to a comparable oral dose of an immediate release CD-LD dosage form or the total immediate release CD-LD doses per day or per waking hours;

(ix) a decrease of at least 10%, 15%, 20%, 25%, 30%, 35%, 40%, 45% or 50% in the patient's total "Off" time per day or during waking hours compared to a comparable total immediate release CD-LD doses per day or per waking hours;

(x) a decrease of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer of the patient's "Off" time per dose, per day and/or during waking hours per day compared to a comparable oral dose of an immediate release CD-LD dosage form or the total immediate release CD-LD doses per day or per waking hours (xi) an increase of at least 10%, 15%, 20%, 25%, 30%, 35%, 40%, 45% or 50% in the patient's PGI-C score, CGI-C score and/or PDQ-39 score compared to a comparable oral dose of an immediate release CD-LD dosage form or the total immediate release CD-LD doses per day or per waking hours;

(xii) a decrease of at least 10%, 15%, 20%, 25%, 30%, 35%, 40%, 45% or 50% in the average number of motor fluctuations per day compared to a comparable oral dose of an immediate release CD-LD dosage form or the total immediate release CD-LD doses per day or per waking hours;

(xiii) a decrease of at least 10%, 15%, 20%, 25%, 30%, 35%, 40%, 45% or 50% in the perceptual problems and/or hallucinations per day compared to a comparable oral dose of an immediate release CD-LD dosage form or the total immediate release CD-LD doses per day or per waking hours; or (xiv) any combination of the foregoing.

In certain embodiments the improved therapeutic benefit includes at least 10%, 15%, 20%, 25%, 30%, 35%, 40%, 45% or 50% improvement in MDS-UPDRS Part III scores.

The dosing regimen for the second and third target patient populations comprising orally administering to the patient the controlled release dosage forms described herein every 6 to 12 hours, every 6 to 9 hours, most preferably about every 7 to 8 hours will control or manage the patient's motor fluctuations symptoms and in certain embodiments will also reduce the patient's total "Off" time during in a 24 hour period to less than about 5 hours, less than about 4 hours, less than about 3 hours, less than about 2 hours, less than about 1 hour, less than about 0.5 hours, or any intermediate periods therein. The dosing regimen for the second and third target patient populations comprising orally administering to the subject the controlled release dosage forms described herein every 6 to 12 hours, preferably every 6 to 9 hours, most preferably about every 7 to 8 hours will control or manage the patient's motor fluctuations symptoms and in certain embodiments will also reduce the patient's total "Off" time during waking hours to less than 5 hours, less than 4 hours, less than 3 hours, less than 2 hours, less than 1 hour and less than 0.5 hours during waking hours in a 24 hour period.

The dosing regimen for the second or third target patient population comprising orally administering to the subject the controlled release dosage forms described herein every 6 to 12 hours, preferably every 6 to 9 hours, most preferably about every 7 to 8 hours will control or manage the patient's motor fluctuations symptoms and in certain embodiments will increase the patient's total "On" time to at least about 5 hours, e.g., more than 5 hours, more than 6 hours, more than 7 hours, more than 8 hours, more than 9 hours, more than 10 hours, or intermediate periods therein per day. The dosing regimen for the second or third target patient populations comprising orally administering to the subject the controlled release dosage forms described herein every 6 to 12 hours, preferably about every 6 to 9 hours, and most preferably about every 7 to 8 hours will control or manage the patient's motor fluctuations symptoms and in certain embodiments will also increase the patient's total "Good On" time to at least about 5 hours, e.g., more than 5 hours, more than 6 hours, more than 7 hours, more than 8 hours, more than 9 hours, more than 10 hours, or intermediate periods therein, per day.

The dosing regimen for the second or third target patient population comprising orally administering to the patient the controlled release dosage forms described herein every 6 to 12 hours, preferably every 6 to 9 hours, most preferably every 7 to 8 hours will control or manage the patient's motor fluctuations symptoms and in certain embodiments will increase the patient's total "On" time per dose, per day and/or during waking hours per day by at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes, intermediate periods therein or longer compared to a comparable oral administration of an immediate release CD-LD dose or the total immediate release CD-LD doses per day or waking hours per day. In certain aspects of this embodiment, the controlled release dosage forms are administered 2 to 3 times a day compared to the immediate release CD-LD dose administered 4 or 5 times a day. In certain aspects of this embodiment, the controlled release dosage forms are administered 3 times a day compared to the immediate release CD-LD dose administered 4 or 5 times a day.

The dosing regimen for the second or third target patient populations comprising orally administering to the patient the controlled release dosage forms described herein every 6 to 12 hours, preferably every 6 to 9 hours, most preferably every 7 to 8 hours will control or manage the patient's motor fluctuations symptoms and in certain embodiments will also increase the patient's total "Good On" time per dose, per day and/or during waking hours per day by at least 20, 25, 30, 35, 40, 45, 50, 55, 60, 65, 70, 75, 80, 85, 90, 95, 100, 105, 110,115, 120, 125, 130, 135, 140, 145, 150, 155, 160, 165, 170, 175 180 minutes or longer compared to a comparable oral administration of an immediate release CD-LD dose or the total immediate release CD-LD doses per day or per waking hours. In certain aspects of this embodiment, the controlled release dosage forms are administered 2 or 3 times a day compared to the immediate release CD-LD dose administered 4 or 5 times a day. In certain aspects of this embodiment, the controlled release dosage forms are administered 3 times a day compared to the immediate release CD-LD dose administered 4 or 5 times a day.

The dosing regimen for the second or third target patient populations comprising orally administering to the patient the controlled release dosage forms described herein every 6 to 12 hours, preferably about every 6 to 9 hours, most preferably every 7 to 8 hours will control or manage the patient's motor fluctuations symptoms and in certain embodiments will also decrease the patient's total "Off" time per dose, per day and/or during waking hours per day by at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes or longer compared to a comparable oral administration of an immediate release CD-LD dose or the total immediate release CD-LD doses per day or waking hours per day. In certain aspects of this embodiment, the controlled release dosage forms are administered 2 or 3 times a day compared to the immediate release CD-LD dose administered 4 or 5 times a day. In certain aspects of this embodiment, the controlled release dosage forms are administered 3 times a day compared to the immediate release CD-LD dose administered 4 or 5 times a day.

In certain embodiments the improved therapeutic benefits experienced by the PD patients in the first, second and/or third target patient populations may include a substantial reduction in total "Off" time during waking hours, which may range from about 12 to about 16 hours in a 24 hour period. As used herein substantial reduction in total "Off" time during waking hours may mean at least a 5%, 10%, 15%, 20%, 25%, 30%, 35%, 40% or 50% reduction in the total "Off" time during waking hours, which may be about 12-18, 13-17 or 14-16 hours during a 24 hour time period, compared to treatment with an immediate release CD-LD oral dosage form.

In certain embodiment the improved therapeutic benefits experienced by the PD patients in the first, second and/or third target patient populations may include a total "Off" time/dosing period of 240 minutes or less, 180 minutes or less, 160 minutes or less, 140 minutes or less, 120 minutes or less, 100 minutes or less, 90 minutes or less, 75 minutes or less, 60 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less, 0 minutes, or any intermediate periods therein. For the PD patients in the first target group the dosing interval is about every 8 to 12 hours. For the PD patients in the second and third target group the dosing interval may be 6-12 hours, preferably 7-9 hours and most preferably about 8 hours.

In certain embodiments the improved therapeutic benefits experienced by the PD patients in the first, second or third target patient populations may include a substantial increase in "On" and "Good On" time during waking hours, which may range from about 12 to about 18 hours or about 14 to about 16 hours in a 24 hour period. As used herein substantial increase in total "On" and "Good On" time during waking hours may mean at least a 5%, 10%, 15%, 20%, 25%, 30%, 35%, 40% or 50% increase in the total "On" or "Good On" time during waking hours (i.e., about 12-18, 13-17 or 14-16 hours during a 24 hour time period) compared to treatment with an immediate release CD-LD oral dosage form.

In certain embodiments the improved therapeutic benefits experienced by the PD patients in the first, second or third target patient populations may include a substantial increase in "On" and "Good On" time during waking hours, which may range from about 20, 25, 30, 35, 40, 45, 50, 55, 60, 65, 70, 75, 80, 85, 90, 95, 100, 105, 110, 115, 120,125, 130, 135, 140, 145, 150, 155, 160, 165, 170, 175 180 minutes or longer during the dosing time interval (i.e. per dose), compared to a comparable dose of an oral immediate release CD-LD dose or the total immediate release CD-LD doses per waking hours.

In certain embodiments the improved therapeutic benefits experienced by the PD patients in the first, second or third target patient populations may include a substantial decrease in "Off" time during waking hours, which may range from about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes or longer during the dosing time interval (i.e. per dose), compared to a comparable dose of an oral immediate release CD-LD composition during the waking hours.

In certain embodiments the improved therapeutic benefits experienced by the PD patients in the first, second or third target patient populations may include a substantial increase in "On" and "Good On" time during waking hours, for e.g., from about 12 to about 18 hours or about 14 to about 16 hours in a 24 hour period, with thrice daily administration of the controlled release dosage forms of the disclosure compared to five times daily administration of immediate release CD-LD oral dosage form. In certain embodiments the improved therapeutic benefits experienced by the PD patients in the first, second or third target patient populations may include a similar or improved LD pharmacokinetic parameter when the controlled release dosage forms described herein are: (i) administered under fed conditions and compared to an administration under fasting conditions; (ii) administered under fed conditions and compared to an administration under fasting conditions wherein the components of the controlled release dosage forms described herein are sprinkled onto a food substance such as yogurt or a fruit preparation, puree or compote and the sprinkled composition is administered; (iii) administered under fasting conditions and compared to an administration under fasting conditions wherein the components of the controlled release dosage forms described herein are sprinkled onto a food substance such as yogurt or a fruit preparation, puree or compote and the sprinkled composition is administered; or (iv) a combination of (i), (ii) and/or (iii). The similar or improved LD pharmacokinetic parameters include, but are not limited to, $C_{max}$ and $AUC_{0-t\ (ng\cdot h/mL)}$. A similar LD pharmacokinetic parameter as used herein means the geometric mean ratio of the target parameter value obtained from administration under fed or sprinkle conditions is within 80-120 of the target parameter value obtained from administration under fasting conditions. An improved LD pharmacokinetic value means the target parameter value obtained from administration under fed or sprinkle conditions exhibits a higher or larger value compared to the target parameter value obtained from administration under fasting conditions. For example, PD patients in the first, second or third target patient populations may take the controlled release dosage form as described herein with food and the LD $C_{max}$ and/or LD $AUC_{0-t\ (ng\cdot h/mL)}$ values will be at least 10%, 11%, 12%, 13%, 14%, 15%, 16%, 17%, 18% 19%, 20%, 21%, 22%, 23%, 24% or 25% or greater than the LD $C_{max}$ and/or LD $AUC_{0-t\ (ng\cdot h/mL)}$ values obtained when the same amount of the controlled release dosage form is administered under fasting conditions, preferably after at least ten hours of fasting and more preferably after an overnight fasting.

In certain embodiments the improved therapeutic benefits experienced by the PD patients in the first, second or third target patient populations may include a change in the time to maximum LD and/or CD plasma concentration ($T_{max}$) of less than 6 hours when the controlled release dosage forms described herein are: (i) administered under fed conditions and compared to administration under fasting conditions; (ii) administered under fed conditions and compared to an administration under fasting conditions wherein the components of the controlled release dosage forms described herein are sprinkled onto a food substance such as yogurt or a fruit preparation, puree or compote and the sprinkled composition is administered; (iii) administered under fasting conditions and compared to an administration under fasting conditions wherein the components of the controlled release dosage forms described herein are sprinkled onto a food substance such as yogurt or a fruit preparation, puree or compote and the sprinkled composition is administered; or (iv) a combination of (i), (ii) and/or (iii). For example PD patients in the first, second or third target patient populations may take the controlled release dosage form as described herein with food and exhibit a change in LD $T_{max}$ and/or CD $T_{max}$, of less than 5 hour, less than 4.5 hours, less than 4.0 hours, less than 3.5 hours, less than 3.0 hours, less than 2.5 hours, less than 2.0 hours, less than 1.5 hours, less than 1.0 hours or less than 0.5 hours when compared to the $T_{max}$ obtained after administration of the same amount to the controlled release dosage form under fasting conditions, preferably after at least ten hours of fasting and more preferably after an overnight fast.

Dosage Forms

Dosage forms that are useful in the dosing regimen of the present invention are controlled release oral solid formulations of LD and provide a relatively steady LD plasma or serum concentration profile over a prolonged period of time and enhancing absorption of the active agents in the gastrointestinal tract of a subject.

The dosage forms may comprise at least two components: (i) a first component or immediate release component that provides immediate release of LD; and (ii) a second component or controlled release component that provides for a controlled or sustained release of LD. In certain embodiments, the second component or controlled release component comprises a core comprising LD that is mixed, coated or layered with a muco-adhesive material, preferably a muco-adhesive polymer and externally coated with an enteric material, preferably an enteric polymer. The second component or controlled release component may also contain a rate controlling material that will contribute to the controlled release of the LD. The rate controlling material may be part of the controlled release component. For example, the rate controlling material may be a rate controlling polymer applied to the drug containing core and as an undercoating to a coating or layer containing a muco-adhesive material or the rate controlling material may be mixed with the LD to form a controlled release matrix or controlled release core of the controlled release component. The second or controlled release component is essential to provide extended absorption, thereby providing prolonged and steady therapeutic coverage.

The oral dosage forms useful in the present invention may also comprise a decarboxylase inhibitor, such as CD. The decarboxylase inhibitor, such as CD, may be present in the first or immediate release LD component, the second or controlled release LD component or in both the first or immediate release LD component and second or controlled release LD component. The decarboxylase inhibitor, such as CD, may also be present in a component that is separate and distinct from the first or immediate release LD component and/or the second or controlled release LD component. More specifically, one embodiment of the controlled release extended absorption oral dosage form of the present invention may comprise: (i) a first or immediate release component comprising LD; and (ii) a second or controlled release component comprising LD. Another embodiment may comprise: (i) a first or immediate release component comprising LD and CD; and (ii) a second or controlled release component comprising LD. A further embodiment may comprise: (i) a first or immediate release component comprising LD; and (ii) a second or controlled release component comprising LD and CD. A still further embodiment may comprise: (i) a first or immediate release component comprising LD and CD; and (ii) a second or controlled release component comprising LD and CD. Another embodiment may comprise (i) a first or immediate release component comprising LD; and (ii) a second or controlled release component comprising LD. (iii) a third or immediate release component comprising CD; and/or (iv) a fourth or controlled release component comprising CD. The first, second, third and/or fourth components may be separate and distinct components or may be combined to form distinct parts or regions of a larger combined component.

In another embodiment, first or immediate release component may comprise a powder or granules comprising LD and/or CD and optionally one or more pharmaceutically acceptable excipients and the powder or granules are a separate and distinct composition from the second or controlled release component however, both may be incorporated into a capsule for administration to a patient.

In another embodiment, the first or immediate release component comprises immediate release granules comprising CD and LD with a disintegrant to allow for rapid dissolution.

Alternatively, the first or immediate release component may comprise a coating or layer comprising LD and/or CD and optionally one or more pharmaceutically acceptable excipients wherein the coating or layer is applied to or part of the second or controlled release component. In this alternative embodiment, the first or immediate release component is combined with the second or controlled release component to form a distinct part or component of the larger combined component. It will be appreciated by the skilled artisan that the location, structure and/or placement of the first or immediate release component with respect to the second or controlled release components in the final dosage form is not critical provided the first or immediate release component allows for the immediate release of the drug such as LD and/or CD following administration of the dosage form to a patient and the second or controlled release component has the controlled-release and/or muco-adhesive properties described herein.

In another embodiment, the first or immediate release component comprises immediate release granules comprising CD and LD with a disintegrant to allow for rapid dissolution; and the controlled release component comprises controlled release beads comprising LD coated with a sustained release/controlled release polymer to allow for slow release of the drug (e.g., LD), a mucoadhesive polymer to keep the beads adhered to the area of absorption longer and an enteric coating to prevent the beads from disintegrating too early in stomach.

In some embodiments, the controlled release component comprises a rate controlling material, which may be the same or different from the muco-adhesive material. The rate controlling material and/or the muco-adhesive material slows or prolongs the release of active agent(s) or drug(s) from the controlled release component, thereby further extending the release and absorption of drug(s), preferably LD and optionally CD. The controlled release component should release the drug(s) such as LD or CD over a four to ten hour period preferably a five to eight hour period.

The immediate release component should provide fast release of the drug(s) such as LD and CD and thereby a rapid absorption of the drug(s) such as LD and CD. The rapid absorption is important for PD patients in need of a fast "on." As a result, controlled release dosage forms useful in the present invention can provide LD plasma levels that rise quickly, preferably to therapeutic levels, and extend for a prolonged period of time.

In certain embodiments the amount of immediate release LD should range from about 10% to about 40% based on the total amount of LD in the oral dosage forms, preferably about 15% to 35%, and most preferably about 20%, 21%, 22%, 23%, 24%, 25%, 26%, 27%, 28% 29% or 30%.

Decarboxylase inhibitors such as CD are often provided with LD formulations in order to inhibit decarboxylation of LD, thereby increasing the LD bioavailability. In the controlled release dosage forms useful in the present invention, a decarboxylase inhibitor may be included in the immediate release component, the controlled release component, both the immediate release and controlled release component or in separate immediate release and/or controlled release components as described previously. Preferably, the decarboxylase inhibitor is CD and is included only in an immediate release form such as in the immediate release component with the LD or in a separate immediate release component from the LD. In alternative embodiments, the decarboxylase inhibitor, preferably CD, is included in both an immediate release form as previously described and a controlled release form such as in the controlled release component with the LD or in a separate controlled release component that does not contain LD. In the various embodiments the amount of immediate release decarboxylase inhibitor, preferably CD, should range from about 75% to about 100% based on the total amount of decarboxylase inhibitor in the oral dosage forms, preferably about 80% to 100%, and most preferably about 81%, 82%, 83%, 84%, 85%, 86%, 87%, 88%, 89%, 90%, 91%, 92%, 93%, 94%, 95%, 96%, 97%, 98%, 99% or 100%.

In one embodiment of the invention, the oral dosage forms comprise (1) one or more controlled release components comprising LD and (2) one or more immediate release components comprising LD. The one or more controlled release components may be formulated as a tablet, mini-tablet, bead, pellet, granule or combination thereof. The controlled release components may comprise a core containing LD coated with a layer comprising a muco-adhesive material or polymer and further coated with an outer layer comprising an enteric material or polymer. In certain embodiments, the drug-containing core of the controlled release component will comprises a rate controlling material, which may be mixed with the drug to form a controlled release matrix core, coated onto the drug containing core to form an undercoat below the coating or layer comprising the muco-adhesive material, incorporated into the coating or layer comprising the muco-adhesive material or polymer, or a combination thereof. In some embodiments, the controlled release material and muco-adhesive material may be mixed together with the LD to form a controlled release/muco-adhesive core.

The immediate release component may be formulated as a powder, coating, tablet, mini-tablet, bead, pellet, granule or combination thereof that is separate from or part of the controlled release component. In certain embodiments, the immediate release component is in the form of a powder, tablet, mini-tablet, pellet, bead or granule that is separate from the controlled release component. In alternative embodiments the immediate release component may also be applied as an immediate release coating or layer onto one or more of the controlled release components. In certain embodiments, the immediate release component may be applied to or surround the enteric coating of the controlled release component.

In another embodiment of the invention, the oral dosage forms comprise (1) one or more controlled release components comprising a LD and (2) one or more immediate release components comprising LD and (3) a decarboxylase inhibitor component, preferably a CD component. The decarboxylase inhibitor component may be formulated as a powder, coating, tablet, mini-tablet, bead, pellet, granule or combination thereof. The decarboxylase component may be in an immediate release form, a controlled release form or immediate release and controlled release forms. The decarboxylase inhibitor may be co-formulated with (1) one or more of the controlled release components comprising a LD and/or (2) with one or more of the immediate release components comprising LD. Alternatively the decarboxylase inhibitor may be formulated separately from the one or more controlled release components comprising a LD and/or the one or more immediate release components comprising LD.

The controlled release component may comprise drug-containing cores containing both LD and a decarboxylase inhibitor such as CD, or the LD may be in separate controlled release components from that containing the decarboxylase inhibitor. In one embodiment of the invention, the controlled release component comprises an LD-containing core free or substantially free of a decarboxylase inhibitor such as CD. In this embodiment, substantially free means 15% or less of the total amount of decarboxylase inhibitor in the dosage form is in the controlled release component(s), preferably 10% or less, 9% or less, 8% or less, 7% or less, 6% or less, 5% or less, 4% or less, 3% or less, 2% or less, or 1% or less. The immediate release component of this embodiment may comprise a combination of LD and a decarboxylase inhibitor. The LD may also be in a separate immediate release component from the decarboxylase inhibitor.

In a preferred embodiment of the invention, the oral dosage forms comprise (1) one or more controlled release components comprising LD and (2) one or more immediate release components comprising LD and CD. In this embodiment, the controlled release component may comprise a drug-containing core coated with a first layer comprising a rate controlling material or polymer, a second layer comprising a muco-adhesive material or polymer and an outer or third layer comprising an enteric material or polymer. Additional coatings or layers such as cosmetic coatings or non-functional coatings such as water soluble seal coatings can also be added to separate the core, first, second and/or third layers or to overcoat the third layer. These cosmetic or non-functional coatings may also be used to separate an immediate release component from the controlled release component as well as to apply or adhere an immediate release component to the controlled release component. As used herein a non-functional or cosmetic coating should dissolve within 30 minutes, 25 minutes, 20 minutes, 15 minutes, 10 minutes or 5 minutes when the composition with the non-functional or cosmetic coating as the outer most coating is placed in a USP dissolution apparatus, either a Type I or II with 500-900 ml of an aqueous media with a pH of 1-7. In accordance with the practice of the invention, the components of the invention may be obtained by any methods commonly used in the art such as blending, mixing, granulation and/or coating processes, including, but not limited to, wet-granulation, fluid bed granulation/coating, or extrusion/spheronization, as are well-known in the pharmaceutical arts. The compositions may also be formed with other conventional formulation techniques such as compression and/or slugging. In addition to drugs such as LD and CD, the controlled release components and/or the immediate release components may further contain conventional pharmaceutically acceptable excipients such as lubricants, fillers, binders, disintegrants, glidants, surfactants (sometimes referred to as wetting agents), pH adjusting agents, antioxidants or mixtures of the foregoing.

In an embodiment of the invention, the controlled release and/or immediate release components are multiparticulates that are encapsulated, preferably in a hard gelatin capsule. The multiparticulates may be in a form that can be sprinkled directly onto food or liquids for easy ingestion.

The active agents, such as CD and LD, may be combined and dispersed throughout the drug-containing core. In another embodiment, the active agents may be present in the center of the drug-containing core or layered/coated on an inert core such as a sugar sphere, microcrystalline cellulose sphere, glass sphere, plastic sphere or combination thereof.

In an embodiment of the invention, the oral dosage forms may comprise two or more controlled release components that release the drug(s) such as CD and LD, at different rates. In this embodiment, the oral dosage forms contain at least two controlled release components differing in type, number, thickness and/or composition of first coating comprising the rate controlling material, the second coating comprising the muco-adhesive material and/or the third coating comprising the enteric material.

The muco-adhesive material employed in the present invention may be a homogenous muco-adhesive material, i.e., a single type of muco-adhesive material or polymer, or may comprise multiple types of muco-adhesive materials and/or polymers. The muco-adhesive material or polymer may possess certain characteristics such as being hydrophilic, hydrophobic, cationic, anionic and/or biocompatible and include multiple hydrogen bonding groups, hydrophobic surfaces, positively charged groups and/or negatively charged groups for adhesion to a mucosal surface so that the controlled release component can be held, prolonged or slowed at the site of absorption, thereby allowing the release of the LD from the controlled release component at the desired absorption site and thereby increase bioavailability. Further, the muco-adhesive material or polymer may be natural, synthetic or from a biological source. Further still, the muco-adhesive material or polymer may be composed of a single polymer or a combination of two or more different polymers. In one embodiment, the polymers may range in size from 10,000 daltons to 1,000,000 daltons and more preferably 20,000 daltons to 200,000 daltons.

An example of a muco-adhesive polymer includes, but is not limited to, a basic methacrylate copolymer, such as an amino methacrylate copolymer. A preferred example of a methacrylate copolymer is a basic butylated methacrylate copolymer, an amino methacrylate copolymer, or aminoalkyl methacrylate copolymer, such as Eudragit® E100 (poly (butyl methacrylate-co-(2-dimethylaminoethyl) methacrylate-co-methyl methacrylate) 1:2:1; CAS number: 24938-16-7; Evonik Industries). EUDRAGIT® E100 is a cationic copolymer based on dimethylaminoethyl methacrylate, butyl methacrylate, and methyl methacrylate with a ratio of 2:1:1.

Other examples of muco-adhesive materials or polymers include, but are not limited to, a glyceride, steroidal detergent, polycarbophil (CAS Number 9003-97-8; Noveon® AA-1; Lubrizol Corp.), carbomer, cellulosics, chitosan, diethylaminodextran, diethylaminoethyldextran, polygalactosamine, polylysine, polyornithine, prolamine, polyimine, hyaluronic acid, sodium alginate, hydroxypropylcellulose (HPC), hydroxypropylmethylcellulose (HPMC), sodium carboxymethylcellulose (sodium CMC) and alginate or combination thereof.

The muco-adhesive material or polymer may constitute about 1-75% of the mass of the controlled release component, preferably about 2-70% of the mass of the controlled release component, most preferably about 3-50% of the mass of the controlled release component. Preferably, the muco-adhesive material or polymer is Eudragit® E 100 alone or combined with at least one additional muco-adhesive material. The muco-adhesive material or polymer percentages of mass stated above are based on a multiparticulate with a bead size between 0.8 to 1.2 mm. If the bead size is larger or smaller than 0.8 to 1.2 mm, the skilled artisan will understand that the mass percentage described above should be adjusted accordingly.

Alternatively, the muco-adhesive material or polymer is a material capable of forming a positive ionic charge at the pHs present in the human gastro-intestinal tract. It is believed that the positive charge may allow the muco-adhesive material to interact with the negative charge of the intestinal walls and thereby slow or delay the gastrointestinal transit time of the controlled release component.

Enteric coating materials or polymers are known in the art. In general, enteric coating polymers are designed to prevent drug release from an oral solid dosage form in the low pH environment of the stomach, thereby delaying drug release until the dosage form reaches the small intestine. As such, the controlled release components of the invention have an in vitro release profile with minimal release of the active agent at pH 1.0. In the controlled release formulations of the invention, it is believed the second, third or outer enteric coating layer provides an additional advantage in preventing agglomeration of the controlled release components. That is, the enteric coat layer prevents the controlled release muco-adhesive components from sticking together in the low pH environment of the stomach.

The preferred enteric materials are shellac (esters of aleurtic acid), zein, cellulose acetate phthalate (CAP), poly (methacrylic acid-co-methyl methacrylate), poly(methacrylic acid-co-ethyl methacrylate), cellulose acetate trimellitate (CAT), poly(vinyl acetate phthalate) (PVAP), hydroxypropyl methylcellulose phthalate (HPMCP) and hydroxypropyl methylcellulose acetate succinates. The preferred enteric polymers release at a pH of greater than or equal to pH 5.5. Examples include Eudragit® L100 or Eudragit® L100-55. The enteric polymers may constitute about 1-40% of the mass of the controlled release component, preferably about 1.5-30%, most preferably about 1.5-25%. The enteric-coated polymer percentages stated above are based on a multiparticulate bead size between 0.8-1.2 mm. If the bead size is smaller or larger, the skilled artisan will understand that the mass percentage described above should be adjusted accordingly.

The second, third or outer enteric coating should be designed to dissolve at a pH greater than 5.0, at a pH of 5.5 or higher, at a pH of 6.0 or higher or a pH of 6.5 or higher. In certain embodiments, the second, third or outer enteric coating should be designed to dissolve at a pH in the range of 5.0 to 6.4, preferably in the range of 5.0 to 6.0.

The enteric coating polymer may comprise a methacrylic acid copolymer or multiple types of methacrylic acid copolymers. The methacrylic copolymer may comprise any of Eudragit® L 30 D-55 (poly(methacrylic acid-co-ethyl acrylate) 1:1; Eudragit® L 100-55 (poly(methacrylic acid-co-ethyl acrylate) 1:1; Eudragit® L 100 (poly(methacrylic acid-co-methyl methacrylate), Eudragit® L 12,5 (poly (methacrylic acid-co-methyl methacrylate); Eudragit® S 100 (poly(methacrylic acid-co-methyl methacrylate) 1:2; Eudragit® S 12,5 (poly(methacrylic acid-co-methyl methacrylate) 1 and Eudragit® FS 30 D (poly(methyl acrylate-co-methyl methacrylate-co-methacrylic acid) 7:3:1; or a combination thereof.

In a preferred embodiment of present invention, the controlled release component comprises a first rate controlling coating over the drug-containing core (i.e. applied to or surrounding the drug containing core with or without a seal coating), a second coating comprising a muco-adhesive material that is applied to or surrounding the rate controlling coating (with or without a seal coating) and a third coating comprising an enteric material that is applied to or surrounding the second coating (with or without a seal coating). The first rate controlling coating may comprise a controlled release material or polymer such as ethylcellulose, cellulose acetate, Eudragit® E, Eudragit® RS, Eudragit® RL, and Eudragit® NE, or mixtures thereof. Preferably, the controlled release materials are not soluble in water at neutral pH. Additional the controlled release materials or polymers that may be used are described in U.S. Pat. No. 5,002,776 which is incorporated herein by reference. In certain embodiments the controlled release material or polymer is cellulose acetate, ethylcellulose or a mixture thereof. The first or rate controlling coating may further comprise a pore forming agent or a flux enhancer to adjust the release rate of the drug from the core. Preferably, the pore forming agent or flux enhancer is a water soluble material such as a salt, i.e., NaCl, KCl, a sugar, i.e., lactose, sucrose, mannitol, povidone, copovidone, polyethylene glycol, hydroxypropyl cellulose, hydroxypropyl methylcelluose or combinations thereof. If the pore forming agent or flux enhancer is a water soluble polymer, it should have a low molecular weight such as below 100,000, preferably below 50,000 and/or should rapidly dissolve in water, i.e., 2 wt % of the water soluble polymer should dissolve in 100 ml of water within 15 minutes or less, preferably 10 minutes or less, and most preferably 5 minutes or less at 25° C.

The controlled release component may also comprise a hydrophobic controlled release material in addition to or in place of the controlled release materials described above. Examples of hydrophobic materials that can be used include beeswax, white wax, emulsifying wax, hydrogenated vegetable oil, hydrogenated castor oil, microcrystalline wax, cetyl alcohol, stearyl alcohol, free wax acids such as stearic acid, esters of wax acids, propylene glycol monostearate, glycerol monostearate, carnauba wax, palm wax, candelilla wax, lignite wax, ozokerite, ceresin wax, lardaceine, China wax and mixtures thereof. Other possible controlled release excipients useful in the present invention include saturated hydrocarbons having from 25 to 31 carbon atoms, saturated alcohols having from 25 to 31 carbon atoms, saturated monocarboxylic acids having from 25 to 31 carbon atoms, esters obtained from said alcohols, and monocarboxylic acids which are described in U.S. Pat. No. 6,923,984, incorporated herein by reference.

In an alternate embodiment, the controlled release component comprises a matrix core comprising a mixture of a controlled release material, which may be the afore-described controlled release materials and/or hydrophobic materials and the drug, i.e., CD and/or LD. The matrix core may further comprise one or more pharmaceutically acceptable excipients such as lubricants, fillers, binders, disintegrants, glidants, surfactants (sometimes referred to as wetting agents), pH adjusting agents, antioxidants or mixtures of the foregoing. In this embodiment, the matrix core may be further coated with a rate controlling coating or polymer before being coated with the muco-adhesive coating and the outer enteric coating.

In another alternate embodiment, the controlled release component may incorporate a controlled release material, which may be the afore-described controlled release materials and/or hydrophobic material, into the muco-adhesive coating. The muco-adhesive material may also function as the controlled release material or contribute to the controlled release of the drug form the controlled release component.

The controlled release material may constitute about 1-35% of the mass of the controlled release component, preferably about 2-30% and most preferably about 3-25%.

The muco-adhesive coating or layer and enteric coating or layer employed in the present invention may further comprise one or more pharmaceutically acceptable excipients such as plasticizers, lubricants, fillers, binders, disintegrants, glidants, surfactants (sometimes referred to as wetting agents), pH adjusting agents, antioxidants, or mixtures of the foregoing in addition to the muco-adhesive material and enteric material.

Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the *Encyclopedia of Polymer Science and Technology*, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and combinations thereof. Depending on the particular plasticizer, amounts from about 0% to about 25%, and preferably about 2% to about 15%, of the plasticizer can be used based upon the total weight of the controlled release, muco-adhesive and/or enteric coating.

Lubricants useful in pharmaceutical formulations are known in the art. Examples of a suitable lubricant include, but are not limited to, stearic acid, lauric acid, myristic acid, palmitic acid, fatty acid, magnesium stearate, calcium stearate, zinc stearate, sodium stearate, Stear-O-Wet®, sodium stearyl fumarate, salt of a fatty acid, metallic salt of fatty acid, glyceryl monostearate, glyceryl tribehenate, glyceryl dibehenate, Compritol® 888 ATO, glyceride ester, sorbitan monostearate, sucrose monopalmitate, sugar ester, fatty acid ester, talc, hydrated magnesium silicate, PEG 4000, boric acid, Carbowax (PEG) 4000/6000, sodium oleate, sodium benzoate, sodium acetate, sodium lauryl sulfate, magnesium lauryl sulfate, Sterotex, wax, or mixture thereof.

Examples of fillers that may be employed in the composition of the present invention include sugars, such as lactose, sucrose, mannitol, dibasic calcium phosphate, microcrystalline cellulose, calcium carbonate, magnesium carbonate, calcium sulfate, powdered cellulose, silicified microcrystalline cellulose, magnesium carbonate, magnesium oxide, starch, and mixtures thereof. The filler may constitute about 1-50% of the mass of the controlled release component, preferably about 2-45% and most preferably about 5-40%. Similarly, the filler may constitute about 1-50% of the mass of the immediate release component, preferably about 2-45% and most preferably about 5-40%.

Examples of binders that may be employed in the compositions of the present invention include acacia, povidone, hypromellose, hydroxypropyl cellulose, hydroxyethyl cellulose, polyethylene oxide, polymethacrylates, methyl cellulose, ethyl cellulose, pregelatinized starch, gelatin, tragacanth, zein, or mixtures thereof. Preferably, the binder is selected from povidone, hypromellose, hydroxypropyl cellulose, hydroxyethyl cellulose, polymethacrylates, methyl cellulose, gelatin and ethyl cellulose, or mixtures thereof. Especially preferred binders include water soluble binders such as povidone, hypromellose, hydroxypropyl cellulose, gelatin and mixtures thereof. The binder may constitute about 0.1-15% of the mass of the controlled release component, preferably about 0.2-10% and most preferably about 0.5-5%. The binder may constitute about 0.1-15% of the mass of the immediate release component, preferably about 0.2-10% and most preferably about 0.5-5%.

Examples of disintegrants that may be employed in the compositions of the present invention include croscarmellose sodium, starch, crospovidone, sodium starch glycolate, alginic acid, calcium carboxymethylcellulose, sodium carboxymethylcellulose, calcium carboxymethylcellulose, powdered cellulose, chitosan, guar gum, magnesium aluminum silicate, methylcellulose, sodium alginate, and mixtures thereof. The disintegrant may constitute about 0.1-15% of the mass of the immediate release component, preferably about 0.2-10% and most preferably about 0.5-5%.

Examples of glidants that may be employed in the compositions of the present invention include colloidal silicon dioxide, cornstarch, talc or mixtures thereof.

One or more surfactants may also be employed in the compositions of the present invention. The surfactant may be a non-ionic surfactant or an ionic surfactant. Examples of non-ionic surfactants include polyethoxylated castor oil, a polyoxyethylene alkyl ester, a polyglycolyzed glyceride, a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene_sorbitan fatty acid ester, a polyoxyethylene glycerin fatty acid ester, a polyoxyethylene hydrogenated castor oil, a polyoxypropylene fatty acid ester, or a mixture of the foregoing. A further listing of possible non-ionic surfactants can be found on pages 1243-1249 of Martindale, *The Extra Pharmacopoeia* 29$^{th}$ ed. which is incorporated herein by reference.

In certain embodiments, the non-ionic surfactants may comprise fatty alcohol acid or amide ethoxylates, monoglyceride ethoxylates, sorbitan ester ethoxylates alkyl polyglycosides, mixtures thereof, and the like. Certain non-ionic surfactants include polyoxyethylene derivatives of polyol esters, such as Polysorbate 20 (TWEEN 20®), Polysorbate 40 (TWEEN 40®) Polysorbate 60 (TWEEN 60®), and Polysorbate 80 (TWEEN 80®).

In certain embodiments, the non-ionic surfactant may also comprise d-alpha tocopheryl polyethylene glycol 1000 succinate (TPGS), nonoxinols, poloxamers, sorbitan monolaurate, sorbitan monooleate, sorbitan monopalmitate, sorbitan monostearate, sorbitan sesquioleate, sorbitan trioleate, tyloxapol, and mixtures of the foregoing.

Any variety of ionic surfactants may also be incorporated into the compositions of the present invention. Suitable ionic surfactants include, but are not limited to, carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, phosphates, quaternary ammonium salts, and ethoxylated amines. An example of a preferred ionic surfactant is sodium lauryl sulfate.

The surfactant may constitute about 0.1-15% of the mass of the controlled release component or the immediate release component, preferably about 0.2-10% and most preferably about 0.5-5%.

Examples of pH adjusting agents that may be employed in the compositions of the present invention include pharmaceutically acceptable acids or bases which may be present to adjust the pH of intermediate compositions leading up to the final compositions and to adjust the pH of the drug environment of final compositions to a desired or optimum pH range. Representative examples of pharmaceutically acceptable acids that may be used include, but are not limited to, acetic acid, citric acid, fumaric acid, hydrochloric acid, malic acid, nitric acid, phosphoric acid, propionic acid, sulfuric acid, tartaric acid, and mixtures thereof. Representative examples of pharmaceutically acceptable bases that may be used include but are not limited to ammonia, ammonium carbonate, diethanolamine, potassium hydroxide, sodium bicarbonate, sodium carbonate, sodium hydroxide, trolamine, and mixtures thereof. In certain embodiments the pH adjusting agent is an acid, preferably an organic acid and will constitute about 0.5-20% of the mass of the controlled release component, preferably about 0.75-15% and most preferably about 1-10%. Alternatively, the pH adjusting agent is an acid, preferably an organic acid and will be present in the controlled release component in a molar ratio of acid to levodopa of about 1:4 to about 4:1, preferably about 1:3 to about 3:1 and most preferably about 1:2 to about 2:1. Certain embodiments of the present invention, the immediate release components, the controlled release components and/or the final oral dosage forms are free or substantially free of a pH adjusting acid, preferably a pH adjusting organic acid and most preferably a pH adjusting carboxylic acid such as acetic acid, citric acid, fumaric acid, malic acid, propionic acid, tartaric acid, and mixtures thereof Examples of antioxidants that may be employed in the compositions of the present invention include ascorbic acid, ascorbyl palmitate, butylated hydroxyanisole, butylated hydroxytoluene, hypophosphorous acid, monothioglycerol, potassium metabisulfate, propyl gallate, sodium bisulfite, sodium formaldehyde sulfoxylate, sodium metabisulfate, sodium sulfate, sodium thiosulfate, sodium dioxide, tocopherol, and mixtures thereof.

In a preferred embodiment of the invention, the oral dosage forms comprise 1) one or more controlled release components comprising LD and (2) one or more immediate release components comprising LD and CD. The immediate release component comprises immediate release granules and the extended release component comprises extended release beads. The immediate-release granules comprise carbidopa and levodopa with a disintegrant polymer to allow for rapid dissolution. The extended release beads comprise levodopa, coated with a sustained-release polymer to allow for slow release of the drug, a mucoadhesive polymer to keep the beads adhered to the area of absorption longer and an enteric coating to prevent the beads from disintegrating too early in the stomach. The inactive ingredients are cellulose acetate, copovidone, croscarmellose sodium, amino methacrylate copolymer, methacrylic acid and methyl methacrylate copolymer, magnesium stearate, mannitol, microcrystalline cellulose, povidone, sodium lauryl sulfate, talc, and triethyl citrate In an embodiment of the invention, the CD and the LD are present in the dosage form of the invention in a weight ratio of about 1:1 to about 1:10, preferably about 1:3 to about 1:5 and most preferably about 1:4. Certain embodiments comprise CD and LD in a ratio of about 1:4 and wherein all or substantially all of the CD is in the immediate release component.

Examples of useful amounts of LD to CD include: (a) about 140 mg LD and about 35 mg of CD; (b) about 210 mg LD and about 52.5 mg of CD; (c) about 280 mg LD and about 70 mg of CD; and (d) about 350 mg LD and about 87.5 mg of CD. The foregoing values are based on the weight of anhydrous CD. If a monohydrate form of CD is employed the amounts will be slightly higher. For example, 35 mg of anhydrous CD is equivalent to 37.79 mg of CD monohydrate; similarly 70 mg of anhydrous CD is equivalent to 75.58 mg of CD monohydrate.

In an embodiment of the invention, the immediate release component may comprise less LD than the controlled release component. For example, the ratio of LD in the immediate release component to that in the controlled release component can be in the range of 0.15 to 0.49. For example, a ratio in weight of LD in the controlled release component:immediate release component is at least about 2:1, most preferably 3:1. Preferably the amount of LD in the immediate release component should provide a therapeutic dose of LD within one hour or less after administration of the dosage form, preferably within 45 minutes or less after administration and most preferably about 30 minutes or less after administration.

As discussed above, in certain embodiments comprising a decarboxylase inhibitor such as CD, all or substantially all of decarboxylase inhibitor should be in the immediate release component. The amount of immediate release decarboxylase inhibitor, preferably CD, in the immediate release component(s) should range from about 75% to about 100% based on the total amount of decarboxylase inhibitor in the oral dosage forms, preferably about 80% to 100%, and most preferably about 85%, 86%, 87%, 88%, 89%, 90%, 91%, 92%, 93%, 94%, 95%, 96%, 97%, 98%, 99 or 100%.

In one embodiment of the invention, the controlled release component comprise one or more, beads, pellets, tablets, mini-tablets or granules having a size that passes through 12, 14, or 16 mesh but may be retained on 18, 20 or 25 mesh screens. Further, the beads, pellets, tablets, mini-tablets or granules may have a size that passes through 14 mesh but may be retained on 18 or 25 mesh screens. In certain embodiments, the dosage forms of the invention comprise a plurality beads, pellets, tablets, mini-tablets or granules having a size that passes through 12, 14, or 16 mesh but may be retained on 18, 20 or 25 mesh screens.

The controlled release component will have an in vitro dissolution profile showing minimal release of the LD at pH 1.0 and extended release of the LD near neutral pH, for example minimal release may entail less than 20% release of LD, preferably less than 10%, most preferably less than 5% using United States Pharmacopeia (USP) I dissolution method at agitation speed of 75 rpm in Simulated Gastric Fluid (pH 1.0, without enzyme) for 2 hrs. Further, extended release may involve release at over at least four and up to an additional 8 hours at or near pH 7, upon changing to Simulated Intestinal Fluid (pH 7.0, without enzyme) after first 2 hrs. in Simulated Gastric Fluid (pH 1.0, without enzyme) using USP I dissolution method at agitation speed of 75 rpm. Further still, as used here, at or near pH 7 includes a pH at or about pH 6.5, 6.6, 6.7, 6.8 6.9, 7.1, 7.2, 7.3, 7.4, 7.5 or 7.6.

The oral controlled release dosage forms useful in the present invention should comprise one or more immediate release components and one or more controlled release components wherein following administration to a human patient the immediate release component(s) should provide a therapeutic dose of LD within one hour or less after administration of the dosage form, preferably within 45 minutes or less after administration and most preferably about 30 minutes or less after administration. To obtain this therapeutic level, the controlled release component(s) should exhibit the following in vitro release profiles when tested using a USP Type I or II apparatus, at 37° C., with a rotational speed of 75 rpms and 900 ml of an aqueous media with a pH between 6.8 and 7.4 and preferably at a pH of 7:

| | Levodopa Released | | |
|---|---|---|---|
| Time | Preferred | More Preferred | Most Preferred |
| 2 | 0-60% | 10-55% | 15-50% |
| 4 | 25-90% | 30-85% | 35-80% |
| 6 | 35-100% | 40-100% | 50-100% |

The amount of LD released in the above table is based on the total amount of LD present in the controlled release component(s). In certain embodiments the controlled release component(s) should also release less than 25% of the LD, preferably less than 20% and most preferably less than 15% when tested using a USP Type I or II apparatus, at 37° C., with a rotational speed of 75 rpms and 900 ml of an aqueous media with a pH of 1 for 2 hours.

In certain embodiments the oral controlled release dosage forms useful in the present invention comprises: (i) one or more immediate release components comprising LD and CD and (ii) one or more controlled release components, i.e., controlled release particles such as beads, pellets, tablets, mini-tablets, or granules comprising: (a) a core comprising LD, optionally CD and at least one pharmaceutically acceptable excipient, (b) a layer or coating surrounding the core comprising a muco-adhesive material and (c) an outer coating comprising an enteric material surrounding the muco-adhesive coating (b). This embodiment may also comprise a controlled release material in the core or a coating comprising a controlled release material surrounding the core and beneath the coating comprising the muco-adhesive material as well as cosmetic and/or non-functional seal coatings as previously described. When this embodiment of the dosage form of the present invention is tested using a USP Type I or Type II apparatus with 500-900 mL of an aqueous medium with a pH from about 1 to about 7.5, about 75% to 100% of the CD is released within 30 minutes, preferably about 85% to 100% of the CD is released within 30 minutes and most preferably about 90% to 100% of the CD is released within 30 minutes. In addition, when this embodiment of the dosage form is tested using a USP Type I or Type II apparatus and 500-900 mL of an aqueous medium with a pH from about 1 to about 4.0, about 15% to 45% of the LD is released within 30 minutes, preferably about 20% to 40% of the LD is released within 30 minutes and most preferably about 25% to 35% of the LD is released within 30 minutes. When this embodiment of the dosage form is tested using a USP Type I apparatus, at 37° C.±0.5° C., with a rotational speed of 75 rpms and 500-900 ml of simulated gastric fluid for 2 hours and pH 6.8 phosphate buffer thereafter the following LD in vitro profile is exhibited:

| | Levodopa Released | | |
|---|---|---|---|
| Time (hour) | Preferred | More Preferred | Most Preferred |
| 2 | 20-60% | 25-55% | 30-50% |
| 3 | 40-80% | 45-75% | 50-75% |
| 4 | 60-100% | 65-100% | 70-100% |
| 7 hours | NLT 80% | NLT 85% | NLT 90% |

NLT = Not Less Than.

In a further embodiment, the present invention comprises: a) one or more immediate release components as previously described; b) one or more controlled release components as previously described and c) one or more enteric coated components. The enteric coated component comprises a core comprising LD or ester of LD or salt thereof and/or a decarboxylase inhibitor and at least one pharmaceutically acceptable excipient as previously described and an enteric coating. The enteric coated component will release 100% of the LD and/or a decarboxylase inhibitor within 90 minutes, preferably 60 minutes and most preferably within 45 minutes when tested using a USP Type I or II apparatus, at 37° C., with a rotational speed of 75 rpms and 900 ml of an aqueous media with a pH between 6.8-7.4, preferably at pH 7. The enteric coated component will also release less than 25% of the LD, preferably less than 20% and most preferably less than 15% when tested using a USP Type I or II apparatus, at 37° C., with a rotational speed of 75 rpms and 900 ml of an aqueous media with a pH of 1.

The LD released from the controlled release component (s) may produce an in vivo LD a plasma profile (e.g., mean in vivo LD plasma profile) comprising a peak occurring not before about two hours after administration to a subject and provides at least three hour duration for LD plasma concentration above 50% the maximum value of the peak concentration ($C_{max}$). In another embodiment, in the plasma profile, the peak occurs after about one and a half hours after administration to the subject and exhibits at least a four-hour duration for LD plasma concentration at or above 50% of $C_{max}$. By way of example, the profile may be achieved under fasting conditions.

When the composition of the invention comprises an immediate release component and a controlled release component, the in vivo LD plasma profile following oral administration of the dosage form of the present invention to a subject may comprise a time of administration of an oral dosage form; an LD plasma concentration corresponding to $C_{max}$ occurring within about 6 hours or 7 hours after administration of the dosage form; a mean time to reach 50% of $C_{max}$ within one hour of administration, more preferably within 30 minutes. The time to 50% of $C_{max}$ is less than one hour and 50% of $C_{max}$ is maintained for at least 4 hours, e.g., about 4.5 hours or more. The time after administration of the dosage form when the maximum plasma concentration is reached ($T_{max}$) is between 30 minutes and 7 hours. Preferably, the LD plasma level is maintained at or above 50% of $C_{max}$ for at least about 4.5 hours, more preferably, for at least about 5 hours, even more preferably, for at least about 5.5 hours, and most preferably for at least about 7.0 hours.

In patients with Parkinson's disease, multiple-dose pharmacokinetics was comparable to single-dose pharmacokinetics, i.e., there was minimal accumulation of levodopa. When the composition of the invention comprises an immediate release component and a controlled release component, the in vivo LD plasma profile following oral administration of the dosage form of the present invention to a subject may comprise an LD fluctuation index that may range from 0.5 to 1.59, preferably about 0.7 to about 1.8 and more preferably about 1.7 compared to about 2.7 for immediate release CD-LD compositions. The fluctuation index can be determined the following formula $(C_{max}-C_{min})/C_{avg}$, wherein $C_{max}$ is the maximum or peak LD concentration, $C_m$ in the minimum LD concentration and $C_{avg}$ is the average LD concentration over the entire measurement interval. In certain embodiments, the fluctuation index is determined at steady state or about 10 to about 15 days after treatment with the formulations described herein and preferably is measured during the time period beginning from the first morning dose and 6, 7, 8, 9, 10, 11 or 12 hours after the first morning dose. In a preferred embodiment, variation in levodopa peak to trough plasma concentrations at steady-state defined as (Cmax−Cmin)/Cavg is about 1.7 for the combination composition compared to approximately 2.7 for immediate-release carbidopa-levodopa.

It is understood by those skilled in the art that the pharmacokinetic parameters recited herein may be obtained by single or multidose dose studies to healthy subjects or PD patients unless specifically stated. It is also understood that the pharmacokinetic parameters recited herein may be obtained under fed or fasting conditions. It is further understood that the pharmacokinetic parameters recited herein are mean values, unless specifically stated, obtained from single or multidose studies employing at least 3 or more subjects or patients.

The combination of immediate release components and controlled release components of the invention provide the near infusion-like profile. The LD $C_{max}$ itself is not clinically relevant. What is clinically relevant is the time to reach a therapeutic level of LD (e.g., an LD level of 50% $C_{max}$) and the time maintained at or above the therapeutic level (e.g., 50% $C_{max}$). The short time to reach a therapeutic LD level is associated with a faster "on" time for PD patients, whereas the prolonged period at or above therapeutic levels provides the desired steady "infusion-like" profile.

It is an advantage of the present invention to provide a sustained LD plasma concentration for a duration greater than 4.5 hrs. and a more consistent duration with percent coefficient of variation (CV) of mean duration of LD plasma concentrations >50% $C_{max}$ of less than 35%, preferably less than 30%.

Preferred Compositions of the Present Invention Include:

A multiparticulate composition comprising: a) one or more immediate release component(s) comprising LD and/or CD and optionally at least one pharmaceutically acceptable excipient as previously described and b) one or more controlled release component(s) comprising controlled release beads, pellets, tablets, mini-tablets, or granules wherein the beads, pellets, tablets, mini-tablets, or granules comprise a core of LD free or substantially free of CD and at least one pharmaceutically acceptable excipient as previously described, a muco-adhesive coating or layer applied to and/or surrounding the core and an enteric coating surrounding the muco-adhesive coating or layer wherein the controlled release beads, pellets, tablets, mini-tablets, or granules also comprises a controlled release material. The controlled release material may be: i) mixed with the LD to form a controlled release matrix core, ii) applied as a coating or layer onto the core comprising the LD and at least one pharmaceutically acceptable excipient; iii) incorporated or mixed into the muco-adhesive coating or layer or iv) a combination of (i), (ii) and/or (iii). Cosmetic and/or seal coatings as previously described may also employed in immediate release and controlled release components of this embodiment.

Alternative Preferred Compositions Includes:

A multiparticulate composition comprising: a) one or more immediate release component(s) comprising of LD, CD and optionally at least one pharmaceutically acceptable excipient as previously described; b) one or more controlled release component(s) free or substantially free of CD comprising beads, pellets, mini-tablets or granules wherein the beads, pellets, tablets, mini-tablets or granules comprise a core of LD and at least one pharmaceutically acceptable excipient as previously described, a muco-adhesive coating or layer applied to and/or surrounding the core and an enteric coating surrounding the muco-adhesive coating or layer wherein the controlled release beads, pellets, tablets, mini-tablets or granules also comprises a controlled release material and c) an enteric coated component comprising a plurality of enteric coated beads, pellets, mini-tablets or granules comprising a core comprising LD and/or a decarboxylase inhibitor and at least one pharmaceutically acceptable excipient as previously described and an enteric coating surrounding the core. The controlled release material employed in the controlled release component may be: i) mixed with the LD and at least one pharmaceutically acceptable excipient to form a controlled release matrix core, ii) applied as a coating or layer onto the core of the LD and at least one pharmaceutically acceptable excipient; iii) incorporated or mixed into the muco-adhesive coating or layer or iv) a combination of (i), (ii) and/or (iii).

In certain embodiments, the dosage forms that are useful in the dosing regimen of the present invention are described in U.S. Pat. No. 10,292,935 and U.S. Published Patent Application No. 2020/0009062 (U.S. Ser. No. 16/573,634 filed Sep. 17, 2019) which are incorporated herein by reference.

EXAMPLES

Example 1

Immediate release granules with the following composition were prepared:

|  | Wt % |
|---|---|
| Carbidopa USP* | 46.20 |
| Levodopa USP | 42.80 |
| Croscarmellose Sodium (AC-DI-SOL ®) | 7.00 |
| Povidone, USP (Plasdone K-29/32) | 3.00 |
| Magnesium Stearate | 1.00 |

*monohydrate

The granules were prepared mixing using the procedure similar to that described above in Example 5, preparation of Component 1 of U.S. Pat. No. 10,292,935 which is incorporated herein by reference. Generally, the CD, LD and croscarmellose sodium were mixed in a high shear granulator and wet granulated with a 5 wt % aqueous solution of povidone. After granulation, the wet granules were passed through a Comil with a 0.375 inch screen and dried in a fluidized bed. The dried granules were milled with a Fitzmill equipped with a 30 mesh screen then blended with magnesium stearate.

Example 2

Controlled release particles (beads) with the following composition were prepared:

|  | Wt % |
|---|---|
| Core | |
| Levodopa USP | 61.84 |
| Microcrystalline Cellulose, NF (Avicel PH-101) | 8.36 |
| Mannitol, USP (Mannogem ™ 2080 Granular) | 8.36 |
| Sodium Lauryl Sulfate | 4.18 |
| Povidone | 0.84 |
| Controlled Release Coating | |
| Cellulose acetate, NF (CA-398-10-NF) | 1.88 |
| Copovidone, NF (Kollidon VA64) | 2.30 |
| Muco-Adhesive Coating | |
| Amino-Methacrylic Acid Copolymer, NF (EUDRAGIT E100) | 6.38 |
| Talc | 0.64 |
| Enteric Coating | |
| Methacrylic Acid Copolymer, Type A, NF (EUDRAGIT L100) | 3.31 |
| Triethyl Citrate, NF | 0.95 |
| Talc, UPS | 0.47 |
| Blend | |
| Talc | 0.50 |

The controlled release beads were prepared by a process similar to that described in Example 5, Preparation of Component II of U.S. Pat. No. 10,292,935 which is incorporated herein by reference. Generally, the LD, microcrystalline cellulose, mannitol, and sodium lauryl sulfate were mixed in a high shear granulator and wet granulated with a 5 wt % aqueous solution of povidone. After granulation, the wet granules were extruded using an extruder equipped with a 0.9 mm hole size screen and the extrudate collected and loaded into a spheronizer equipped with a 3 mm cross hatch disc. The wet spheronized beads were dried in a fluidized bed drier. The dried beads were sieved through 16 market grade (MG) and 24 MG mesh screens and the beads passing through the 16 MG screen but remaining on the 24 MG screen were collected.

The collected beads were coated with a solution comprising cellulose acetate, copovidone, acetone and isopropyl alcohol using a fluidized bed coating apparatus. After the target coating solution was applied, the controlled release coated beads were dried in the fluidized bed. The dried controlled release beads were sieved through 14 MG and 24 MG mesh screens and the beads remaining on the 24 MG screen were collected. The collected controlled release coated beads were coated with a muco-adhesive solution comprising Eudragit E100, talc, acetone and isopropyl alcohol in the fluidized bed. After the target muco-adhesive coating solution was applied to the controlled release coated beads, the muco-adhesive coated beads were dried in the fluidized bed. The dried muco-adhesive coated beads were coated with an enteric coating solution comprising Eudragit L 100, talc triethyl citrate, acetone and isopropyl alcohol in a fluidized bed. After the target enteric coating solution was applied to the muco-adhesive coated beads, the enteric coated beads were dried in the fluidized bed. The dried enteric coated beads were sieved through 14 MG and 24 MG mesh screens and the beads remaining on the 24 MG screen were collected. The collected beads were blended with talc.

Example 3

The immediate release component of Example 1 and the controlled release beads of Example 2 were blended to create a mixture with 67.49 wt % controlled release beads and 32.51% immediate release granules. The mixture was filled into hard gelatin capsules containing (a) 180 mg LD and 45 mg CD and (b) 270 mg LD and 67.5 mg CD. The CD weight is based on CD anhydrous.

Example 4

Controlled release particles (beads) with the following composition were prepared according to the procedure of Example 2:

|  | Wt % |
|---|---|
| Core | |
| Levodopa USP | 60.12 |
| Microcrystalline Cellulose, NF (Avicel PH-101) | 8.12 |
| Mannitol, USP (Mannogem ™ 2080 Granular) | 8.12 |
| Sodium Lauryl Sulfate | 4.06 |
| Povidone | 0.80 |
| Controlled Release Coating | |
| Cellulose acetate, NF (CA-398-10-NF) | 2.92 |
| Copovidone, NF (Kollidon VA64) | 3.57 |
| Muco-Adhesive Coating | |
| Amino-Methacrylic Acid Copolymer, NF (EUDRAGIT E100) | 6.38 |
| Talc | 0.64 |
| Enteric Coating | |
| Methacrylic Acid Copolymer, Type A, NF (EUDRAGIT L100) | 3.32 |
| Triethyl Citrate, NF | 0.95 |
| Talc, UPS | 0.47 |
| Blend | |
| Talc | 0.50 |

Example 5

The immediate release component of Example 1 and the controlled release beads of Example 4 were blended to create a mixture with 68.11 wt % controlled release beads and 31.89% immediate release granules. The mixture was filled into hard gelatin capsules containing (a) 180 mg LD and 45 mg CD and (b) 270 mg LD and 67.5 mg CD. The CD weight is based on CD anhydrous.

Example 6

Controlled release particles (beads) with the following composition were prepared according to the procedure of Example 2:

|  | Wt % |
|---|---|
| Core | |
| Levodopa USP | 61.83 |
| Microcrystalline Cellulose, NF (Avicel PH-101) | 8.36 |
| Mannitol, USP (Mannogem ™ 2080 Granular) | 8.36 |
| Sodium Lauryl Sulfate | 4.18 |
| Povidone | 0.84 |
| Controlled Release Coating | |
| Cellulose acetate, NF (CA-398-10-NF) | 1.88 |
| Copovidone, NF (Kollidon VA64) | 2.30 |
| Muco-Adhesive Coating | |
| Amino-Methacrylic Acid Copolymer, NF (EUDRAGIT E100) | 6.38 |
| Talc | 0.64 |
| Enteric Coating | |
| Methacrylic Acid Copolymer, Type A, NF (EUDRAGIT L100) | 3.31 |
| Triethyl Citrate, NF | 0.95 |
| Talc, UPS | 0.47 |
| Blend | |
| Talc | 0.50 |

Example 7

The immediate release component of Example 1 and the controlled release beads of Example 6 were blended to create a mixture with 67.5 wt % controlled release beads and 32.5% immediate release granules. The mixture was filled into hard gelatin capsules containing (a) 140 mg LD and 35 mg CD; (b) 210 mg LD and 52.5 mg CD; (c) 280 mg LD and 70 mg CD; and (d) 350 mg LD and 87.5 mg CD. The CD weight is based on CD anhydrous. These dosage forms contained approximately 25% of the total LD content in the immediate release component; 75% of the total LD content in the controlled release component and 100% of the total CD content in the immediate release component.

The 210 mg LD and 52.5 mg CD; 280 mg LD and 70 mg CD; and 350 mg LD and 87.5 mg CD capsules prepared in this Example were tested using a USP Type I apparatus, at 37° C.±0.5° C., with a rotational speed of 75 rpms and 900 ml of simulated gastric fluid for 2 hours and pH 6.8 phosphate buffer thereafter. The 140 mg LD and 35 mg CD capsules prepared in this Example were tested using a USP Type I apparatus, at 37° C.±0.5° C., with a rotational speed of 75 rpms and 900 ml of simulated gastric fluid for 2 hours and pH 6.8 phosphate buffer thereafter. The results of the in vitro dissolution testing were as follows:

| | Time (hour) | 140/35 mg | | 210/52.5 mg | | 280/70 mg | | 350/87.5 mg | |
|---|---|---|---|---|---|---|---|---|---|
| | | CD | LD | CD | LD | CD | LD | CD | LD |
| acid | 0.5 | 103 | 28 | 103 | 29 | 103 | 29 | 103 | 29 |
| | 2 | 103 | 40 | 103 | 41 | 103 | 42 | 103 | 42 |
| buffer | 3 | | 68 | | 61 | | 63 | | 67 |
| | 4 | | 85 | | 80 | | 81 | | 86 |

-continued

| Time (hour) | 140/35 mg | | 210/52.5 mg | | 280/70 mg | | 350/87.5 mg | |
|---|---|---|---|---|---|---|---|---|
| | CD | LD | CD | LD | CD | LD | CD | LD |
| 5 | | 94 | | 90 | | 92 | | 95 |
| 7 | | 97 | | 96 | | 97 | | 99 |
| 8 | | 97 | | 97 | | 98 | | 100 |
| 10 | | 97 | | 99 | | 98 | | 100 |

Example 8

The dosage forms described in Example 3 were administered to 28 subjects with advanced PD in a randomized, open-label, rater-blinded, multicenter, 2-treatment, 2-periods multiple-dose crossover study. The subjects were randomized into 1 of 2 dosing sequences receiving the compositions of Example 3 ("IPX203") and an immediate release CD-LD ("IR CD-LD") tablet commercially available under the tradename SINEMET® or a U.S. FDA AB rated generic product to SINEMET®. Subjects received treatment for 15 days, with a 1-week (±2 days) washout period between treatment periods.

The study consisted of four (4) clinical visits after screening. Day 1 of each treatment period (Visits 1 and 3) and Day 15 of each treatment period (Visits 2 and 4). Subjects could continue allowed non-CD-LD based PD medications throughout the study if dosing regimens had been stable for at least 4 weeks prior to Visit 1.

To be eligible for the study, subjects who were diagnosed with idiopathic PD at age ≥40 years were required to be currently receiving stable regimens of CD-LD and experiencing motor complications. Motor complications were defined as the subject experiencing daily "wearing-off" episodes with periods of bradykinesia and rigidity, and experiencing an "Off" state upon awakening on most morning by history Within 2 weeks following screening, on each of the 3 days prior to Visit 1, eligible subjects completed their PD and dosing diaries and wore Kinesia 360 sensors on the more affected side from immediately after waking until bedtime. Subjects were instructed to take their last dose of CD-LD no later than 10:00 PM on the evening prior to Visits 1 and 3. The first morning dose of study medication was administered at the study site at Visits 1 and 3 in each treatment period.

On Day 1 of each treatment period (Visit 1 and Visit 3), subjects arrived at the study site and received a single dose of study medication. Subjects randomized to receive IR CD-LD started with a single dose of their usual prestudy first morning IR CD-LD dose. Subjects randomized to receive the compositions of IPX203 started with a single dose based on their usual prestudy first morning IR CD-LD dose according to the guidance provided in the Table 2.

TABLE 2

| Prestudy Morning IR LD Dose (mg) | IR CD-LD LD (mg) (100 mg Tablets) | IPX203 LD (mg) (180 mg and 270 mg Capsules) |
|---|---|---|
| 100 | 100 (1 tablet) | 360 (180 mg × 2 capsules) |
| 150 | 150 (1.5 tablets) | 540 (270 mg × 2 capsules) |
| 200 | 200 (2 tablets) | 720 (270 mg × 2 capsules plus 180 mg × 1 capsule) |
| 250 | 250 (2.5 tablets) | 900 (270 mg × 2 capsules plus 180 mg × 2 capsules |

On Day 1 in the clinic, after taking the first study drug dose, if a subject experienced an "Off" state for ≥3 consecutive hours post dose, or otherwise by investigator discretion, the subject could receive rescue medication. A subject requiring rescue during the JR CD-LD treatment received a dose of JIR CD-LD that corresponded to his/her typical pretreatment regimen based on the subject's dosing diary. For rescue during the IPX203 treatment, a subject was to receive a dose of IPX203 that he/she would typically receive following their morning dose as described in Table 3.

TABLE 3

| Most Frequent Afternoon and Evening LD Unit Dose (mg) | IPX203 Regimen Post Morning Dose |
|---|---|
| 100-125 mg | 270 mg every 7 to 8 hours (270 mg × 1) |
| 150-175 mg | 450 mg every 7 to 8 hours (180 mg × 1 + 270 mg × 1) |
| 200-225 mg | 540 mg every 7 to 8 hours (270 mg × 2) |
| 250-275 mg | 720 mg every 7 to 8 hours (270 mg × 2 + 180 mg × 1) |
| 300 mg | 810 mg every 7 to 8 hours (270 mg × 3) |

Note:
A 100-mg unit dose of IR LD converts approximately to a 270-mg unit dose of IPX203

After Day 1 assessments were completed, the subject was discharged and advised to take the prescribed study drug according to their initial regimen as follows:

The initial dosing regimen of JR CD-LD was the same as the subject's stable prestudy regimen. If they were taking a single daily bedtime dose of controlled-release ("CR") CD-LD, either alone or in combination with JR CD-LD, the CR CD-LD dose was discontinued and substituted with a 1:1 milligram equivalent JR CD-LD dose. A bedtime dose was defined as a dose of CR CD-LD taken within 1 hour of the subject's normal nighttime sleep period.

The initial dosing regimen of IPX203 was according to the guidance provided in Table 3, which was based on each individual's prestudy IR CD-LD morning dose and daily dosing regimen. The dosing regimen for IPX203 was projected to be 3 times a day, approximately every 7 to 8 hours.

During days 1 through 9 of each treatment period, the investigator could adjust each subject's study medication if necessary to optimized efficacy, tolerability, and safety. The dosing regimen was required to be stable for the last 5 days of each treatment period (Days 10-14). On the Day 15 clinic visit, the subject received the same stable drug regimen that they had taken on Days 10-14.

Pharmacokinetic and efficacy/pharmacodynamics were assessed periodically in the clinic for up to 8 hours post dose on Day 1 of each treatment period (Visits 1 and 3), and for up to 10 hours on Day 15 of each treatment period (Visits 2 and 4) by qualified clinical staff who were blinded to dosing.

These assessments were made regardless of whether the subject had received rescue dose(s) on Day 1 or received additional doses on Day 15 according to their established stable dosing regimen. Additionally, subjects completed PD and dosing diaries, and used the Kinesia 360 sensors on the ankle and wrist of their more affected side immediately after waking on each of the 3 days prior to Visits 1, 2 and 4.

The primary parameter was the average percent "Off" time during waking hours based on subject PD diaries for the last 3 days collected at the end of each treatment period. Secondary efficacy parameters utilized additional data collected from the PD diaries; dyskinesia, mobility and tremor measures obtained from the Kinesia 360 sensors; and MDS-UPDRS scores collected predose on Day 15 of each treatment period.

Pharmacodynamics were also assessed using the Subject Motor Assessment and MDS-UPDRS Part III scores. Pharmacokinetic parameters were calculated from CD and LD plasma concentration-time profiles after each treatment. Safety was evaluated by reviewing reported adverse events, concomitant medications, vital signs, electrocardiograms ("ECGs"), clinical laboratory tests, physical examinations, Columbia-Suicide Severity Rating Scale ("C-SSRS"), and vital signs.

Inclusion Criteria:

All the following criteria had to be met for a potential subject to be enrolled in the study:

1. Male or female subjects diagnosed with idiopathic PD at age ≥40 year who are being chronically treated with stable regimens of CD-LD but experience motor complications. Idiopathic PD is defined by United Kingdom Parkinson's Disease Society Brain Bank Diagnostic Criteria. There are no known secondary causes (e.g., vascular, toxin or medication-induced, metabolic, or infections) for subject's Parkinsonism nor does subject have another neurodegenerative disorder with Parkinsonism symptoms (e.g., progressive supranuclear palsy, corticobasal degeneration, multiple-system atrophy).
2. Able to provide written informed consent and willing to sign HIPAA authorization prior to the conduct of any study-specific procedures.
3. Negative urine pregnancy test in female subjects of childbearing potential at screening.
4. Negative urine screen for drugs of abuse and alcohol breath test screening.
5. Hoehn and Yahr Stages 2, 3, or 4 (included in MDS-UPDRS Part III).
6. Agrees to use a medically acceptable method of contraception throughout the study and for 6 weeks after completing the study.
7. Montreal Cognitive Assessment (MoCA) score ≥24 at screening in "On" state.
8. For 4 weeks prior to screening, the subject experiences daily "wearing-off" episodes with periods of bradykinesia and rigidity, and experiences and "Off" state upon awakening on most mornings by history.
9. At Visit 1, review of the 3-day PD diary confirms the following: that the subject is able to properly complete the diary with valid entries; and that the subject has an average of at least 2.5 hours per day of "Off" time during the waking hours over the 3 days with at least 1.5 hours "Off" time on each day. Inability to properly complete the diary is indicated when more than 1 day of the diary is not returned or when more than 2 hours (4 half-hour periods) of one 24-hour diary day are missing.
10. Responsive CD-LD therapy and currently being treated on a stable regimen with CD-LD for at least 4 weeks prior to Visit 1 and:
    a. Requires 100 to 250 mg LD of IR CD-LD for the morning dose
    b. Requires a total daily dose of at least 400 mg LD of IR CD-LD
    c. Takes a maximum total daily dose of 1800 mg LD, comprising ID CD-LD alone or IR CD-LD in combination with a single daily bedtime dose of CR CD-LD
    d. Has a dosing frequency of 4 to 9 times daily of CD-LD
    e. Typically experiences an "On" response with the first dose of ID CD-LD of the day
    f. By history, efficacy of the first morning dose of IR CD-LD lasts less than 4 hours, typically wearing "Off" prior to next dose; or subject takes second dose of PD medications prior to 4 hours to avoid an "Off"."
11. Has not used doses of CR CD-LD apart form a single daily bedtime dose for at least 4 weeks prior to Visit 1.
12. Has not used any doses of RYTARY® (carbidopa and levodopa) extended-release capsules for the past 4 weeks prior to Visit 1.
13. At screening, the MDS-UPDRS Part III total score in the "Off" state is:
    a. At least 20 units
    b. At least 25% or 10 units greater in the "On" state.
14. At screening, the subject has predictable "Off" periods defined by a score of 1 or 2 on item #4.5 Complexity of Motor Fluctuations of the MDS-UPDRS Part IV B (Motor Fluctuations).
15. Has a score ≥1 on Item #4.3 (Time Spent in the "Off" State) of the MDS-UPDRS Part IV B at screening.
16. Hemoglobin level must be above the lower limits of the laboratory's normal reference range.
17. Able and willing to comply with the protocol, including completion of diaries and availability for all scheduled study visits and data and blood-sample collection times.

Selection of Doses

Initial doses of IPX203 were chosen based on previous PK data obtained with IPX203 and IR CD-LD in patient with advanced PD. IPX203 doses were intended to achieve peak LD concentrations that were comparable (with about 20%) to the subject's corresponding dose of IR CD-LD. It was estimated that a LD dose of approximately 270 to 360 mg from IPX203 would provide peak LD concentrations comparable to those of 100 mg LD from IR CD-LD.

The recommended first morning dose of IPX203 on Day 1 was based on the subject's prestudy IR CD-LD morning dose; a 100 mg unit dose of ID CD-LD converted to a 360 mg unit dose of IPX203 as described above in Table 2. Subsequent doses of IPX203 during the day were based on the subject's most frequent prestudy LD dose in the afternoon and evening (noon to bedtime) as described above in Table 3, which converted an LD 100 mg unit dose in IR CD-LD to LD 270 mg in IPX203 in a dose-proportional manner. This study allowed evaluation of IPX203 unit doses of 270 mg and 360 mg as alternative conversions for a 100 mg unit dose of IR CD-LD. The estimated IPX203 dosing regimen was 3 times a day, dosed approximately every 7 to 8 hours.

The initial IR CD-LD dosing regimen was the same as the subject's stable prestudy regimen (unless he/she was taking a single daily bedtime dose of CR CD-LD, either alone or in combination with IR CD-LD, in which case, the CR CD-LD dose was discontinued and substituted with a 1:1 mg equivalent IR CD-LD dose).

During the first 9 days of each treatment period, the investigators could adjust the IPX203 and IR CD-LD dose regimen for optimal efficacy, tolerability, and safety. Study drug regimens on Days 10 to 15 of each treatment period were to remain stable with no dose adjustments.

At each scheduled clinic visit (Days 1 and 15 of each treatment period), subjects arrived having fasted for at least 8 hours and having withheld study drug since 10 PM the previous evening (Visits 1 and 3) or for at least 5 hours (Visits 2 and 4). Coffee, tea, water and juice were allowed up to 1 hour prior to dosing. All study drugs were administered with 240 mL of room temperature water. Subjects were instructed to swallow the study drug intact without crushing or chewing. A low protein breakfast was served at the study site approximately 1 hour after dosing. Lunch was provided at least 4 hours later, and dinner could have been provided. Snacks were allowed, although not within ±1 hour of the morning dose.

There were no restrictions on meals during the at-home dosing phase between clinic visits.

The two treatment periods were separated by a washout period of approximately 1 week.

Blood samples (6 mL) were collected by direct venipuncture or IV catheter for measurement of LD and CD plasma concentrations at the following nominal times:

Day 1 of each treatment period: predose and 0.5, 1, 1.5, 2, 2.5, 3, 4, 5, 5.5, 6, 6.5, 7, 7.5 and 8 hours post dose.

Day 15 of each treatment period: predose and 0.5, 1, 1.5, 2, 2.5, 3, 3.5, 4, 4.5, 5, 6, 7, 8 and 10 hours postdose.

The subject completed the PD diary for the last 3 days before returning to the clinic at Visits 1, 2, and 4. Each entry in the diary indicated the subject's predominant motor state over succeeding 30 minutes as one of the following 5 states:

"Off"
"On" without dyskinesia
"On" with nontroublesome dyskinesia
"On" with troublesome dyskinesia
Asleep.

The motor states were defined as follows:

"On" is defined as the state when a subject's medication is providing benefit with regard to mobility, slowness and stiffness.

"Off" is defined as the state when the medication has worn off and is no longer providing benefit with regard to mobility, slowness, and stiffness.

Dyskinesia is defined as involuntary twisting, turning movements that are an effect of medication and occur during "On" time.

Nontroublesome dyskinesia does not interfere with function or cause meaningful discomfort.

Troublesome dyskinesia interferes with function or causes meaningful discomfort.

"Good On" is defined as "On" without dyskinesia plus "On" with nontroublesome dyskinesia.

The MDS-UPDRS scale comprises 4 parts: Part I (non-motor experience of daily living); Part II (motor experiences of daily living); Part III (real-time motor examination) and Part IV (motor complications). Parts I, II and IV are questionnaires that were completed by the subject and describe their respective experience over the last week. MDS-UPDRS Parts I, II, III and IV were administered at screening (while subjects were in the "On" state) and at predose on Day 15 for each treatment. MDS-UPDRS Part III was also administered at screening while subjects were in the "Off" state.

Subjects wore Kinesia 360 sensors on the wrist and ankle of their most affected side for the last 3 days before returning for Visits 1, 2 and 4. Subjects were instructed to wear the Kinesia 360 sensors immediately on awakening until they went to bed, except during showers, baths or swimming.

A qualified treatment-blinded rater (investigator or clinical staff trained in the assessment of motor state) conducted an Investigator Assessment of the Subject's Motor State at clinic visits at 1 hour and 0.5 hour predose, just before dosing and every half hour post dose through 8 hours on Day 1 and through 10 hours on Day 15. The subject's motor state was reported as one of the 5 states identified above and calculated "Good On".

MDS-UPDRS Part III was administered on Days 1 and 15 at predose and hourly up to 8 hours (Day 1) and 10 hours (Day 15) postdose. Part III comprises 18 items including speech, facial expressions, rigidity, finger tapping, hand movements, pronation-supination hand movements, toe tapping, leg agility, arising from chair, gait, freezing of gait, postural stability, posture, global spontaneity of movement, postural tremor of hands, kinetic tremor of hands, rest tremor amplitude (extremity, lip/jaw), and constancy of rest tremor, each scored on a 5-point normal-to-severe scale; it also includes dyskinesia impact questions.

All pharmacokinetic analyses were conducted following FDA 2003 guidance for bioavailability and bioequivalence studies.

Noncompartmental methods were used to estimate $T_{max}$, $C_{max}$, $AUC_t$, $AUC_\infty$, ke and t½, for LD and CD (Phoenix WinNonlin, Version 6.4.0). The extent of LD exposure on Day 1 between 0-2 hours, 2-8 hours and 8 hours extrapolated to infinity was assessed by estimating $AUC_{0-2}$, $AUC_{2-8}$ and $AUC_{8-\infty}$ respectively. Partial AUCs on Day 15 between 0 to 2 hours, and 2 to 10 hours ($AUC_{0-2}$ and $AUC_{2-10}$) were estimated. Additionally, the time for plasma LD concentration to reach 50% of $C_{max}$ and 430 ng/mL and the duration of LD plasma concentration above 50% of $C_{max}$ and above 430 ng/mL were estimated for each treatment using a linear interpolation between adjacent time points. Bioavailability was calculated as the arithmetic mean ratio of the dose-normalized $AUC_\infty$ values for IPX203 and IR CD-LD. Normalized IPX203 data is presented normalized to 280 mg LD and 70 mg CD and the normalized IR CD-LD is presented normalized to 100 mg LD and 25 mg CD. Accumulation calculated as the ration of $AUC_tau$ on Day 15 to $AUC_{tau}$ on Day 1, where tau (dosing interval) on Day 1 was assigned the same value as tau on Day 15. The fluctuation index was calculated as $(C_{max}-C_{min})/C_{avg}$ over 10 hours of pharmacokinetic assessment on Day 15.

The bioequivalence of IPX203 was assessed relative to the IR CD-LD reference treatment using a mixed-effect analysis of variance that included treatment, period, and sequence as fixed effects and subject-within-sequence as a random effect.

Parkinson's Disease Diary Data (Days 12-14)

The primary efficacy parameter for this study was the average percent "Off" time during waking hours based on subject PD diaries collected at the end of each treatment period. For each of the 3 days that subjects recorded diary data (Days 12-14), total "Off" time was calculated by summing the number of half-hour intervals in which "Off" was checked. Percent "Off" time was calculated as total "Off" time divided by the total time not asleep (i.e., waking hours). The average percent "Off" time for each subject was the mean of the 3 days percent "Off" time. The primary endpoint was compared between treatments using a mixed-effects ANOVA that included treatment, period, and sequence as fixed effects and subject-within-sequence as a random effect. Summary statistics (mean, SD, median, minimum, maximum) were presented, along with LS means difference, SD, p-value, and 95% CI. Average "Off" time during waking hours results were also presented categorically, with number (percent) of subjects by treatment.

Presentations for secondary PD parameters included summary statistics, categorical presentations, and ANOVA treatment comparisons (LS means difference, SD, p-value, and 95% CIS) for the following:

Average total times for each motor state

Average total "Off" and "Good On" times normalized for 16 waking hours (calculated as the proportion of hours in the specific state to waking hours multiplied by 16)

Average number of clinical (motor) fluctuations (defined as a change from "On" to "Off" or vice versa)

Average duration of "Good On" state and average duration of any "On" states.

In addition, results of several secondary parameters were summarized categorically by treatment and compared using Fisher's exact test:

Proportions of subjects in "On" or in "Off" state on awaking from nocturnal sleep Proportions of subjects with a reduction in "Off" time from baseline of at least 0.5, 1, 1.5, 2, 3, and 4 hours. The baseline "Off" time was the average "Off" time from the 3 days prior to Visit 1.

MDS-UPDRS Changes from Screening to Predose (Parts I, II, III, and IV) The mean MDS-UPDRS Parts I, II, III, IV, II+III, and total scores were summarized at screening (while subjects were in the "On" state) and at predose on Day 15 for each treatment. Mean MDS-UPDRS Part III scores were also summarized at screening while subjects were in the "Off" state. Day 15 predose scores for each MDS-UPDRS part were compared by treatment using a mixed-effects ANCOVA with treatment, period, sequence as fixed effects, baseline (screening) value as a covariate, and subject-within-sequence as random effect.

Results of individual MDS-UPDRS Part IV questions were also presented with summary statistics (absolute and change-from-screening values) and treatment comparisons using a similar ANCOVA. A categorical presentation showing proportions of subjects with each absolute or change score is also included.

Kinesia 360 Sensor Data

Kinesia 360 sensor data (tremor, dyskinesia, and mobility) were summarized by treatment using summary statistics and compared between treatments using a mixed-effects ANOVA with treatment, period, and sequence as fixed effects and subject-within-sequence as a random effect. The following parameters were reported:

Tremor—total wear time, total tremor time, percent tremor time (percent of total wear time), number (%) of subjects with tremor;

Dyskinesia—Dyskinesia time, percent dyskinesia time, number (%) of subjects with dyskinesia;

Mobility—Percent rest time, recent active (non-gait) time, percent gait time, percent total active time, percent arm swing during gait, wear time steps, steps per hour of wear time.

Investigator Assessment of Subject's Motor State (Days 1 and 15)

If a subject received rescue medication or discontinued the study assessments, all subsequent motor state assessments on Day I were assigned the value of "Off" for analysis.

Investigator assessments of the subject's motor state were summarized on Days 1 and 15 with summary statistics, categorical presentations, and ANOVA treatment comparisons (LS means difference, SD, p-value, and 95% CIS) for the following:

Total times for each motor state

Time to first "On" (any "On" state) and "Good On" state

In addition, results for several parameters were summarized categorically by treatment and compared using Fisher's exact test—proportion of subjects in the "Off" or "Good On" states by time point.

MDS-UPDRS Part III (Motor Examination)

MDS-UPDRS Part III scores were summarized by treatment at each time point (predose, and hourly from 1 to 8 hours postdose on Day 1, and predose and hourly from 1 to 10 hours postdose on Day 15). Postdose scores were compared by treatment using a mixed-effects analysis of covariance (ANCOVA) with treatment, period, sequence as fixed effects, baseline (Day 1 predose) value as covariate, and subject-within-sequence as random effect. The postdose average MDS-UPDRS Part III scores for Day 1 and Day 15 were also summarized and compared by treatment using a similar ANCOVA model. Predose scores were compared by treatment using a mixed-effects ANOVA with treatment, period, and sequence as fixed effects and subject-within-sequence as random effect.

Similarly, mean changes from Day 1 predose in MDS-UPDRS Part III scores on Days 1 and 15 were summarized at each hourly postdose time point and overall (across the entire assessment period) and compared by treatment using an ANCOVA model with treatment, period, and sequence as fixed effects, baseline (Day 1 predose) value as covariate, and subject-within-sequence as random effect.

Results for the bradykinesia questions of the MDS-UPDRS Part III scale (Questions 4 through 8 and 14) were summarized by treatment as mean change from Day1I predose at each assessment time and a postdose average. For questions 4 through 8, assessments were performed on both the left and right side; the left and right side scores were added together before analyses. Results were summarized as a total bradykinesia score and individually for each question. These data were compared by treatment using a mixed-effects ANCOVA with treatment, period, and sequence as fixed effects, baseline (Day 1 predose) value as covariate, and subject-within-sequence as random effect.

Mean duration of improvement in MDS-UPDRS Part III scores of at least 4, 7, and 13 units from Day 1 predose score was summarized by treatment on Days 1 and 15, and a categorical presentation of proportions of subjects with particular durations of effect were provided. Duration of effect was compared by treatment using a mixed-effects ANOVA with treatment, period, and sequence as fixed effects, and subject-within-sequence as random effect.

To determine the duration of effect, the midway point between 2 adjacent time points was used. For example, if a subject did not have 4 units of improvement from the predose MDS-UPDRS Part III assessment at the 1-hour postdose assessment, but had the improvement at the 2-hour post dose assessment, and lost the 4-unit improvement at the 3-hour assessment, the duration of effect was considered as hour using the interpolated time value.

The demographics of the subjects enrolled in the study were as follows:

|  | Randomized (N = 28) | Completers (N = 27) |
|---|---|---|
| Age (years) | 66.4 ± 10.1 | 65.9 ± 9.8 |
| Height (cm) | 169.7 ± 10.3 | 169.8 ± 10.4 |
| Weight (kg) | 83.0 ± 18.7 | 83.4 ± 18.9 |
| Body mass index (kg/m$^2$) | 28.9 ± 6.7 | 29.0 ± 6.8 |
| Gender, n (%) |  |  |
| Male | 16 (57.1%) | 16 (59.3%) |
| Female | 12 (42.9%) | 11 (40.7%) |
| Race, n (%) |  |  |
| White | 26 (92.9%) | 25 (92.6%) |
| Other[a] | 2 (7.1%) | 2 (7.4%) |

[a]One subject was African American, Caucasian, and Asian; one subject was Hispanic and American Indian.

The baseline disease characteristics and treatment history for the subjects in the study is as follows:

| Characteristic | Randomized (N = 28) | Completers (N = 27) |
|---|---|---|
| Age at PD onset (years) | 58.9 ± 11.8 | 58.4 ± 11.6 |
| Duration of PD (years) | 7.5 ± 4.8 | 7.5 ± 4.9 |
| Hoehn and Yahr score | 2.1 ± 0.4 | 2.1 ± 0.3 |
| Stage II, number of subjects (%) | 24 (85.7) | 24 (88.9) |
| Stage III, number of subjects (%) | 4 (14.3) | 3 (11.1) |
| MoCA score | 27.4 ± 1.8 | 27.5 ± 1.7 |
| MDS-UPDRS Part III score while "On" | 19.1 ± 6.4 | 19.3 ± 6.5 |
| MDS-UPDRS Part III score while "Off" | 42.5 ± 10.6 | 42.6 ± 10.8 |
| Total "Off" time (hours) (from subject diary) | 5.2 ± 1.8 | 5.2 ± 1.9 |
| Total Good "On" time = Total "On" without dyskinesia time-total "On" with nontroublesome dyskinesia time (hours) (from subject diary) | 9.9 ± 2.3 | 10.0 ± 2.3 |

Note:
Values are mean ± SD unless stated otherwise.

The prestudy distribution of daily LD doses by dosing frequency is shown in the following table:

| Prestudy Total LD daily dose (mg) | \multicolumn{5}{c}{Number (%) of Subjects (N = 27) Prestudy Dosing Frequency (/day)} | | | | |
|---|---|---|---|---|---|
|  | 3 (n = 2) | 4 (n = 17) | 5 (n = 5) | 6 (n = 2) | 7 (n = 1) | 9 (n = 1) |
| 400 (n = 5) |  | 5 (18.5) |  |  |  |  |
| 450-500 (n = 3) |  | 1 (3.7) | 2 (7.4) |  |  |  |
| 550-600 (n = 10) | 2 (7.4) | 7 (25.9) |  | 1 (3.7) |  |  |
| 650-800 (n = 4) |  | 3 (11.1) |  |  | 1 (3.7) |  |
| 850-1200 (n = 3) |  | 1 (3.7) | 1 (3.7) | 1 (3.7) |  |  |
| ≥1250 (n = 2) |  |  | 1 (3.7) |  |  | 1 (3.7) |

As shown in the above table, most of the subjects were receiving 4 IR CD-LD doses per day, with a total daily LD dose range of 400 to ≥1250 mg. The maximum total daily dose of LD was 1550 mg. In addition, 8 subjects were receiving a single dose of CR CD-LD 200 mg at bedtime.

On Day 1, the mean LD first dose was 159 mg for JR CD-LD and 573 mg for PX203 and prior to dosing on Day 1, the median LD plasma concentration was 43 ng/mL for JR CD-LD and 41 ng/mL for PX203. The pharmacokinetic values for Day 1 are summarized in the following tables.

LD Day 1 Primary Parameters were:

| Parameter | IPX203 | IR CD-LD |
|---|---|---|
| \multicolumn{3}{c}{All Dose Levels (N = 27)} | | |
|  | All Doses | All Doses |
| $C_{max}$ (ng/mL) | 2858 ± 1205 | 2173 ± 1241 |
| $T_{max}$ (h) | 2.0 (0.5-5.0) | 0.5 (0.5-2.0) |
| $t_{1/2}$ (h) | 1.7 ± 0.5 | 1.4 ± 0.3[a] |
| $AUC_t$ (ng · h/mL) | 12108 ± 5794 | 3748 ± 1819 |
| $AUC_\infty$ (ng · h/mL) | 13969 ± 7607 | 4308 ± 2123[a] |
| Bioavailability (%)[b] | 89 ± 22 | — |
| \multicolumn{3}{c}{Dose Level 1 (N = 8)} | | |
|  | 360 mg | 100 mg |
| $C_{max}$ (ng/mL) | 1952 ± 712 | 1446 ± 392 |
| $T_{max}$ (h) | 1.8 (1.5-2.0) | 0.5 (0.5-2.0) |
| $t_{1/2}$ (h) | 1.4 ± 0.4 | 1.2 ± 0.4 |
| $AUC_t$ (ng · h/mL) | 8010 ± 2554 | 2360 ± 329 |
| $AUC_\infty$ (ng · h/mL) | 8824 ± 2917 | 2700 ± 461 |
| Bioavailability (%)[b] | 90 ± 21 | — |
| \multicolumn{3}{c}{Dose Level 2 (N = 8)} | | |
|  | 540 mg | 150 mg |
| $C_{max}$ (ng/mL) | 2945 ± 1284 | 1931 ± 1300 |
| $T_{max}$ (h) | 2.3 (0.5-4.0) | 0.8 (0.5-2.0) |
| $t_{1/2}$ (h) | 1.8 ± 0.5 | 1.5 ± 0.2 |
| $AUC_t$ (ng · h/mL) | 12820 ± 7965 | 3485 ± 1565 |
| $AUC_\infty$ (ng · h/mL) | 15000 ± 10726 | 4057 ± 1958 |
| Bioavailability (%)[b] | 99 ± 24 | — |
| \multicolumn{3}{c}{Dose Level 3 (N = 9)} | | |
|  | 720 mg | 200 mg |
| $C_{max}$ (ng/mL) | 3279 ± 1139 | 2627 ± 1177 |
| $T_{max}$ (h) | 2.0 (1.0-5.0) | 1.0 (0.5-2.0) |
| $t_{1/2}$ (h) | 1.6 ± 0.5 | 1.5 ± 0.3 |
| $AUC_t$ (ng · h/mL) | 14459 ± 4708 | 4474 ± 1690 |
| $AUC_\infty$ (ng · h/mL) | 16859 ± 6321 | 5228 ± 1712 |
| Bioavailability (%)[b] | 84 ± 16 | — |

-continued

| Parameter | IPX203 | IR CD-LD |
|---|---|---|
| \multicolumn{3}{c}{Dose Level 4 (N = 2)} | | |
|  | 900 mg | 250 mg |
| $C_{max}$ (ng/mL) | 4235 ± 488 | 4010 ± 1655 |
| $T_{max}$ (h) | 1.5 (1.0-2.0) | 0.5 (0.5-0.5) |
| $t_{1/2}$ (h) | 2.2 ± 0.3 | 1.5 ± 0.2 |
| $AUC_t$ (ng · h/mL) | 15067 ± 192 | 7079 ± 1544 |

-continued

| Parameter | IPX203 | IR CD-LD |
|---|---|---|
| AUC$_\infty$ (ng · h/mL) | 17415 ± 909 | 8068 ± 2762 |
| Bioavailability (%)[b] | 63 ± 18 | — |

[a]N = 26.
[b]Relative to IR CD-LD.
Note:
Values are mean ± SD except T$_{max}$, which are median (min-max). Doses shown are of LD; CD and LD are present at a fixed ratio of 1:4 in each treatment. All dose levels refer to first dose of the day.

The mean levodopa plasma concentration profile on Day 1 before rescue treatment is shown in FIG. 1.

The LD Day 1 Secondary Parameters were:

| Parameter | IPX203 | IR CD-LD |
|---|---|---|
| | All Dose Levels (N = 27) | |
| | All Doses | All Doses |
| Duration > 50% C$_{max}$ (h) | 4.6 ± 1.2 | 1.5 ± 0.6 |
| Duration > 430 ng/mL (h) | 6.8 ± 09 | 2.8 ± 0.9 |
| Time to reach 50% C$_{max}$ (h) | 0.6 (0 0-1.9) | 0.3 (0.2-1.6) |
| Time to reach 430 ng/mL (h) | 0.2 (0.0-1.1) | 0.1 (0.0-1.6) |
| | Dose Level 1 (N = 8) | |
| | 360 mg | 100 mg |
| Duration > 50% C$_{max}$ (h) | 4.5 ± 1.1 | 1.3 ± 0.6 |
| Duration > 430 ng/mL (h) | 6.3 ± 1.0 | 2.2 ± 0.3 |
| Time to reach 50% C$_{max}$ (h) | 0.7 (0.3-1.4) | 0.3 (0.2-0.8) |
| Time to reach 430 ng/mL (h) | 0.3 (0.1-1.1) | 0.2 (0.1-0.8) |
| | Dose Level 2 (N = 8) | |
| | 540 mg | 150 mg |
| Duration > 50% C$_{max}$ (h) | 4.5 ± 1.4 | 1.7 ± 0.8 |
| Duration > 430 ng/mL (h) | 6.7 ± 0.8 | 2.8 ± 0.6 |
| Time to reach 50% C$_{max}$ (h) | 0.4 (0.0-1.9) | 0.3 (0.2-1.5) |
| Time to reach 430 ng/mL (h) | 0.2 (0.0-1.0) | 0.3 (0.0-1.3) |
| | Dose Level 3 (N = 9) | |
| | 720 mg | 200 mg |
| Duration > 50% C$_{max}$ (h) | 5.0 ± 0.9 | 1.5 ± 0.5 |
| Duration > 430 ng/mL (h) | 7.2 ± 0.7 | 3.1 ± 1.1 |
| Time to reach 50% C$_{max}$ (h) | 0.6 (0.3-1.0) | 0.3 (0.2-1.6) |
| Time to reach 430 ng/mL (h) | 0.1 (0.0-0.4) | 0.1 (0.0-1.6) |
| | Dose Level 4 (N = 2) | |
| | 900 mg | 250 mg |
| Duration > 50% C$_{max}$ (h) | 3.1 ± 0.9 | 1.1 ± 0.1 |
| Duration > 430 ng/mL (h) | 7.2 ± 1.0 | 4.1 ± 0.1 |
| Time to reach 50% C$_{max}$ (h) | 0.5 (0.3-0.7) | 0.2 (0.2-0.3) |
| Time to reach 430 ng/mL (h) | 0.3 (0.1-0.5) | 0.0 (0.0-0.1) |

Note:
Duration values are mean ± SD; time to reach values are median (min-max).

The Dose Normalized LD Parameters were:

| Parameter | IPX203 (N = 27) | IR CD-LD (N = 27) |
|---|---|---|
| C$_{max}$ (ng/mL) | 1425 ± 527 | 1367 ± 613 |
| AUC$_t$ (ng · h/mL) | 6037 ± 2648 | 2343 ± 761 |
| AUC$_\infty$ (ng · h/mL) | 6925 ± 3467 | 2716 ± 903[a] |

-continued

| Parameter | IPX203 (N = 27) | IR CD-LD (N = 27) |
|---|---|---|
| AUC$_{0-2}$ (ng · h/mL) | 1698 ± 792 | 1512 ± 661[a] |
| AUC$_{2-8}$ (ng · h/mL) | 4574 ± 2018 | 1124 ± 387[a] |

[a]N = 26. AUC$_\infty$ could not be calculated for Subject No. 110-008 due to insufficient data points.
Note:
Values are normalized to 100 mg LD for IR CD-LD and 280 mg LD for IPX203.
Values are mean ± SD.

Figure 2:
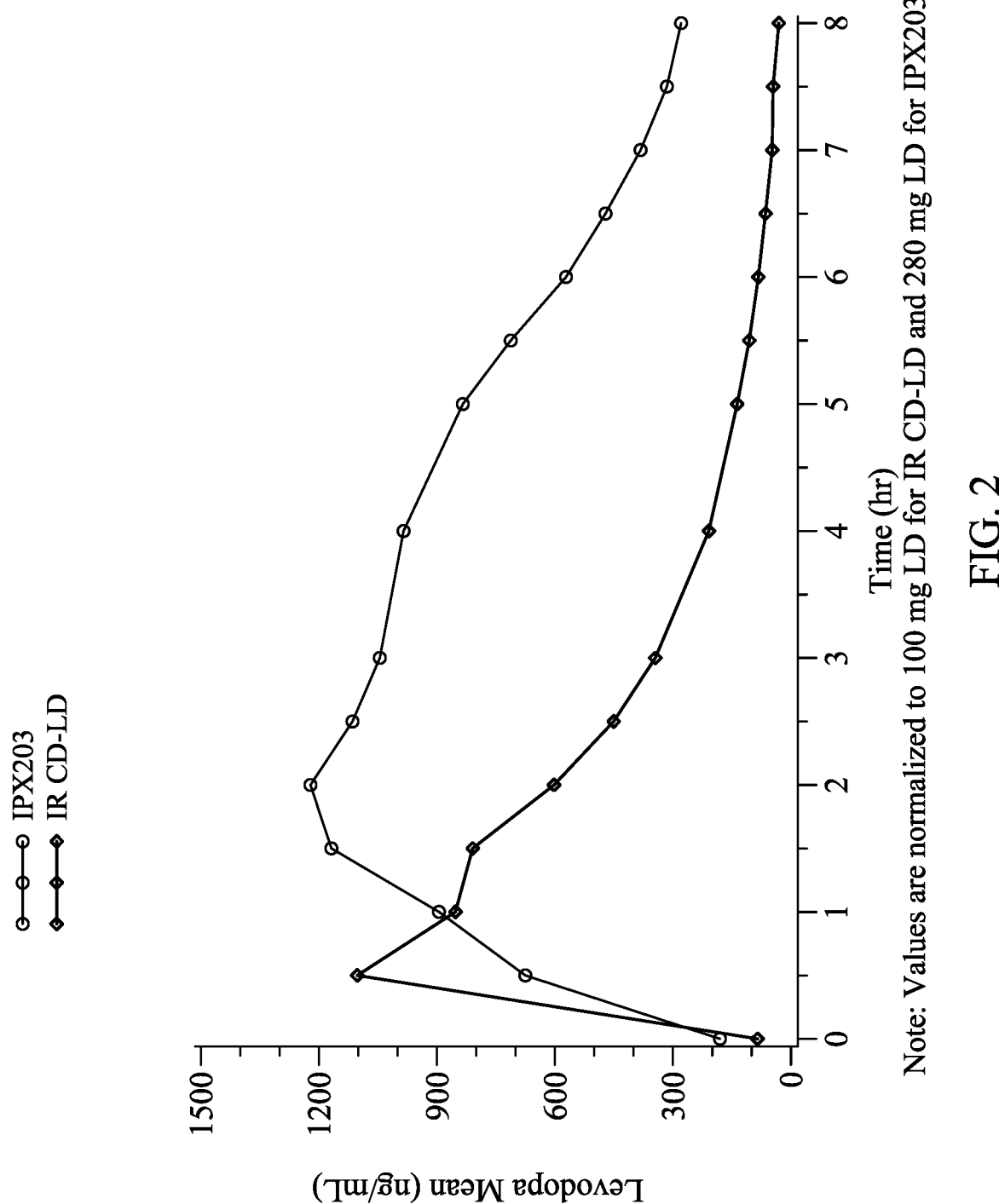
FIG. 2 shows the Day 1 dose normalized in vivo levodopa plasma profiles for the formulations tested in Example 8 under fasted conditions.

The mean dose normalized LD plasma concentration profile on Day 1 before rescue treatment is shown in FIG. 2.

The LD Partial AUC values were:

| | % Ratio of Geometric Mean Estimates (90% Confidence Interval) (N = 27) | | |
|---|---|---|---|
| Comparison | AUC$_{0-2}$ | AUC$_{2-8}$ | AUC$_{8-\infty}$ |
| IPX203/ IR CD-LD | 40.60 (36.54, 45.10)[a] | 142.65 (126.91, 160.35)[a] | 263.87 (194.59, 357.80)[b] |

[a]N = 26 since value could not be estimated reliably in 1 subject following IR CD-LD.
[b]N = 25 since value could not be estimated reliably in 1 subject following IR CD-LD and in 1 subject following IPX203.
Note:
Data reported are the ratios of the ln-transformed dose-normalized geometric means for Test/Reference expressed as a percentage and 90% CI. All data are normalized to 100 mg LD.

The CD Day 1 Primary Parameters were:

| Parameter | IPX203 | IR CD-LD |
|---|---|---|
| | All Doses, N = 27 | |
| C$_{max}$ (ng/mL) | 500 ± 316 | 152 ± 103 |
| T$_{max}$ (h) | 2.5 (1.5-4.0) | 2.0 (0.5-4.0) |
| t$_{1/2}$ (h) | 2.0-0.5[a] | 2.0 ± 0.7[b] |
| AUC$_t$ (ng · h/mL) | 1941 ± 1095 | 437 ± 286 |
| AUC$_\infty$ (ng · h/mL) | 2240 ± 1232[a] | 610 ± 407[b] |
| Bioavailability (%)[c] | 117 ± 43[d] | — |
| | Dose Level 1 (N = 8) | |
| | 90 mg | 25 mg |
| C$_{max}$ (ng/mL) | 208 ± 74 | 78 ± 37 |
| T$_{max}$ (h) | 2.3 (1.5-4.0) | 2.0 (0.5-3.0) |
| t$_{1/2}$ (h) | 2.2 ± 0.4 | 2.1 ± 1.4 |
| AUC$_t$ (ng · h/mL) | 834 ± 370 | 233 ± 90 |
| AUC$_\infty$ (ng · h/mL) | 985 ± 447 | 302 ± 124 |
| Bioavailability (%)[c] | 95 ± 45[e] | — |
| | Dose Level 2 (N = 8) | |
| | 135 mg | 37.5 mg |
| C$_{max}$ (ng/mL) | 403 ± 119 | 117 ± 68 |
| T$_{max}$ (h) | 2.8 (1.5-4.0) | 2.3 (1.5-2.5) |
| t$_{1/2}$ (h) | 2.2 ± 0.5[f] | 2.1 ± 0.3[f] |
| AUC$_t$ (ng · h/mL) | 1713 ± 424 | 382 ± 195 |
| AUC$_\infty$ (ng · h/mL) | 2027 ± 587[f] | 480 ± 214[f] |
| Bioavailability (%)[c] | 132 ± 32[g] | — |
| | Dose Level 3 (N = 9) | |
| | 180 mg | 50 mg |
| C$_{max}$ (ng/mL) | 768 ± 309 | 210 ± 88 |
| T$_{max}$ (h) | 2.5 (1.5-3.0) | 2.0 (1.5-4.0) |
| t$_{1/2}$ (h) | 1.8 ± 0.6 | 1.8 ± 0.4[g] |

-continued

| Parameter | IPX203 | IR CD-LD |
|---|---|---|
| $AUC_t$ (ng·h/mL) | 2840 ± 917 | 563 ± 308 |
| $AUC_\infty$ (ng·h/mL) | 3201 ± 950 | 814 ± 363[g] |
| Bioavailability (%)[c] | 123 ± 38[g] | — |
| Dose Level 4 (N = 2) | | |
| | 225 mg | 62.5 mg |
| $C_{max}$ (ng/mL) | 855 ± 205 | 316 ± 188 |
| $T_{max}$ (h) | 3.0 (3.0-3.0) | 2.5 (2.0-3.0) |
| $t_{1/2}$ (h) | 1.7 ± 0.1 | 1.8 ± 0.2 |
| $AUC_t$ (ng·h/mL) | 3229 ± 1197 | 903 ± 339 |
| $AUC_\infty$ (ng·h/mL) | 3677 ± 1382 | 1229 ± 729 |
| Bioavailability (%)[c] | 112 ± 98 | — |

[a]N = 26;
[b]N = 20;
[c]Relative to IR CD-LD;
[d]N = 19;
[e]N = 5;
[f]N = 7;
[g]N = 6

Figure 3:
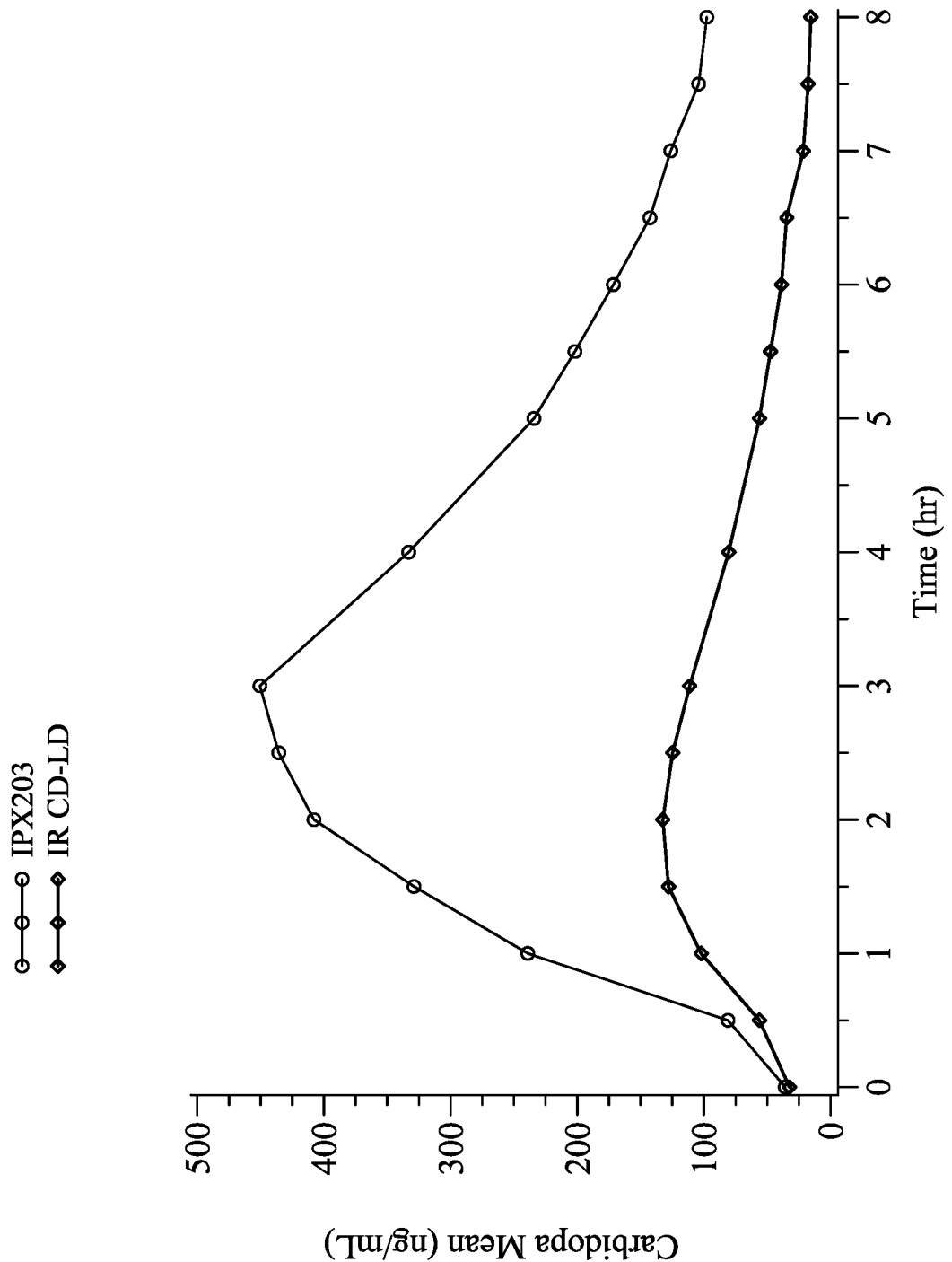
FIG. 3 shows the Day 1 in vivo carbidopa plasma profiles for the formulations tested in Example 8 under fasted conditions.

The mean CD plasma concentration profile on Day 1 before rescue treatment is shown in FIG. 3.

The CD dose normalized parameters were:

| Parameter | IPX203 (N = 27) | IR CD-LD (N = 27) |
|---|---|---|
| $C_{max}$ (ng/mL) | 229 ± 99 | 91 ± 45 |
| $AUC_t$ (ng·h/mL) | 898 ± 339 | 265 ± 126 |
| $AUC_\infty$ (ng·h/mL) | 1038 ± 384[a] | 359 ± 164[b] |

[a]N = 26;
[b]N = 20

Note:
Values are mean ± SD. PK parameters are normalized to 25 mg CD for IR CD-LD and 70 mg CD for IPX203.

On Day 15, the mean (±SD) LD administered in the clinic of a stable dosing regimen was 159±46.1 for JR CD-LD and 560±206.2 for IPX203 (first morning dose) and the median time to first redoes were 4.0 and 7.0 hours for JR CD-LD and IPX203 respectively. Prior to dosing on Day 15, the median LD plasma concentration was 34 ng/mL for JR CD-LD and 327 ng/mL for PX203.

Figure 4:
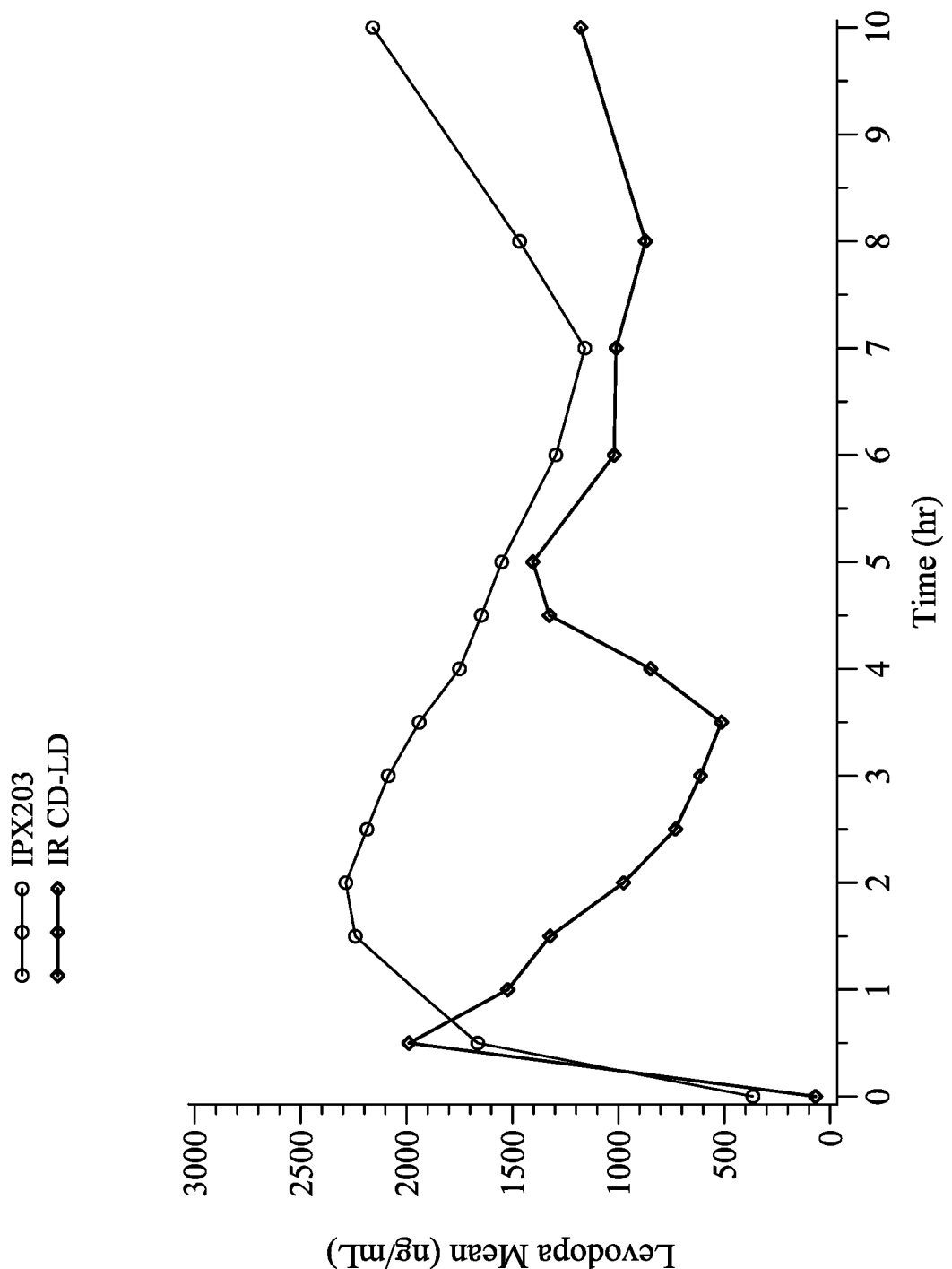
FIG. 4 shows the Day 15 in vivo levodopa plasma profiles for the formulations tested in Example 8.

The mean LD plasma profile following each treatment on Day 15 over the entire 10-hour assessment are shown in FIG. 4.

The pharmacokinetic values for Day 15 and summarized in the following tables:

LD Day 15 primary parameters were:

| Parameter | IPX203 | IR CD-LD |
|---|---|---|
| | (N = 27) | |
| | All Doses | All Doses |
| $C_{max}$ (ng/mL) | 2768 ± 1259 | 2357 ± 1179 |
| $T_{max}$ (h) | 1.5 (0.5-6.0) | 0.5 (0.5-2.0) |
| $AUC_{tau}$ (ng·h/mL) | 11214 ± 4887 | 3879 ± 1744 |
| Dose Level 1 (N = 7) | | |
| | 283 mg (mean) | 100 mg |
| $C_{max}$ (ng/mL) | 1468 ± 383 | 1217 ± 371 |
| $T_{max}$ (h) | 2.0 (0.5-4.0) | 1.0 (0.5-1.5) |
| $AUC_{tau}$ (ng·h/mL) | 6497 ± 1996 | 2362 ± 449 |
| Dose Level 2 (N = 10) | | |
| | 576 mg (mean) | 150 mg |
| $C_{max}$ (ng/mL) | 3116 ± 1281 | 2489 ± 1169 |
| $T_{max}$ (h) | 1.5 (0.5-6.0) | 0.5 (0.5-1.5) |
| $AUC_{tau}$ (ng·h/mL) | 12016 ± 4670 | 3862 ± 1916 |
| Dose Level 3 (N = 8) | | |
| | 698 mg (mean) | 200 mg |
| $C_{max}$ (ng/mL) | 3100 ± 1005 | 2730 ± 901 |
| $T_{max}$ (h) | 1.3 (0.5-3.0) | 0.8 (0.5-2.0) |
| $AUC_{tau}$ (ng·h/mL) | 13455 ± 4890 | 4662 ± 1376 |
| Dose Level 4 (N = 2) | | |
| | 900 mg (mean) | 250 mg |
| $C_{max}$ (ng/mL) | 4250 ± 382 | 4195 ± 417 |
| $T_{max}$ (h) | 2.3 (2.0-2.5) | 0.5 (0.5-0.5) |
| $AUC_{tau}$ (ng·h/mL) | 14748 ± 2466 | 6148 ± 549 |

Note:
Values are mean ± SD except $T_{max}$ which is median (min-max). Doses shown are of LD; CD and LD are present at a fixed ratio of 1:4 in each treatment. Subjects were grouped into dose levels (1-4) based on his/her LD dosage m the IR CD-LD treatment period (100, 150, 200, or 250 mg). The mean IPX203 LD dose for the first dose is provided for each dose level.

LD Day 15 secondary parameters were:

| Parameter | IPX203 | IR CD-LD |
|---|---|---|
| | (N = 27) | |
| | All Doses | All Doses |
| Duration > 50% $C_{max}$ (h) | 6.2 ± 1.9 | 3.9 ± 2.2 |
| Duration > 430 ng/mL (h) | 9.0 ± 1.3 | 7.4 ± 2.0 |
| Dose Level 1 (N = 7) | | |
| | 283 mg (mean) | 100 mg |
| Duration > 50% $C_{max}$ (h) | 5.6 ± 2.1 | 4.2 ± 2.1 |
| Duration > 430 ng/mL (h) | 7.7 ± 16 | 5.8 ± 1.8 |
| Dose Level 2 (N = 10) | | |
| | 576 mg (mean) | 150 mg |
| Duration > 50% $C_{max}$ (h) | 5.8 ± 1.5 | 3.9 ± 2.9 |
| Duration > 430 ng/mL (h) | 9.6 ± 0.7 | 7.8 ± 1.3 |
| Dose Level 3 (N = 8) | | |
| | 698 mg (mean) | 200 mg |
| Duration > 50% $C_{max}$ (h) | 6.9 ± 1.8 | 4.3 ± 1.2 |
| Duration > 430 ng/mL (h) | 9.6 ± 0.6 | 8.5 ± 1.9 |

| Parameter | IPX203 | IR CD-LD |
|---|---|---|
| Dose Level 4 (N = 2) | | |
| | 900 mg (mean) | 250 mg |
| Duration > 50% $C_{max}$ (h) | 6.7 ± 3.5 | 1.0 ± 0.0 |
| Duration > 430 ng/mL (h) | 8.8 ± 1.7 | 7.0 ± 4.1 |

Note:
Duration values are mean ± SD. Duration values are estimated over the entire available concentration-time profile (10 hours). Subjects were grouped into dose levels (1-4) based on his/her LD dosage in IR CD-LD in the IR CD-LD treatment period (100, 150, 200, or 250 mg). The mean IPX203 LD dose for the first dose is provided for each dose level.

The LD Day 15 dose normalized values were:

| | Mean + SD (N = 27) | |
|---|---|---|
| Parameter | IPX203 | IR CD-LD |
| $C_{max}$ (ng/mL) | 1410 ± 418 | 1459 ± 579 |
| $AUC_{tau}$ (ng · h/mL) | 5752 ± 1772 | 2439 ± 868 |

Note:
Values are normalized to 100 mg LD for IR CD-LD and 280 mg LD for IPX203

The LD accumulation, fluctuation and time invariance parameters were:

| | Mean ± SD (N = 27) | | |
|---|---|---|---|
| Treatment | Accumulation Ratio | Fluctuation Index | Time Invariance |
| IPX203 | 1.0 ± 0.3 | 1.7 ± 0.5 | 0.87 ± 0.3 |
| IR CD-LD | 1.1 ± 0.2[a] | 2.7 ± 1.0 | 0.93 ± 0.2[a] |

[a]N = 26

Note:
Accumulation ratio was calculated as the ratio of $AUC_{tau}$ on Day 15 to $AUC_{tau}$ on Day 1, where tau (dosing interval) on Day 1 was assigned the same value as tau on Day 15.
Fluctuation index was calculated as $(C_{max} - C_{min})/C_{avg}$ over the 10-hour assessment period.
Time-invariance was calculated as the ratio of $AUC_{tau}$ on Day 15 to $AUC_\infty$ on Day 1.

The CD Day 15 primary parameters were:

| Parameter | IPX203 | IR CD-LD |
|---|---|---|
| (N = 27) | | |
| | All Doses | All Doses |
| $C_{max}$ (ng/mL) | 479 ± 291 | 146 ± 83 |
| $T_{max}$ (h) | 2.5 (1.5-4.0) | 2.0 (1.5-4.0) |
| $AUC_{tau}$ (ng · h/mL) | 1892 ± 1018 | 416 ± 279 |
| Dose Level 1 (N = 7) | | |
| | 71 mg (mean) | 25 mg |
| $C_{max}$ (ng/mL) | 182 ± 75 | 62 ± 14 |
| $T_{max}$ (h) | 3.0 (1.5-4.0) | 2.0 (1.5-4.0) |
| $AUC_{tau}$ (ng · h/mL) | 843 ± 413 | 195 ± 91 |
| Dose Level 2 (N = 10) | | |
| | 143 mg (mean) | 37.5 mg |
| $C_{max}$ (ng/mL) | 576 ± 324 | 131 ± 57 |
| $T_{max}$ (h) | 2.3 (1.5-3.5) | 2.0 (1.5-3.0) |
| $AUC_{tau}$ (ng · h/mL) | 2218 ± 957 | 346 ± 133 |
| Dose Level 3 (N = 8) | | |
| | 174 mg (mean) | 50 mg |
| $C_{max}$ (ng/mL) | 522 ± 168 | 221 ± 76 |
| $T_{max}$ (h) | 2.5 (2.0-3.0) | 2.5 (2.0-3.5) |
| $AUC_{tau}$ (ng · h/mL) | 2094 ± 736 | 627 ± 354 |
| Dose Level 4 (N = 2) | | |
| | 225 mg (mean) | 62.5 mg |
| $C_{max}$ (ng/mL) | 862 ± 9.2 | 214 ± 28 |
| $T_{max}$ (h) | 2.8 (2.0-3.5) | 2.3 (2.0-2.5) |
| $AUC_{tau}$ (ng · h/mL) | 3129 ± 1304 | 691 ± 227 |

Note:
Values are mean ± SD except $T_{max}$ which are median (min-max). Doses shown are of CD; CD and LD are present at a fixed ratio of 1:4 in each treatment. Subjects were grouped into dose levels (1-4) based on his/her LD dosage in IR CD-LD in the IR CD-LD treatment period (100, 150, 200, or 250 mg). The mean IPX203 LD dose for the first dose is provided for each dose level.

Figure 5:
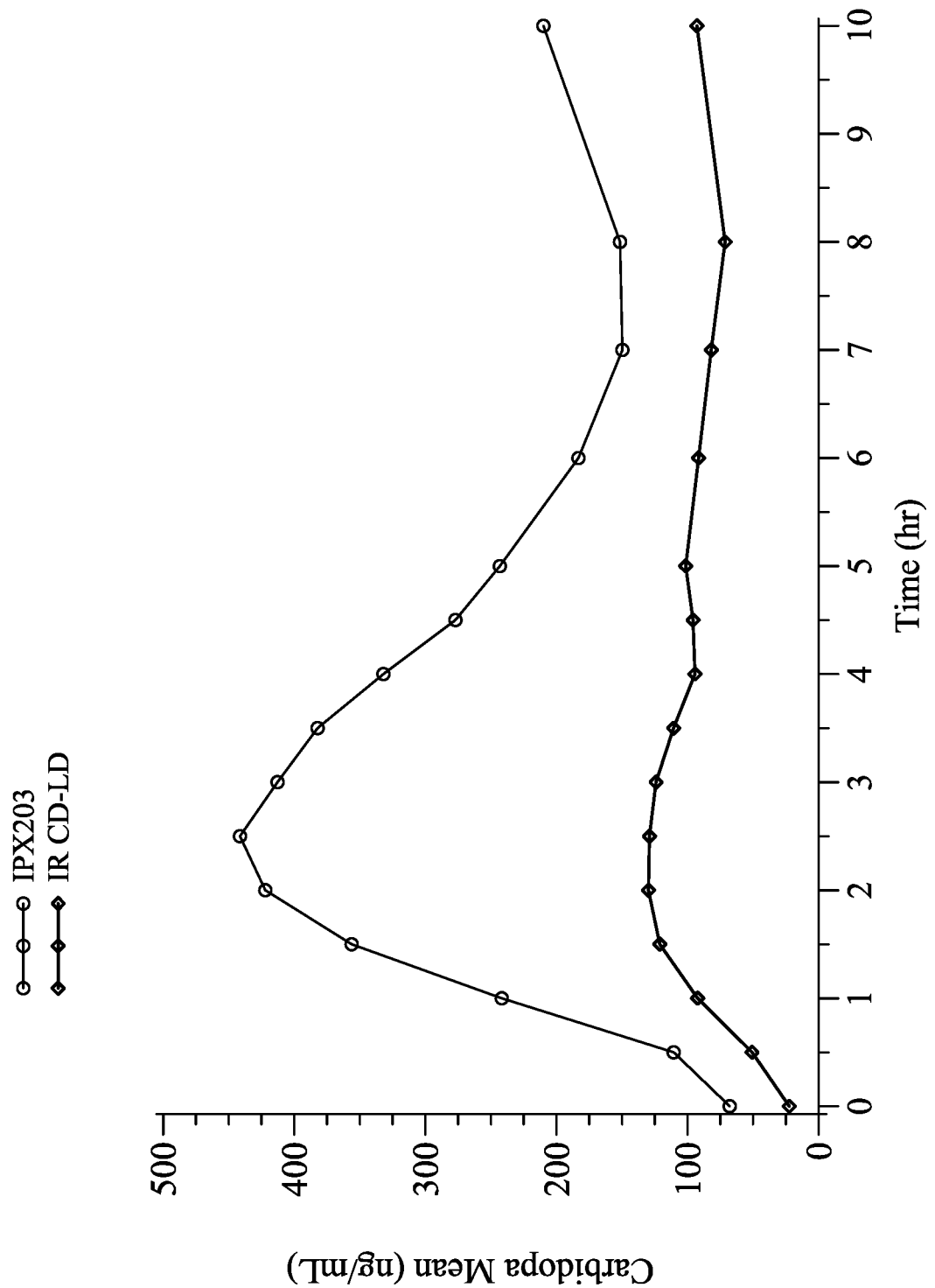
FIG. 5 shows the Day 15 in vivo carbidopa plasma profiles for the formulations tested in Example 8.

The mean CD plasma profile following each treatment on Day 15 over the entire 10-hour assessment are shown in FIG. 5.

The CD Day 15 dose normalized values were:

| | Mean ± SD (N = 27) | |
|---|---|---|
| Parameter | IPX203 | IR CD-LD |
| $C_{max}$ (ng/mL) | 227 ± 86 | 87 ± 36 |
| $AUC_{tau}$ (ng · h/mL) | 918 ± 319 | 250 ± 125 |

Note:
Values are normalized to 25 mg CD for ER CD-LD and 70 mg CD for IPX203.

The CD accumulation, fluctuation and time invariance parameters were:

| | Mean ± SD (N = 27) | | |
|---|---|---|---|
| Treatment | Accumulation Ratio | Fluctuation Index | Time Invariance |
| IPX203 | 1.1 ± 0.6[a] | 1.7 ± 0.4 | 0.92 ± 0.5[a] |
| IR CD-LD | 1.1 ± 0.5[b] | 1.5 ± 0.5 | 0.83 ± 0.4[b] |

[a]N = 26; [b]N = 20

Note:
Accumulation ratio was calculated as the ratio of $AUC_{tau}$ on Day 15 to $AUC_{tau}$ on Day 1, where tau (dosing interval) on Day 1 was assigned the same value as tau on Day 15.
Fluctuation index was calculated as $(C_{max} - C_{min})/C_{avg}$ over 10 hours of PK assessment.
Time invariance was calculated as the ratio of $AUC_{tau}$ on Day 15 to $AUC_\infty$ on Day 1.

Efficacy Results

The results of the primary efficacy parameter, "Off" time as a percent of waking hours, measured from PD diary data on Days 12 to 14 of each treatment period were:

| "Off" | | | | Treatment Comparison | |
|---|---|---|---|---|---|
| Time (% of Waking Hours) | Subject Diary Data Days 12-14 | | | p-value 95% CI of LS Means Difference | LS Means Difference |
| | Screening (N = 27) | IPX203 (N = 27) | IR CD-LD (N = 27) | | |
| Mean (SD) | 32.2 (11.0) | 19.3 (14.4) | 33.5 (16.1) | −14.26 | <0.0001 (−19.83, −8.69) |
| Median | 30.7 | 16.4 | 28.9 | | |
| Min, Max | (15.8, 53.9) | (0.0, 45.6) | (10.9, 66.1) | | |

The above data shows that with IPX203 treatment subjects experienced significantly less "Off" time as a percentage of their waking hours, mean 19.3% compared with 33.5% with JR CD-LD.

The PD diary data is summarized as follows:

| | | | | Treatment Comparison IPX203 vs. IR CD-LD | |
|---|---|---|---|---|---|
| | Mean (SD) Hours (N = 27) | | | LS Means | |
| Motor State | Screening | IPX203 | IR CD-LD | Difference | p-value (95% CI) |
| "Good On" | 9.98 (2.3) | 12.07 (2.5) | 10.17 (2.6) | 1.91 | 0.0001 (1.05, 2.76) |
| "Off" | 5.17 (1.9) | 3.22 (2.5) | 5.47 (2.9) | −2.26 | <0.0001 (−3.17, −1.35) |
| "On" without dyskinesia | 8.18 (3.5) | 9.69 (4.3) | 7.64 (3.9) | 2.05 | 0.0135 (0.46, 3.63) |
| "On" with nontroublesome dyskinesia | 1.80 (2.4) | 2.38 (3.4) | 2.54 (3.3) | −0.14 | 0.8313 (−1.46, 1.18) |
| "On" with troublesome dyskinesia | 0.90 (1.7) | 0.94 (2.2) | 0.46 (0.8) | 0.48 | 0.1484 (−0.18, 1.14) |
| Asleep | 7.95 (1.6) | 7.77 (1.8) | 7.90 (1.7) | −0.12 | 0.5593 (−0.55, 0.31) |

Note:
Screening data collected on Days −3 to −1. Active treatment data collected on Days 12-14 in each treatment period. Mean values represented the average time per day that the subject reported being in the particular motor state over the 3-day collection period.
"Good On" time = "On" without dyskinesia time + "On" with nontroublesome dyskinesia time.

MDS-UPDRS Parts I-IV (Predose Day 15)

MDS-UPDRS Parts I, II, III, and IV were administered at screening (while subjects were in the "On" state) and at predose on Day 15 for each treatment. MDS-UPDRS Part III was also administered at screening while subjects were in the "Off" state. Parts I, II, and IV contain questions that inquire about the subject's retrospective experience over the past week. Part III is a real time motor exam performed by the investigator to assess the motor signs of PD.

When predose mean MDS-UPDRS Parts I-IV scores were compared by treatment on Day 15 (between-treatment LS means difference), scores were significantly lower during IPX203 treatment for Parts III (−8.1 [25.3], p=0.0272), IV (−1.6 [3.09], p=0.0109), II+III (−9.0 [26.9], p=0.0213) and MDS-UPDRS total score (−11.5 [30.9], p=0.0116) than during IR CD-LD treatment, indicating less PD impairment. Results for Parts I and II showed no significant treatment difference. At screening, the mean Part III score in all subjects in the "Off" state was 42.6; the mean score on Day 15 was 41.6 during IR CD-LD treatment, whereas the mean score decreased to 33.5 during IPX203 treatment (LS means difference −8.1 [25.0]. p=0.0255).

On Day 1, mean predose MDS-UPDRS Part III scores were similar for both treatment (42.8 and 41.4 for IPX203 and JR CD-LD, respectively) and reflected the predose "Off" state, with subjects having taken no PD medication since 10 PM the previous evening.

At the 1 and 2 hour time points, there were notable reductions in MDS-UPDRS Part III scores from predose values during both IPX203 and JR CD-LD treatment, with no significant differences between treatments. From 3 to 8 hours post dose, IPX203 was associated with a significantly greater reduction in MDS-UPDRS Part III scores than JR CD-LD. At the 7 hour post dose time point, treatment with IPX203 was associated with a mean improvement of almost 10 units vs a worsening of 0.2 units for JR CD-LD. Over the 8 hour post dose period mean MDS-UPDRS scores were reduced by 19.3 points and 8.4 points for subjects in the IPX203 and JR CD-LD treatment periods respectively. The following is a summary of the change from predose MDS-UPDRS Part III scores on Day 1:

| Postdose Time Point | Mean (SD) Change from Predose in MDS-UPDRS Part III Score | | LS Mean | |
|---|---|---|---|---|
| | IPX203 (N = 27) | IR CD-LD (N = 27) | Difference (SD) | p-value |
| 1 hour | −21.3 (10.6) | −19.5 (12.9) | −1.1 (12.9) | 0.6530 |
| 2 hours | −26.9 (11.0) | −24.7 (10.3) | −1.2 (8.8) | 0.4862 |
| 3 hours | −27.4 (11.4) | −14.5 (13.7) | −12.0 (14.6) | 0.0003 |
| 4 hours | −24.5 (15.4) | −8.2 (12.6) | −15.3 (16.9) | <0.0001 |
| 5 hours | −22.4 (16.4) | −1.0 (9.6) | −20.6 (16.0) | <0.0001 |
| 6 hours | −19.1 (14.7) | 0.2 (5.2) | −18.7 (13.3) | <0.0001 |
| 7 hours | −9.8 (13.0) | 0.2 (3.8) | −9.6 (11.5) | 0.0002 |
| 8 hours | −2.7 (6.7) | 0.5 (3.1) | −3.2 (9.9) | 0.0241 |
| Postdose average | −19.3 (10.1) | −8.4 (6.1) | −10.2 (8.1) | <0.0001 |

Note:
Day 1 post-rescue values were imputed to the predose value.

Figure 9:
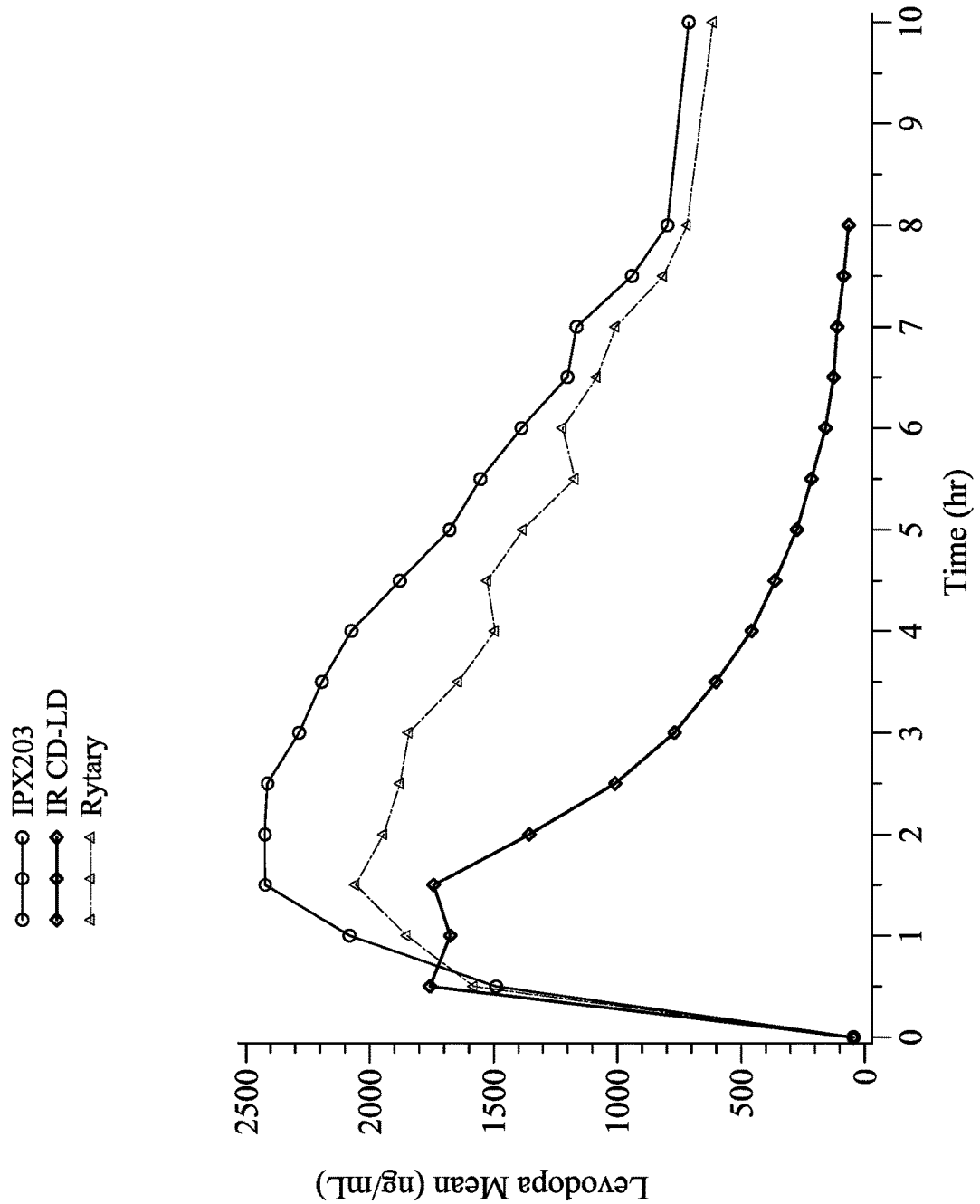
FIG. 9 shows the in vivo levodopa plasma profiles for the formulations tested in Example 9.

To further characterize the duration of effect for each treatment, the MDS-UPDRS Part III data was analyzed using minimal improvement thresholds (4, 7, and 13 unit improvements). An improvement of at least 4 MDS-UPDRS Part III united represents the minimal change that is clinically meaningful to the patient. On Day 1, subjects has significantly longer total durations of pharmacodynamics effect during IPX203 treatment than IR CD-LD treatment based on minimal improvement thresholds of at least 4, 7 and 13 MDS-UPDRS Part III units as shown by the following summary table:

| Improvement | Mean (SD) Total Hours of Specified Improvement from Predose in MDS-UPDRS Part III Score | | LS Mean | |
|---|---|---|---|---|
| | IPX203 (N = 27) | IR CD-LD (N = 27) | Difference (SD) | p-value |
| FIG. 9 ≥4 units | 6.17 (1.3) | 3.46 (1.6) | 2.69 (2.0) | <0.0001 |
| ≥7 units | 5.70 (1.5) | 3.35 (1.6) | 2.34 (2.0) | <0.0001 |
| ≥13 units | 5.30 (1.9) | 2.44 (1.4) | 2.84 (1.8) | <0.0001 |

Note:
Day 1 post-rescue values were imputed to the predose value.

Figure 6:
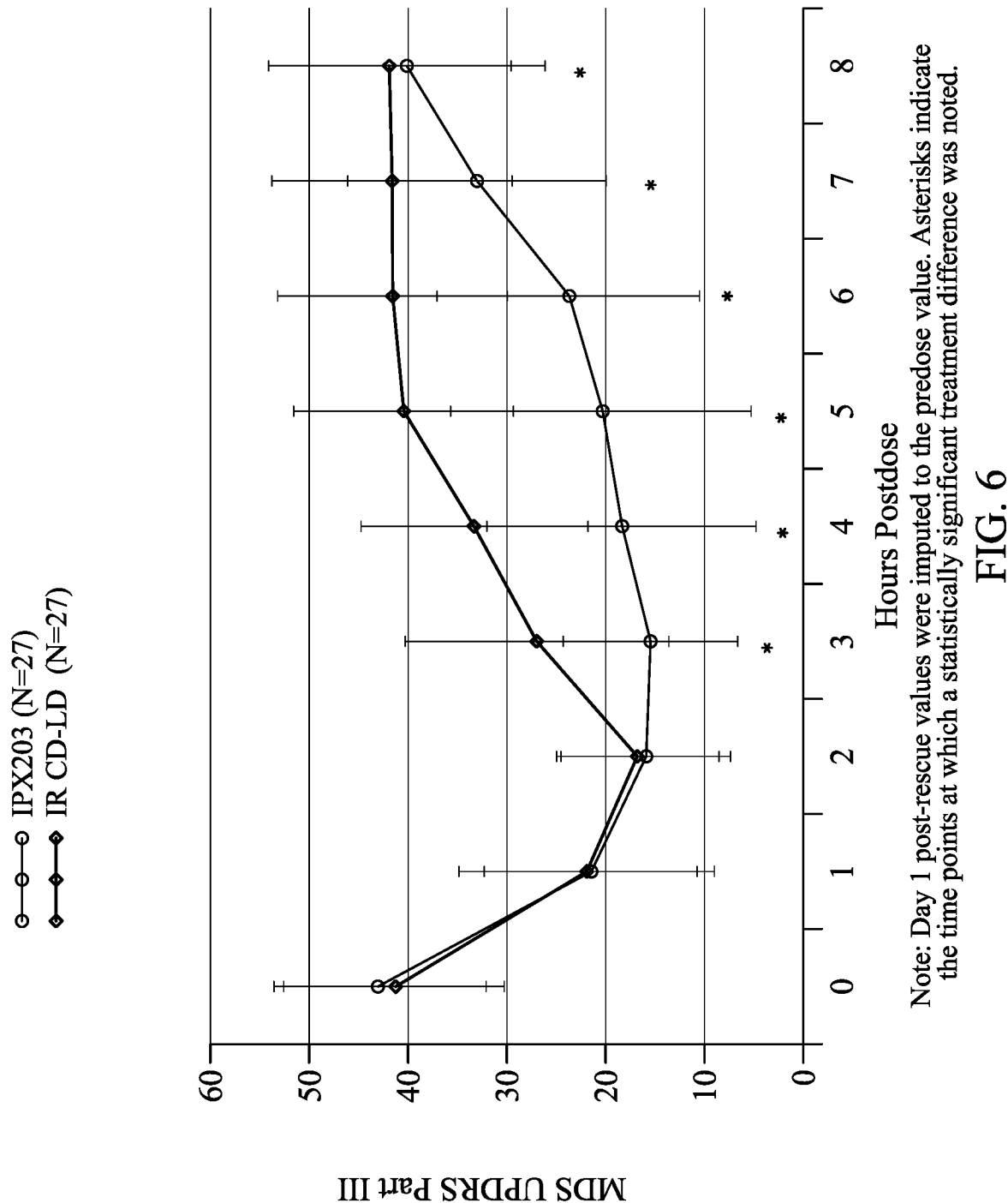
FIG. 6 shows the mean MDS-UPDRS Part III scores on day 1 for the formulations tested in Example 8.

A graph of the mean MDS-UPDRS Part III on day 1 is shown in FIG. 6.

Predose on Day 15, when subjects had not had a study treatment for at least 5 hours, the mean MDS-UPDRS Part III score was significantly lower during IPX203 treatment (33.5) than during ID CD-LD treatment (41.6). The clinical effects of IPX203 carried over to the following morning. During the 10 hour post dose assessment period on Day 15, subjects saw improvements from Day 1 predose scores with both treatments as summarized in the following table:

| | Mean (SD) Change in MDS-UPDRS Part III Score | | LS Mean | |
|---|---|---|---|---|
| | IPX203 (N = 27) | IR CD-LD (N = 27) | Difference (SD) | p-value |
| Predose[a] | −9.3 (15.4) | 0.1 (8.5) | −9.0 (23.3) | 0.0087 |
| Postdose Time Point | | | | |
| 1 hour | −25.4 (13.1) | −20.6 (9.7) | −4.1 (13.1) | 0.1163 |
| 2 hours | −29.4 (11.6) | −25.2 (9.6) | −3.2 (6.8) | 0.0254 |
| 3 hours | −29.5 (12.6) | −16.9 (14.7) | −11.5 (10.5) | <0.0001 |
| 4 hours | −25.5 (13.9) | −14.9 (14.7) | −9.6 (12.9) | 0.0008 |
| 5 hours | −24.9 (14.5) | −20.0 (15.8) | −3.9 (14.8) | 0.1992 |
| 6 hours | −22.0 (16.6) | −22.3 (13.2) | 1.7 (12.1) | 0.5099 |
| 7 hours | −17.8 (16.9) | −20.7 (13.9) | 4.2 (12.4) | 0.1027 |
| 8 hours | −22.0 (16.7) | −15.1 (12.8) | −6.1 (16.2) | 0.0696 |
| 9 hours | −23.9 (15.9) | −18.0 (13.2) | −4.9 (14.1) | 0.0779 |
| 10 hours | −25.6 (14.7) | −20.6 (13.2) | −4.0 (13.7) | 0.1502 |
| Postdose average | −24.6 (13.6) | −19.42 (10.5) | −4.1 (8.2) | 0.0226 |

[a]These values reflect the change from predose on Day 1 to predose on Day 15
Note:
Day 15 post-redose values were not imputed.

Analysis of minimal improvement thresholds for MDS-UPDRS Part III scores demonstrate similar total durations of improvement of at least 4 and 7 units for both treatment groups, but a significantly longer total duration of improvement for IPX203 of at least 13 units.

Figure 7:
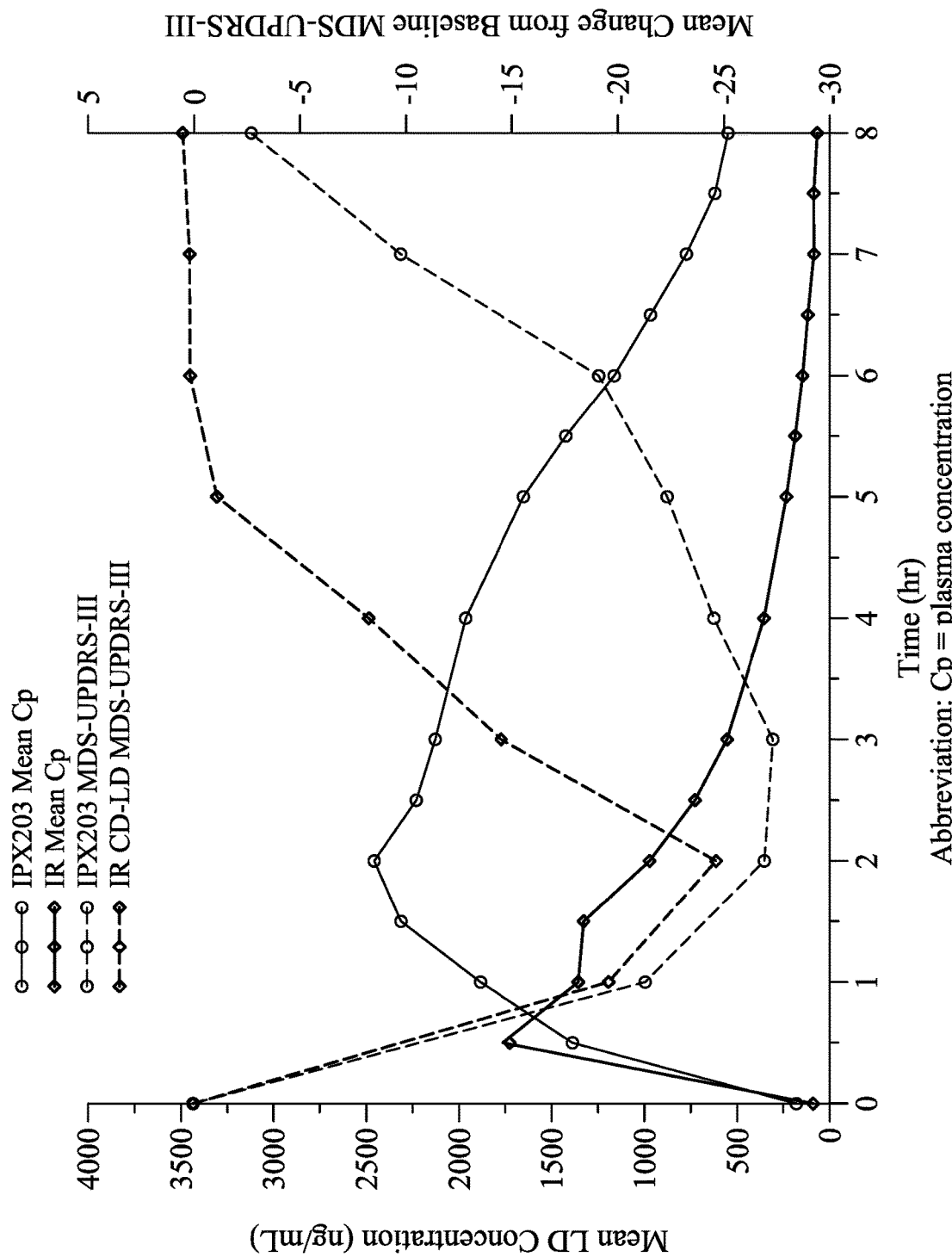
FIG. 7 shows the time course of mean LD plasma concentrations and change from average baseline in MDS-UPDRS Part III scores on day 1 by treatment for the formulations tested in Example 8.

FIG. 7 shows the time course of mean LD plasma concentrations and change from average baseline in MDS-UPDRS Part III scores by treatment following a single dose on Day 1. FIG. 7 shows a good concordance between the LD plasma concentration profile and response as assessed by the changes in MDS-UPDRS Part III scores. The initial decreases in MDS-UPDRS Part III scores from average baseline (corresponding to an improvement in motor symptoms) were comparable between the 2 treatments. However, decrements in the MDS-UPDRS Part III scores lasted for a longer duration following IPX203 treatment than following IR CD-LD treatment. Maximum decreases in MDS-UPDRS Part III scores from average baseline occurred at times that lagged behind the time of peak plasma concentrations of LD for the particular treatment.

Figure 8:
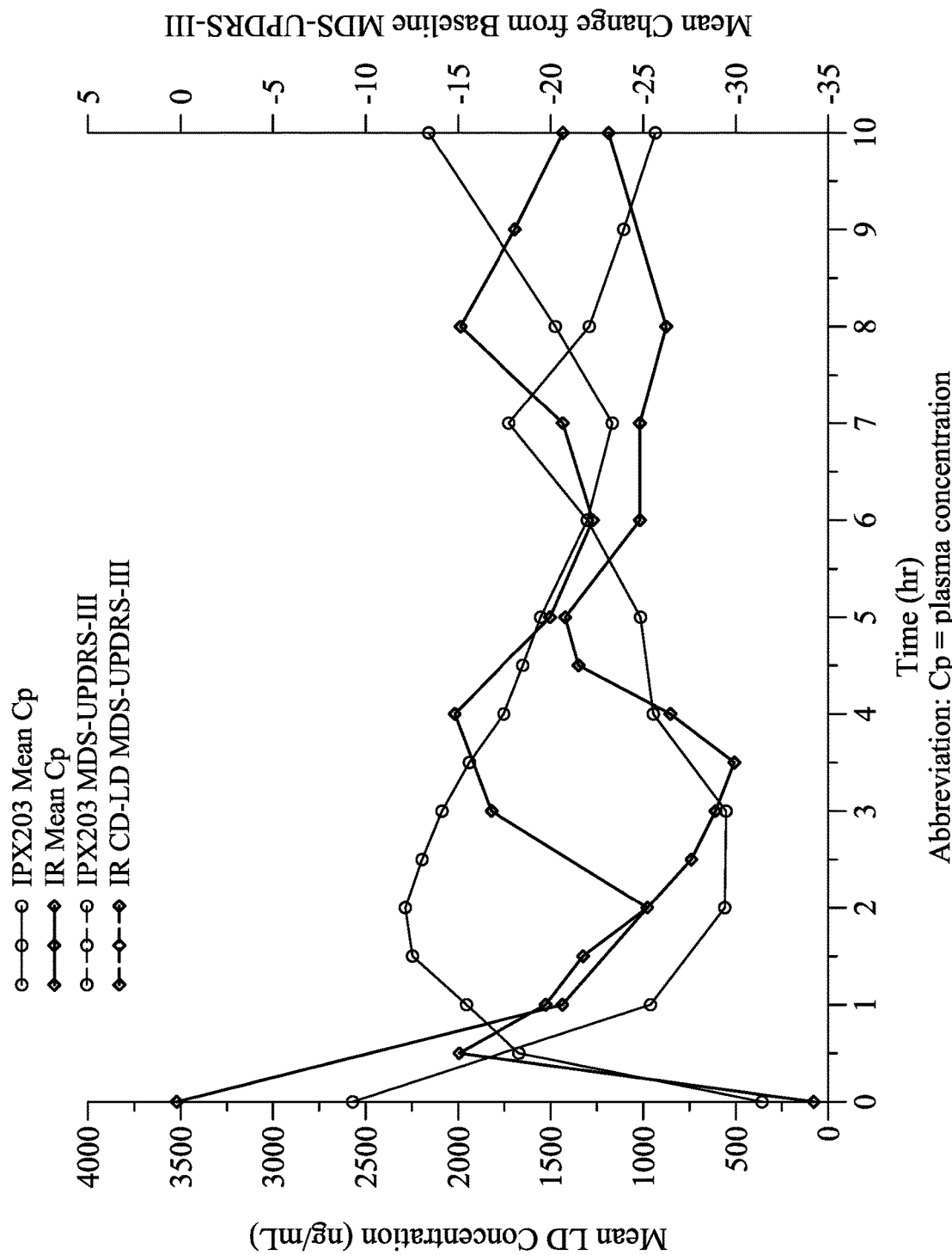
FIG. 8 shows the time course of mean LD plasma concentrations and change from average baseline in MDS-UPDRS Part III scores on day 15 by treatment for the formulations tested in Example 8.

FIG. 8 shows the time course of mean LD plasma concentrations and change from average Day 1 predose in MDS-UPDRS Part III scores by treatment on Day 15 of subject's stable dosing regimen. At predose on Day 15, treatment with IPX203 showed a greater mean decrement (−9.3) in MDS-UPDRS Part III scores than did treatment with IR CD-LD (+0.1). FIG. 8 shows a good concordance between the LD plasma concentration profile and changes in MDS-UPDRS Part III scores. The initial rates of improvement in motor symptoms were comparable between the 2 treatments. However, improvements in the MDS-UPDRS Part III scores lasted for a longer duration following IPX203 treatment than IR CD-LD, which resulted in subjects requiring less frequent dosing of IPX203 than IR CD-LD.

Across all efficacy and pharmacodynamics measures, IPX203 treatment clearly demonstrated advantages over IR CD-LD and its usefulness in alleviating PD symptoms. With IPX203 treatment subject experienced significantly less "Off" time as a percentage of their waking hours (mean 19.3% compared with 33.5% with IR CD-LD). In addition, subjects had significantly more total "Good On" time with IPX203 treatment compared with IR CD-LD, whether measured out of clinic by the subject with home diary or by the investigator in the clinic. The average durations of "Good On" episodes or any "On" episodes based on patient diary entries were significantly longer with IPX203 compared with IR CD-LD. Treatment with IPX203 was also associated with significantly fewer motor fluctuations per day than IR CD-LD. During IPX203 treatment, subjects were 73.3% less likely to receive rescue medication (Day 1) and 72.1% less likely to receive a second dose (Day 15) than during IR CD-LD treatment.

Improvements in MDS-UPDRS Part III mean scores were significantly greater for subjects receiving IPX203 than IR CD-LD from 3 to 8 hours post dose on Day 1 and from 2 to 4 hours post dose on Day 15. On Day 15, when subjects had not had a study treatment for at least 5 hours, mean predose Part III scores were significantly lower during IPX203 treatment, which allows the clinical effects of IPX203 to carry over to the next morning.

Based on the Investigator Assessment of Subject's Motor State, the average time to the first "On" was similar during each treatment following Day 1 first dose and during steady state dosing following day 15 first dose. On Day 15, on average subjects turned "On" about 10 minutes (0.17 hours) faster during (PX203 treatment compared with JR CD-LD treatment and by 0.5 hours post dose 44% of subjects experienced their first "On" during IPX203 treatment versus 26% of subjects during JR CD-LD treatment.

The investigator assessment of subject motor state was performed by rater who were blinded to the study treatment. The investigator assessment on Day 1 is summarized as follows:

|  | Mean (SD) Hours | | Treatment Comparison IPX203 vs. IR CD-LD | |
| --- | --- | --- | --- | --- |
|  | (N = 27) | | LS Means | |
| Motor State | IPX203 | IR CD-LD | Difference | p-value (95% CI) |
| "Good On" | 5.31 (1.4) | 2.74 (1.4) | 2.57 | <0.0001 (1.82, 3.33) |
| "Off" | 2.54 (1.4) | 5.11 (1.4) | −2.57 | <0.0001 (−3.26, −1.87) |
| "On" without dyskinesia | 3.80 (2.0) | 1.94 (1.3) | 1.84 | 0.0003 (0.93, 2.74) |
| "On" with nontroublesome dyskinesia | 1.52 (2.0) | 0.80 (1.0) | 0.74 | 0.0285 (0.08, 1.39) |
| "On" with troublesome dyskinesia | 0.04 (0.2) | 0.13 (0.5) | −0.10 | 0.3489 (−0.31, 0.11) |
| Asleep | 0.11 (0.4) | 0.02 (0.1) | 0.09 | 0.1774 (−0.05, 0.23) |

Note:
Day 1 post-rescue values were imputed to "Off"

The proportion of subjects in "On" or in "Off" state in the first 30 minutes upon awaking from nocturnal sleep was determined based on the subjects PD diary entries as follows:

| Proportion of Subjects in ON State in the First 30 Minutes Upon Awaking from Nocturnal Sleep | | | | |
| --- | --- | --- | --- | --- |
| Days of ON upon Awakening | Screening (N = 27) | IPX203 (N = 27) | IR CD-LD (N = 27) | IPX203 vs IR CD-LD p-value |
| 3 Evaluable Diary Days | | | | |
|  | (N = 27) | (N = 26) | (N = 27) | |
| 3 Days with ON | 0 | 4 (15.4%) | 1 (3.7%) | 0.1917 |
| 2 Days with ON | 0 | 3 (11.5%) | 3 (11.1%) | 1.000 |
| 1 Day with ON | 3 (11.1%) | 3 (11.5%) | 4 (14.8%) | 1.000 |
| 0 Days with On | 24 (88.9%) | 16 (61.5%) | 19 (70.4%) | 0.5694 |
| 1 Evaluable Diary Day | | | | |
|  | (N = 0) | (N = 1) | (N = 0) | |
| 1 day with ON | 0 | 0 | 0 | |
| 0 Days with ON | 0 | 1 (100%) | 0 | |

| Proportion of Subjects in "Off" State in the First 30 Minutes Upon Awaking from Nocturnal Sleep | | | | |
| --- | --- | --- | --- | --- |
| Days of "Off" upon Awakening | Screening (N = 27) | IPX203 (N = 27) | IR CD-LD (N = 27) | IPX203 vs IR CD-LD p-value |
| 3 Evaluable Diary Days | | | | |
|  | (N = 27) | (N = 26) | (N = 27) | |
| 3 Days with "Off" | 24 (8.9%) | 16 (61.5%) | 19 (70.4%) | 0.5694 |
| 2 Days with "Off" | 3 (11.1% | 3 (11.5%) | 4 (14.8%) | 1.000 |
| 1 Day with "Off" | 0 | 3 (11.5%) | 3 (11.1%) | 1.000 |
| 0 Days with "Off" | 0 | 4 (15.4%) | 1 (3.7%) | 0.1917 |
| 1 Evaluable Diary Day | | | | |
|  | (N = 0) | (N = 1) | (N = 0) | |
| 1 day with "Off" | 0 | 1 (100%) | 0 | |
| 0 Days with "Off" | 0 | 0 | 0 | |

The p-values in the above awaking tables is based on Fisher's Exact Test, the analysis does not take into account the crossover nature of the study design.

The above data for the first 30 minutes upon awaking shows IPX 203 improves ON time upon awaking from nocturnal sleep.

Example 9

The dosage forms described in Example 5 were administered to 25 subjects with advanced PD in a randomized, open-label, rater-blinded, multicenter, 3-treatment, 3-periods single-dose crossover study. The subjects were randomized into 1 of 3 dosing sequences receiving the compositions of Example 5 ("IPX203"), RYTARY® a commercially available CD-LD extended release capsule product and an immediate release CD-LD ("IR CD-LD") tablet commercially available under the tradename SINEMET®. Subjects reported to the study clinic three times for a single dose of each study treatment, with a 1-week washout period between visits. Subjects could continue taking IR CD-LD between study visits. Subjects presented to the clinic in a fasted state, with their last dose of IR CD-LD taken no later than 10 PM on the previous day. After dosing, subjects who experienced an "Off" state for ≥3 consecutive hours could receive rescue medication comprising his/her usual IR CD-LD medication dose or a combination rescue containing IR CD-LD. If rescue medication was administered, no further pharmacokinetic or pharmacodynamics measurements were conducted at that visit and the subject could leave the clinic. Otherwise, subjects remained at the clinic through the final evaluations 10 hours after the study treatment dose.

To be eligible for the study, subjects who were diagnosed with advanced PD with motor fluctuations who were receiving IR CD-LD.

Subjects randomized to receive the compositions of IPX203, RYTARY®, IR CD-LD based on their usual prestudy first morning IR CD-LD dose according to the guidance provided in the following table:

TABLE 4

| Prestudy Morning Dose of LD in IR CD-LD (mg) | Study Treatments | | | | | |
|---|---|---|---|---|---|---|
| | IR CD-LD | | RYTARY® | | IPX203 | |
| | LD (mg) | Tablets | LD (mg) | Capsules | LD (mg) | Capsules |
| 100 | 100 | 1 (1 × 100) | 340 | 2 (1 × 195 plus 1 × 145) | 360 | 2 (2 × 180) |
| 150 | 150 | 1.5 (1.5 × 100) | 485 | 3 (1 × 195 plus 2 × 145) | 540 | 3 (3 × 180) |
| 200 | 200 | 2 (2 × 100) | 630 | 4 (1 × 195 plus 3 × 145) | 720 | 3 (2 × 270 plus 1 × 180) |
| 250 | 250 | 2.5 (2.5 × 100) | 780 | 4 (4 × 195) | 810 | 3 (3 × 270) |

CD and LD were present at a fixed ratio of 1:4 in each strength and treatment

The inclusion criteria were similar the inclusion criteria provided in Example 8, except the prestudy total daily maximum LD dose was 1600 mg for this study rather than 1800 mg as allowed in Example 8.

Subjects received a single oral dose of each of the three study treatments in a randomized sequence based on the subjects prestudy morning dose of JR CD-LD as outlined above. The IPX203 and RYTARY® doses were also selected to provide a peak LD plasma concentration that was estimated to be within ±20% of the peak LD plasma concentration of the JR CD-LD dose.

All subjects were administered the single oral dose with 240 mL of room-temperature water and instructed to swallow the study drug intact without crushing or chewing in the morning at a scheduled clinical after having withheld LD since 10 PM the previous evening and fasted for at least 8 hours. Coffee, tea, water and juice were allowed for up to 1 hour prior to dosing. A breakfast containing approximately 5 grams of protein was served approximately 1 hour after dosing.

Pharmacokinetics were determined by the procedures outlined in Example 8. The pharmacodynamics were measured by the Investigator Assessment of Subject's Motor State as outlined in Example 8 at 1 hour, 0.5 hour predose, just before dosing and every half hour post dose and by use of MDS-UPDRS Part III motor examination as outlined in Example 8.

The subject demographics for this study were as follows:

| | Randomized Subjects (N = 26) | Completed Subjects (N = 25) |
|---|---|---|
| Age (years) | 65.9 ± 7.2 | 66.2 ± 7.1 |
| Height (cm) | 166.9 ± 9.9 | 166.8 ± 10.1 |
| Weight (kg) | 83.53 ± 23.1 | 82.2 ± 22.5 |
| Body mass index (kg/m²) | 30.0 ± 8.2 | 29.6 ± 8.1 |
| Gender, N (%) | | |
| Male | 14 (53.8%) | 13 (52.0%) |
| Female | 12 (46.2%) | 12 (48.0%) |
| Race, N (%) | | |
| White | 24 (92.3%) | 23 (92.0%) |
| Asian | 1 (3.8%) | 1 (4.0%) |
| Other (Native Hawaiian or Other Pacific Islander and Filipino) | 1 (3.8%) | 1 (4.0%) |

Note:
Values are mean ± SD unless stated otherwise

The LD dose in subjects who received all three treatments was 168.0 mg for ID CD-LD, 586.8 mg for IPX203 and 538.2 mg for RYTARY®. The mean LD plasma profiles for each treatment are shown in FIG. 9 and the primary LD pharmacokinetic values were as follows:

| Parameter | IPX203 | IR CD-LD | RYTARY® |
|---|---|---|---|
| | (N = 24) | | |
| | All Doses | All Doses | All Doses |
| $C_{max}$ (ng/mL) | 3161 ± 1665 | 2492 ± 1459 | 2839 ± 1909 |
| $T_{max}$ (h) | 2.0 (0.5-7.0) | 1.0 (0.5-2.5) | 2.0 (0.5-6.5) |
| $t_{1/2}$ (h) | 2.3 ± 0.9 | 1.4 ± 0.3 | 2.0 ± 0.7 |
| $AUC_t$ (ng · h/mL) | 13291 ± 7264 | 4879 ± 2631 | 10467 ± 6771 |
| $AUC_{0-\infty}$ (ng · h/mL) | 16734 ± 9759 | 5456 ± 2896 | 13840 ± 8899 |
| Bioavailability (%)[a] | 88 ± 23 | — | 77 ± 24 |
| | Dose Level 1 (N = 7) | | |
| | 360 mg | 100 mg | 340 mg |
| $C_{max}$ (ng/mL) | 1692 ± 530 | 1193 ± 308 | 1371 ± 604 |
| $T_{max}$ (h) | 2.0 (0.5-6.0) | 1.0 (0.5-2.5) | 3.0 (1.0-5.5) |
| $t_{1/2}$ (h) | 1.6 ± 0.5 | 1.2 ± 0.1 | 1.8 ± 1.0 |
| $AUC_t$ (ng · h/mL) | 6403 ± 2051 | 2250 ± 681 | 5159 ± 2124 |
| $AUC_{0-\infty}$ (ng · h/mL) | 7602 ± 2569 | 2641 ± 502 | 7001 ± 3002 |
| Bioavailability (%)[a] | 80 ± 21 | — | 80 ± 36 |
| | Dose Level 2 (N = 5) | | |
| | 540 mg | 150 mg | 485 mg |
| $C_{max}$ (ng/mL) | 2685 ± 1037 | 1844 ± 931 | 2372 ± 843 |
| $T_{max}$ (h) | 3.5 (0.5-7.0) | 0.5 (0.5-2.0) | 2.0 (0.5-6.5) |
| $t_{1/2}$ (h) | 2.4 ± 0.8 | 1.6 ± 0.3 | 2.3 ± 0.8 |
| $AUC_t$ (ng · h/mL) | 12377 ± 6201 | 4184 ± 1537 | 9233 ± 4191 |
| $AUC_{0-\infty}$ (ng · h/mL) | 16638 ± 5558 | 4418 ± 1543 | 10841 ± 4197 |
| Bioavailability (%)[a] | 109 ± 29 | — | 78 ± 22 |
| | Dose Level 3 (N = 7) | | |
| | 720 mg | 200 mg | 630 mg |
| $C_{max}$ (ng/mL) | 4016 ± 1222 | 3657 ± 1108 | 4006 ± 2442 |
| $T_{max}$ (h) | 2.0 (0.5-5.5) | 1.0 (0.5-2.0) | 1.5 (0.5-5.0) |
| $t_{1/2}$ (h) | 2.6 ± 1.1 | 1.4 ± 0.3 | 1.9 ± 0.3 |
| $AUC_t$ (ng · h/mL) | 17977 ± 4947 | 6738 ± 1541 | 14423 ± 7757 |
| $AUC_{0-\infty}$ (ng · h/mL) | 22244 ± 6899 | 7477 ± 1454 | 18593 ± 8736 |
| Bioavailability (%)[a] | 82 ± 17 | — | 76 ± 25 |
| | Dose Level 4 (N = 5) | | |
| | 810 mg | 250 mg | 780 mg |
| $C_{max}$ (ng/mL) | 4498 ± 2153 | 3326 ± 1631 | 3726 ± 1829 |
| $T_{max}$ (h) | 1.0 (0.5-2.5) | 1.0 (0.5-1.5) | 1.5 (0.5-3.0) |
| $t_{1/2}$ (h) | 2.7 ± 0.8 | 1.2 ± 0.2 | 2.3 ± 0.9 |
| $AUC_t$ (ng · h/mL) | 17289 ± 8914 | 6653 ± 3242 | 13594 ± 7628 |
| $AUC_{0-\infty}$ (ng · h/mL) | 21904 ± 14246 | 7603 ± 3763 | 18390 ± 12058 |
| Bioavailability (%)[a] | 86 ± 21 | — | 73 ± 15 |

Values are mean ± SD except $T_{max}$ which is median (min-max). Doses shown are of LD; CD and LD are present at a fixed ratio of 1:4 in each treatment.
[a]Calculated relative to IR CD-LD The secondary LD pharmacokinetic values were as follows:

| Parameter | IPX203 | IR CD-LD | RYTARY® |
|---|---|---|---|
| | (N = 24) | | |
| | All Doses | All Doses | All Doses |
| Duration > 50% $C_{max}$ (h) | 4.7 ± 1.6 | 1.9 ± 0.9 | 3.9 ± 1.4 |
| Time to reach 50% $C_{max}$ (h) | 0.7 (0.2-2.1) | 0.4 (0.2-1.4) | 0.5 (0.2-5.7) |
| | Dose Level 1 (N = 7) | | |
| | 360 mg | 100 mg | 340 mg |
| Duration > 50% $C_{max}$ (h) | 4.4 ± 1.9 | 1.7 ± 0.4 | 4.7 ± 1.5 |
| Time to reach 50% $C_{max}$ (h) | 0.7 (0.3-1.5) | 0.7 (0.2-1.4) | 0.6 (0.3-0.9) |
| | Dose Level 2 (N = 5) | | |
| | 540 mg | 150 mg | 485 mg |
| Duration > 50% $C_{max}$ (h) | 4.9 ± 1.6 | 2.0 ± 0.9 | 3.4 ± 0.8 |
| Tune to reach 50% $C_{max}$ (h) | 0.8 (0.2-2.1) | 0.3 (0.2-0.6) | 1.0 (0.3-5.7) |
| | Dose Level 3 (N = 7) | | |
| | 720 mg | 200 mg | 630 mg |
| Duration > 50% $C_{max}$ (h) | 5.3 ± 1.9 | 1.6 ± 0.8 | 3.7 ± 1.6 |
| Time to reach 50% $C_{max}$ (h) | 0.8 (0.3-1.3) | 0.3 (0.2-1.2) | 0.3 (0.2-1.0) |
| | Dose Level 4 (N = 5) | | |
| | 810 mg | 250 mg | 780 mg |
| Duration > 50% $C_{max}$ (h) | 4.3 ± 1.0 | 2.5 ± 1.5 | 3.6 ± 0.9 |
| Time to reach 50% $C_{max}$ (h) | 0.3 (0.3-0.4) | 0.5 (0.2-1.0) | 0.4 (0.3-1.3) |

Duration values are mean ± SD: time to reach values are median (min-max).
One subject (No. 108-001) completed the study but plasma concentrations were not available after any of the treatments The dose normalized LD pharmacokinetic values were as follows:

| Parameter | IPX203 | IR CD-LD | RYTARY® |
|---|---|---|---|
| $C_{max}$ (ng/mL) | 1868 ± 658 | 1415 ± 567 | 1715 ± 905 |
| $AUC_t$ (ng · h/mL) | 7809 ± 3077 | 2774 ± 972 | 6358 ± 3205 |
| $AUC_{0-\infty}$ (ng · h/mL) | 9800 ± 4068 | 3108 ± 988 | 8275 ± 4032 |

Values are normalized to the lowest dose in each treatment, i.e., 100 mg LD (IR CD-LD), 360 mg LD (IPX203), and 340 mg LD (RYTARY®). Values are mean ± SD.
One subject (No. 108-001) completed the study but plasma concentrations were not available after any of the treatments.

The bioavailability of LD based on the dose normalized natural log transformed $AUC_{0-\infty}$ was higher following IPX203 (85.5%) than following RYTARY® (71.8%) relative to IR CD-LD. The bioavailability of LD were as follows:

| | % Ratio of Geometric Mean Estimates (90% Confidence Interval) | | |
|---|---|---|---|
| Comparison | $C_{max}$ | $AUC_{0-t}$ | $AUC_{0-\infty}$ |
| IPX203/IR CD-LD | 37.76 (32.59, 43.75) | 77.50 (71.25, 84.31) | 85.50 (77 89, 93.85) |
| RYTARY®/IR CD-LD | 34.03 (29.38, 39.43) | 62.81 (57.74, 68.32) | 71.79 (65.26, 78.97) |

Data reported are the ratios of the in-transformed dose-normalized geometric means for Test/Reference expressed as a percentage and 90% confidence interval.
One subject (No. 108-001) completed the study but plasma concentrations were not available after any of the treatments.

The LD dose normalized partial AUC values were as follows:

| | % Ratio of Geometric Mean Estimates (90% Confidence Interval) | | |
|---|---|---|---|
| Comparison | $AUC_{0-2}$ | $AUC_{2-8}$ | $AUC_{8-\infty}$ |
| IPX203/IR CD-LD | 34.28 (29.23, 40.20) | 117.40 (105.13, 131.11) | 427.68 (297.96, 613.88) |
| RYTARY®/IR CD-LD | 32.04 (27.32, 37.57) | 94.34 (84.27, 105.62) | 318.80 (222.26, 457.28) |

Data reported are the ratios of the in-transformed dose-normalized geometric means for Test/Reference expressed as a percentage and 90% confidence interval.
Abbreviations: $AUC_{0-2}$ = area under the concentration-time curve from 0 to 2 hours after dosing;
$AUC_{2-8}$ = area under the concentration-time curve between 2 hours and 8 hours after dosing;
$AUC_{8-\infty}$ = area under the concentration-time curve extrapolated from 8 hours up to infinity.

Examination of mean $AUC_{2-8}$ and $AUC_{8-\infty}$ values at all four dose levels shows higher exposures of LD following IPX203 than RYTARY® supporting IPX203's greater bioavailability and extended plasma LD concentration.

Figure 10:
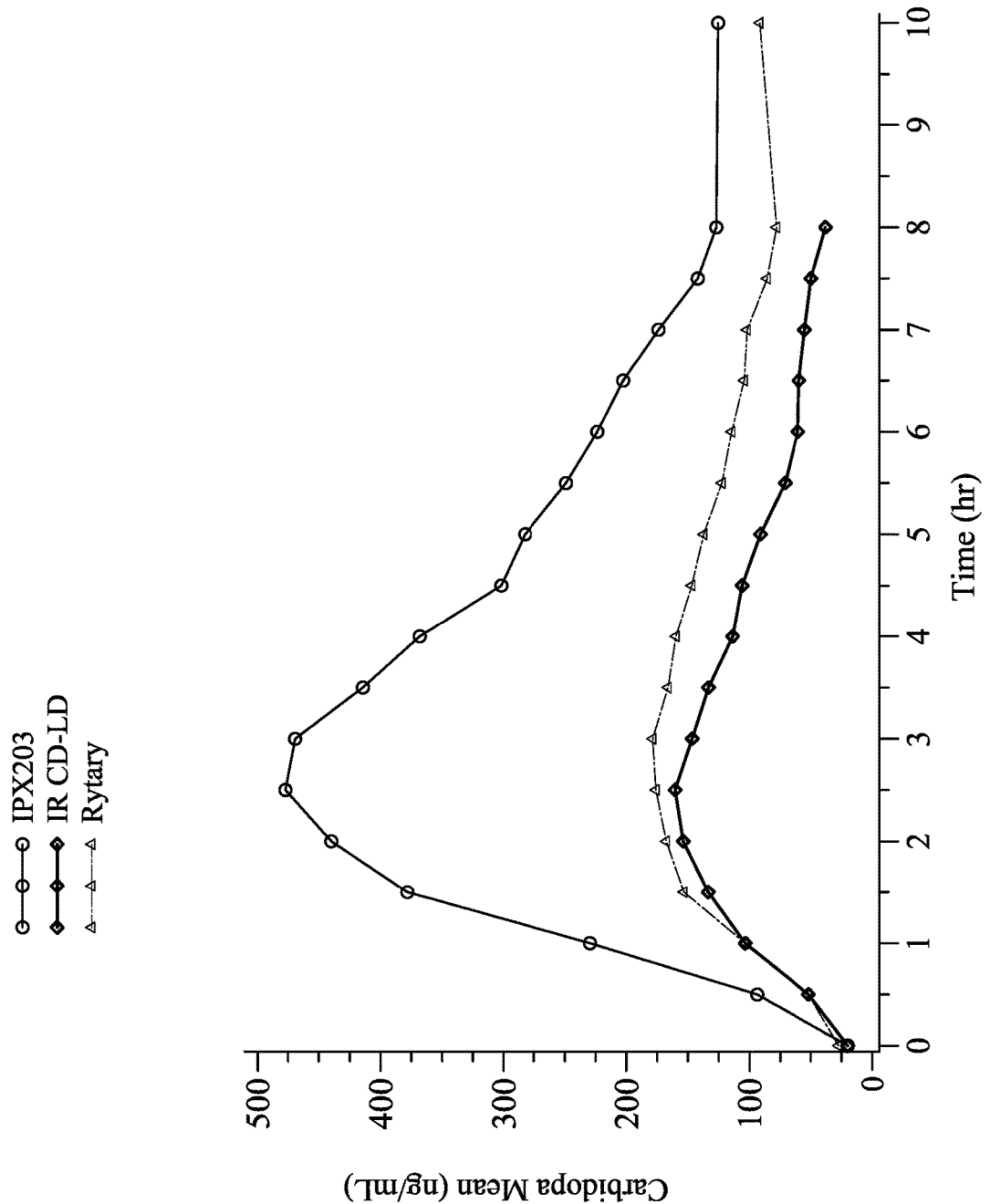
FIG. 10 shows the in vivo carbidopa plasma profiles for the formulations tested in Example 9.

The mean CD plasma profiles for each treatment are shown in FIG. 10 and the primary CD pharmacokinetic values were as follows:

| Parameter | IPX203 | IR CD-LD | RYTARY® |
|---|---|---|---|
| | All Doses, N = 24 | | |
| $C_{max}$ (ng/mL) | 571 ± 400 | 180 ± 123 | 217 ± 130 |
| $T_{max}$ (h) | 2.5 (1.5-6.0) | 2.5 (1.5-3.5) | 2.5 (1.0-7.5) |
| $t_{1/2}$ (h) | 2.3 ± 0.8 | 2.1 ± 0.7 | 2.8 ± 0.9 |
| $AUC_t$ (ng · h/mL) | 2192 ± 1353 | 593 ± 402 | 922 ± 602 |
| $AUC_{0-\infty}$ (ng · h/mL) | 2736 ± 1660 | 760 ± 505 | 1285 ± 809 |
| Bioavailability (%)$^a$ | 140 ± 120 | — | 73 ± 80 |
| Dose Level 1 (N = 7) | 90 mg | 25 mg | 85 mg |
| $C_{max}$ (ng/mL) | 305 ± 116 | 85 ± 33 | 118 ± 44 |
| $T_{max}$ (h) | 2.5 (2.0-3.0) | 2.5 (1.5-3.5) | 2.5 (2.0-5.0) |
| $t_{1/2}$ (h) | 2.0 ± 0.5 | 1.5 ± 0.3 | 3.1 ± 1.1 |
| $AUC_t$ (ng · h/mL) | 1046 ± 324 | 228 ± 133 | 414 ± 108 |
| $AUC_{0-\infty}$ (ng · h/mL) | 1329 ± 540 | 324 ± 123 | 599 ± 106 |
| Bioavailability (%)$^a$ | 123 ± 42 | — | 62 ± 31 |
| Dose Level 2 (N = 5) | 135 mg | 37.5 mg | 121.25 mg |
| $C_{max}$ (ng/mL) | 368 ± 71 | 127 ± 66 | 188 ± 76 |
| $T_{max}$ (h) | 5.0 (2.0-6.0) | 2.5 (2.0-3.5) | 3.0 (2.5-7.5) |
| $t_{1/2}$ (h) | 2.8 ± 1.3 | 2.4 ± 0.9 | 2.6 ± 0.9 |
| $AUC_t$ (ng · h/mL) | 1831 ± 807 | 550 ± 275 | 899 ± 426 |
| $AUC_{0-\infty}$ (ng · h/mL) | 2489 ± 1325 | 690 ± 307 | 1208 ± 537 |
| Bioavailability (%)$^a$ | 117 ± 77 | — | 61 ± 38 |
| Dose Level 3 (N = 7) | 180 mg | 50 mg | 157.5 mg |
| $C_{max}$ (ng/mL) | 659 ± 225 | 248 ± 88 | 255 ± 117 |
| $T_{max}$ (h) | 2.5 (2.0-3.5) | 2.5 (1.5-3.5) | 2.0 (1.5-4.0) |
| $t_{1/2}$ (h) | 2.5 ± 0.4 | 2.5 ± 0.8 | 3.0 ± 0.7 |
| $AUC_t$ (ng · h/mL) | 2637 ± 887 | 858 ± 284 | 1153 ± 523 |
| $AUC_{0-\infty}$ (ng · h/mL) | 3430 ± 1424 | 1178 ± 393 | 1617 ± 524 |
| Bioavailability (%)$^a$ | 83 ± 24 | — | 48 ± 22 |
| Dose Level 4 (N = 5) | 202.5 mg | 62.5 mg | 195 mg |

-continued

| Parameter | IPX203 | IR CD-LD | RYTARY® |
|---|---|---|---|
| $C_{max}$ (ng/mL) | 1022 ± 615 | 271 ± 178 | 332 ± 175 |
| $T_{max}$ (h) | 2.5 (1.5-4.0) | 2.0 (1.5-3.0) | 2.5 (1.0-3.5) |
| $t_{1/2}$ (h) | 1.8 ± 0.7 | 2.1 ± 0.6 | 2.2 ± 0.4 |
| $AUC_t$ (ng · h/mL) | 3535 ± 1865 | 777 ± 551 | 1335 ± 846 |
| $AUC_{0-\infty}$ (ng · h/mL) | 3980 ± 2074 | 767 ± 678 | 1840 ± 1241 |
| Bioavailability (%)[a] | 262 ± 211 | — | 133 ± 156 |

Values are mean ± SD except $T_{max}$ which is median (min – max). $AUC_{0-\infty}$ was estimated from $AUC_t$ values.
[a]Bioavailability was calculated relative to IR CD-LD.
One subject (No. 108-001) completed the study but plasma concentrations were not available after any of the treatments.

The dose normalized CD pharmacokinetic values were as follows:

| Parameter | IPX203 | IR CD-LD | RYTARY® |
|---|---|---|---|
| $C_{max}$ (ng/mL) | 331 ± 159 | 101 ± 48 | 132 ± 56 |
| $AUC_t$ (ng · h/mL) | 1271 ± 534 | 333 ± 175 | 555 ± 268 |
| $AUC_{0-\infty}$ (ng · h/mL) | 1602 ± 725 | 431 ± 223 | 770 ± 334 |

Values are mean ± SD. PK parameters are normalized to lowest dose in each treatment, i.e., 90 mg CD (IPX203), 25 mg CD (IR CD-LD) and 85 mg CD (RYTARY ®).

The bioavailability of CD based on the dose normalized natural log transformed $AUC_{0-\infty}$ was higher following IPX203 (112%) than following RYTARY® (55%) relative to IR CD-LD. The bioavailability of CD were as follows:

| | % Ratio of Geometric Mean Estimates (90% Confidence Interval) | | |
|---|---|---|---|
| Comparison | $C_{max}$ | $AUC_{0-t}$ | $AUC_{0-\infty}$ |
| IPX203/IR CD-LD | 97.60 (83.59, 113.95) | 118.51 (99.84, 140.67) | 112.07 (92.40, 135.92) |
| RYTARY ®/IR CD-LD | 40.09 (34.33, 46.80) | 51.53 (43.41, 61.16) | 55.37 (45.50, 67.38) |

Data reported are ratios of dose-normalized ln-transformed geometric means for Test/Reference expressed as a percentage and 90% confidence intervals.
One subject (No. 108-001) completed the study but plasma concentrations were not available after any of the treatments.

Figure 11:
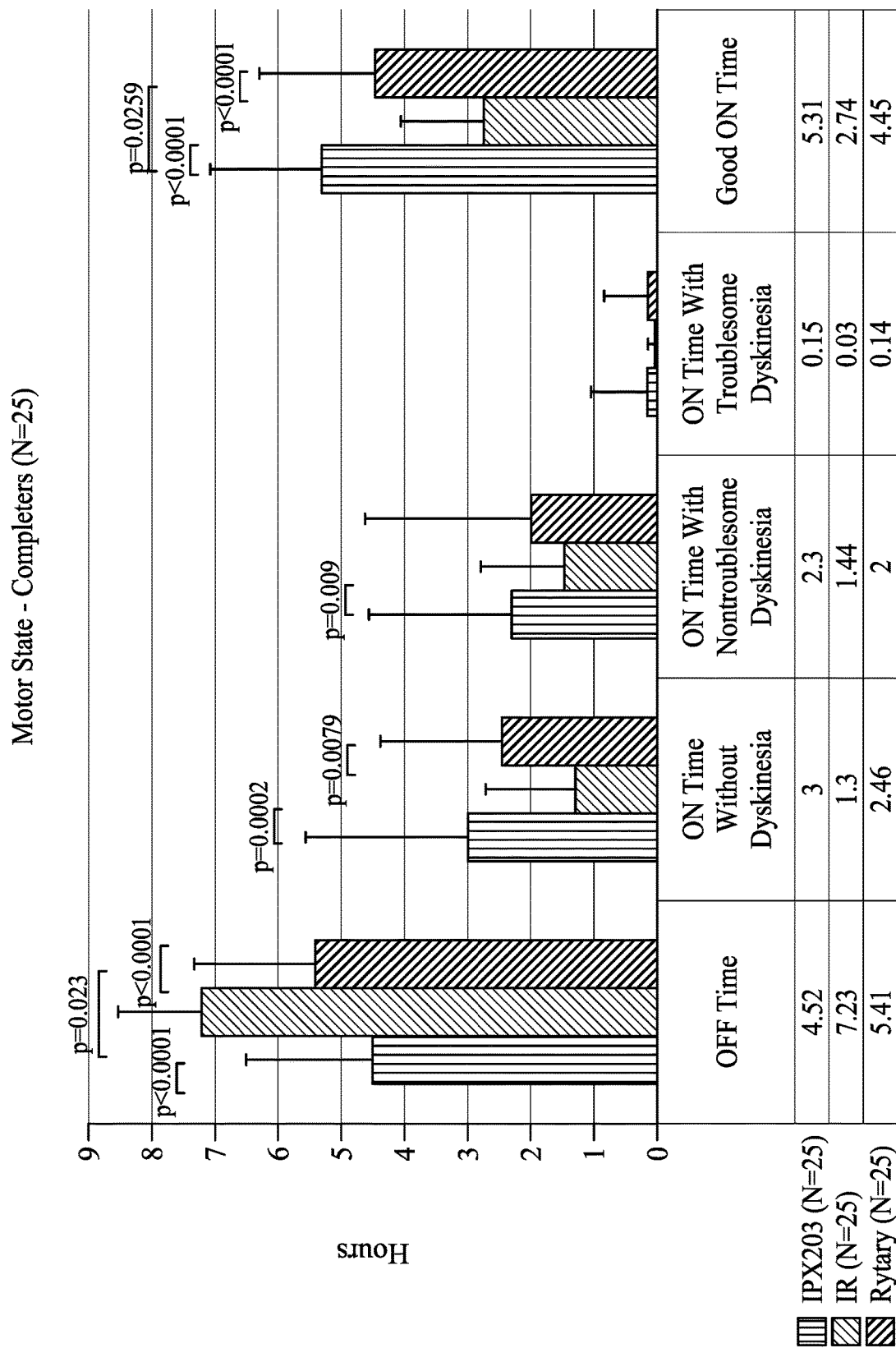
FIG. 11 shows a summary of the Investigator Motor Assessment scores for the formulations tested in Example 9.

Qualified clinical staff who were blinded to treatment assessed each subject's motor state at 1 and 0.5 hours before dosing and at predose, and every thirty minutes following dosing through each 10 hour measurement period. The mean total hours in each awake motor state assessment are presented by treatment in FIG. 11. The least square mean (LSM) "Off" time in the subjects motor state assessment was 4.52 hours for IPX203 and 7.23 hours for IR CD-LD, demonstrating a significant 2.7 hour advantage for IPX203 (p<0.0001). The LSM "Off" time for RYTARY® was 5.41 hours reflecting a 0.9 hour advantage for IPX203 compared with RYTARY® (p=0.023). During IPX203 treatment, this was accompanied by increased Good On time, on average 2.56 hours more than IR CD-LD and 0.85 hours more than RYTARY® (p<0.0001 and p=0.259 respectively). Only two subjects had "On" time with troublesome dyskinesia (one subject during IPX203 [4.5 hr.] and IR CD-LD [0.5 hour] treatment and another subject during RYTARY® treatment [3.5 hour]).

The MDS-PDRS Part III score was assessed at 1 and 0.5 hours before dosing, at predose and every hour after dosing through each 10 hour measurement period. Analysis of covariance was conducted on the mean change from average predose MDS-UPDRS Part III across the 10 hour measurement period, with predose MDS-UPDRS Part III value as a covariate.

Figure 12:
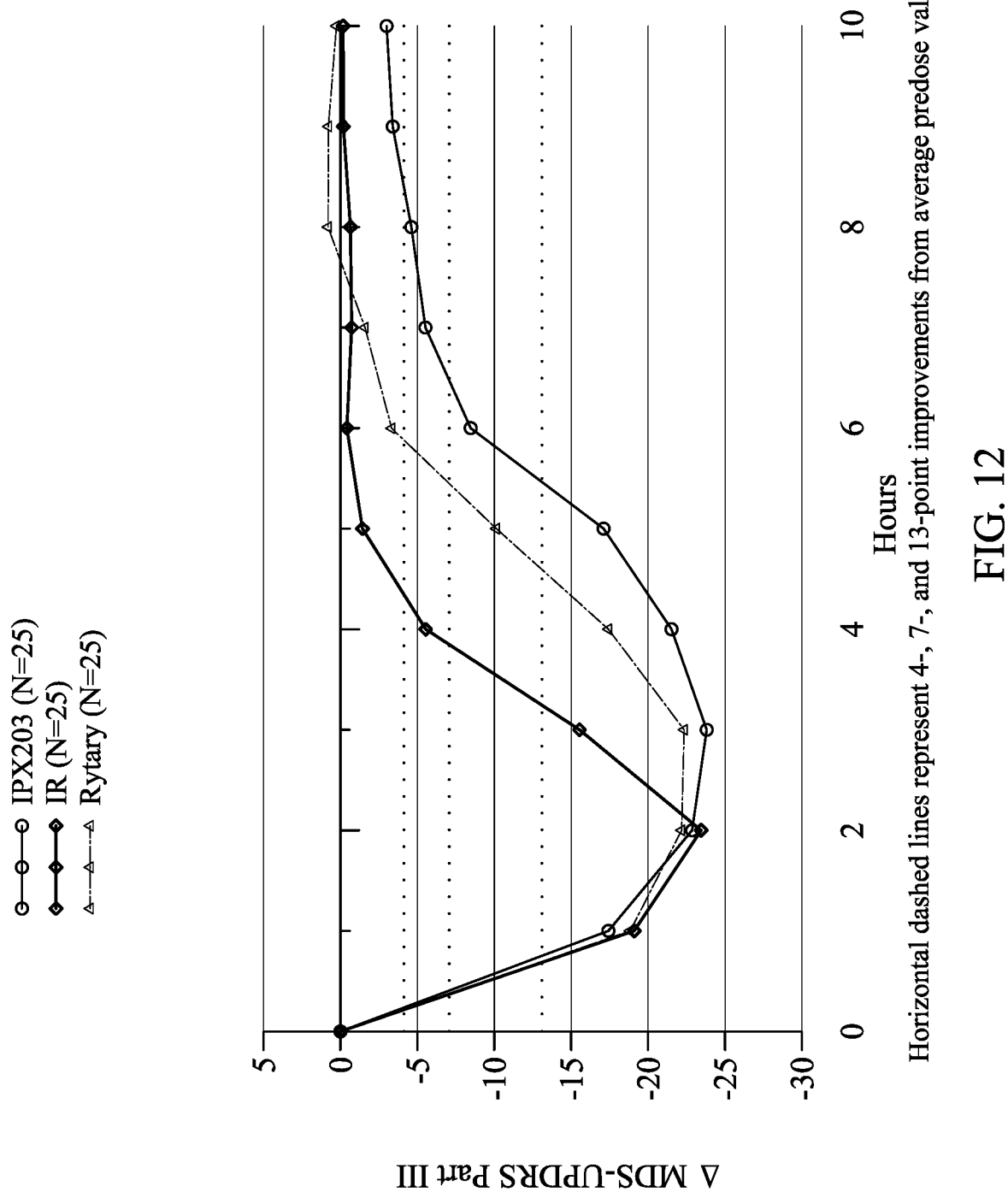
FIG. 12 shows the mean change from average predose MDS-UPDRS Part III scores for the formulations tested in Example 9.

After IPX203 treatment, subjects exhibited significantly greater improvement (decreases) form average predose MDS-UPDRS Part III scores over 10 hours compared with IR CD-LD (−12.70 vs. −6.62, p<0.0001) and also compared to RYTARY® (−12.70 vs. 9.33, p=0.0333) in the overall change form base line as shown in FIG. 12. When these differences were examined hour by hour, results from IPX203 vs IR CD-LD were significantly different from 3 to 10 hours dosing (all p values ≤0.029). RYTARY® was also associated with significantly greater changes in the MDS-UPDRS Part III scores compared with IR CD-LD from 3 to 5 hours post dose (all p values ≤0.0042). Results for IPX203 vs RYTARY® were significantly different form 5 to 10 hours after dosing (all p values ≤0.0352) except at 7 hours.

Figure 13:
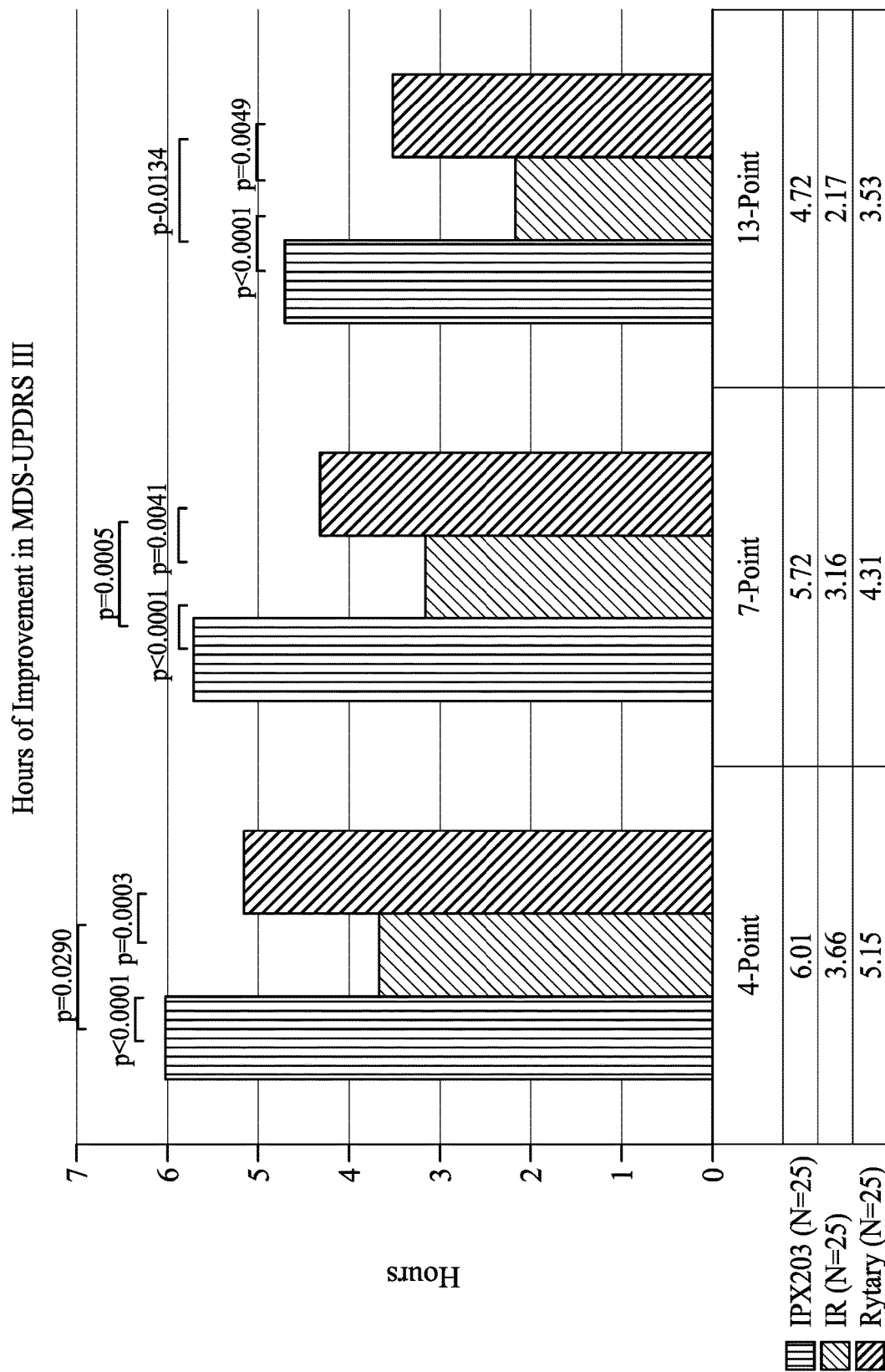
FIG. 13 shows the least square mean hours of 4, 7, or 13 point improvement in the MDS-UPDRS Part III Scores for the formulations tested in Example 9.

Based on MDS-UPDRS Part III results, IPX203 had a significantly longer duration of effect compared with IR CD-LD (p<0.0001) and compared with RYTARY® (p<0.0290), measured by the duration of 4, 7 and 13 point improvement from the average predose value as shown by FIG. 13. Following IPX203 treatment, 72% of subjects had at least a 20% improvement from average predose MDS-UPDRS Part III score at 5 hours postdose compared with 12% and 52% of subjects treated with IR CD-LD and RYTARY® respectively. The proportions of subjects with a 35% improvement at 5 hours were 60%, 8% and 36% for IPX203, IR CD-LD and RYTARY® respectively.

Figure 14:
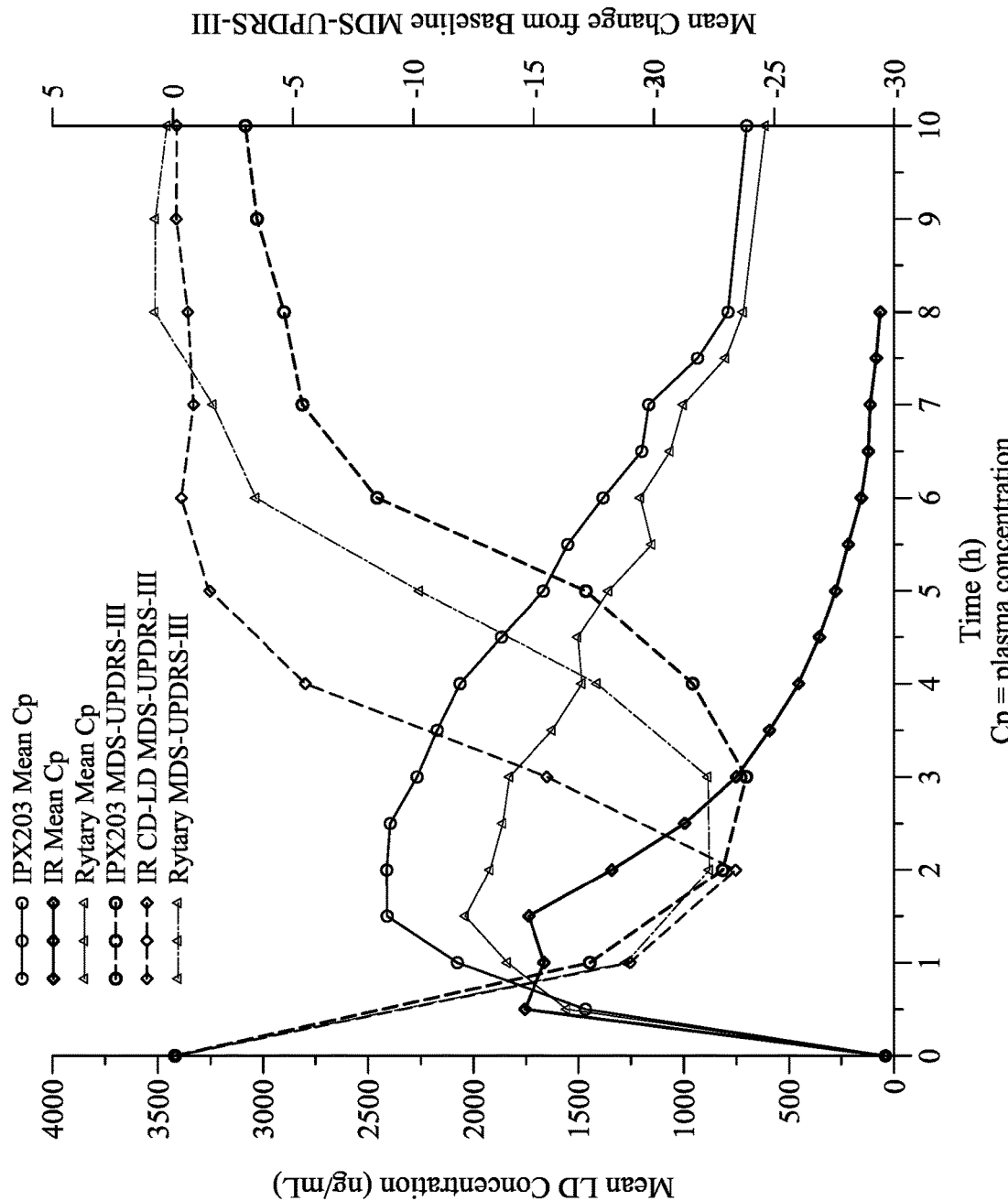
FIG. 14 shows the time course of mean LD plasma concentrations and change from average baseline in MDS-UPDRS Part III scores by treatment for the formulations tested in Example 9.

FIG. 14 shows the time course of mean LD plasma concentrations and change from average baseline in MDS-UPDRS Part III scores by treatment. FIG. 14 demonstrates a good concordance between the PK of LD and response as assessed by the changes in MDS-UPDRS Part III scores. The initial rates of decrease in MDS-UPDRS Part III scores from average baseline (corresponding to an improvement in motor symptoms) were comparable for all three treatments. However, the MDS-UPDRS Part III score decreases lasted for a longer duration following IPX203 treatment than following IR CD-LD or RYTARY®. Maximum decreases in MDS-UPDRS Part III scores from average baseline occurred at times that lagged behind the time of peak plasma concentrations of LD for the particular treatment.

Example 10

The dosage forms described in Example 7 were administered to 40 healthy male and female subjects between the ages of 18 and 55 with a body weight of at least 55 kg and body mass index of 18.5 to 30.0 kg/m2 in a single site open label single dose 5-treatment, 5-periods single-dose crossover study. The subjects will receive the following 5 treatments with 240 mL of room temperature water after an overnight fast of at least 10 hours:
  Treatment A—a single 140 mg levodopa and 35 mg carbidopa capsule;
  Treatment B—a single 210 mg levodopa and 52.5 mg carbidopa capsule;
  Treatment C—a single 280 mg levodopa and 70 mg carbidopa capsule;
  Treatment D—a single 350 mg levodopa and 87.5 mg carbidopa capsule; and
  Treatment E—a single 140 mg levodopa and 35 mg carbidopa capsule.

The capsules employed in Treatment A-D were manufactured at a facility in Brookaven, New York and the capsules employed in Treatment E were manufactured at a facility in Jhunan, Taiwan.

The subjects were not be allowed to eat until 4 hours post dose.

The pharmacokinetics were measured by the procedures outlined in Example 8 with blood samples being obtained, predose, and at 0.5, 1, 1.5, 2, 2.5, 3, 4, 5, 6, 7, 8, 10, 12 and 24 hours post dose.

The purpose of the study was to determine the dose proportionality between Treatments A-D and to assess the bioequivalence between Treatments A and E.

The results of the study determined that Treatments A-D are dose proportional and Treatments A and E and bioequivalent.

The mean LD pharmacokinetic values for Treatments A and E are summarized as follows:

|  | $C_{max}$ (ng/mL) | $AUC_{0-t}$ (ng · hr/mL) | $AUC_{0-\infty}$ (ng · hr/mL) | $T_{max}$ (hour) |
| --- | --- | --- | --- | --- |
| Treatment A | | | | |
| Mean | 664.606 | 3225.528 | 3277.899 | 2.550 |
| SD | 178.6727 | 652.7447 | 657.5317 | 1.4088 |
| Minimum | 378.76 | 1879.36 | 1922.53 | 0.50 |
| Median | 656.450 | 3332.994 | 3392.601 | 2.50 |
| Maximum | 1148.64 | 4824.01 | 4894.14 | 5.00 |
| CV % | 26.88 | 20.24 | 20.06 | 55.25 |
| Geometric mean | 641.571 | 3159.217 | 3211.629 | 2.077 |
| Treatment E | | | | |
| Mean | 636.216 | 3115.380 | 3166.765 | 2.788 |
| SD | 135.2782 | 579.6287 | 596.7841 | 1.3199 |
| Minimum | 337.75 | 1906.61 | 1935.96 | 0.50 |
| Median | 620.385 | 3095.344 | 3138.750 | 2.720 |
| Maximum | 974.04 | 4538.60 | 4622.80 | 5.00 |
| CV % | 21.26 | 18.61 | 18.85 | 47.35 |
| Geometric mean | 622.042 | 3062.886 | 3112.110 | 2.398 | n = 40

Figure 15:
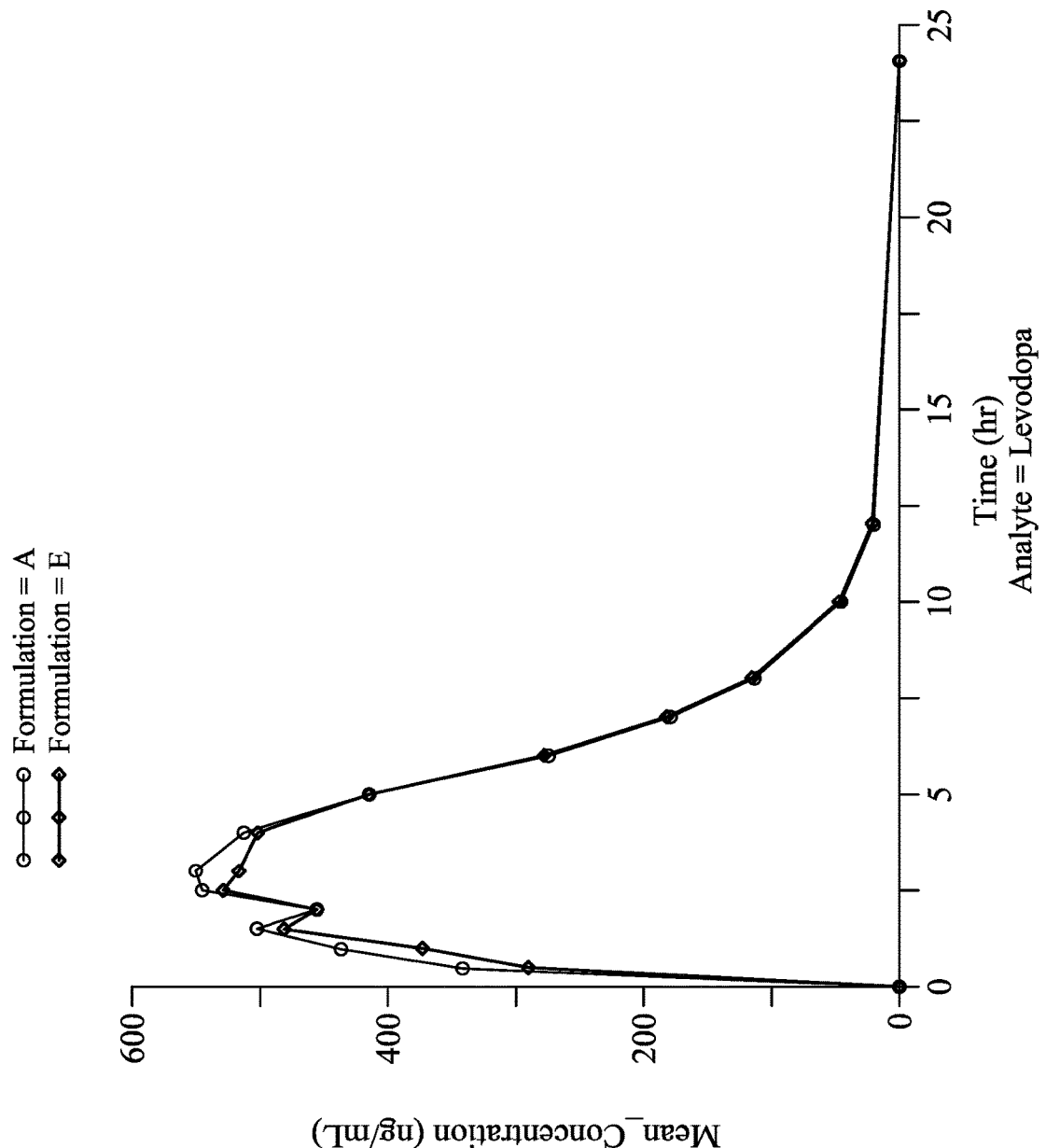
FIG. 15 shows the in vivo levodopa plasma profiles for formulations A and E tested in Example 10.

The mean LD plasma profiles for Treatments A and E are shown in FIG. 15. The mean time above 50% $C_{max}$ for Treatment A and E are 4.986 hours (SD 0.9711) and 4.945 (SD 0.9521) respectively.

The mean CD pharmacokinetic values for Treatments A and E are summarized as follows:

|  | $C_{max}$ (ng/mL) | $AUC_{0-t}$ (ng · hr/mL) | $AUC_{0-\infty}$ (ng · hr/mL) |
| --- | --- | --- | --- |
| Treatment A | | | |
| Mean | 153.484 | 824.626 | 830.253 |
| SD | 68.0712 | 313.1209 | 314.1179 |
| Minimum | 57.56 | 278.05 | 283.52 |
| Median | 141.120 | 821.550 | 826.402 |
| Maximum | 434.99 | 1632.01 | 1641.30 |
| CV % | 44.35 | 37.97 | 37.83 |
| Geometric mean | 142.080 | 767.395 | 773.176 |
| Treatment E | | | |
| Mean | 154.918 | 797.201 | 803.160 |
| SD | 63.0400 | 313.7050 | 314.2826 |
| Minimum | 40.02 | 161.65 | 170.30 |
| Median | 152.705 | 604.500 | 810.419 |
| Maximum | 316.12 | 1597.47 | 1607.14 |
| CV % | 40.69 | 39.35 | 39.13 |
| Geometric mean | 141.310 | 727.619 | 734.346 | n = 40

Figure 16:
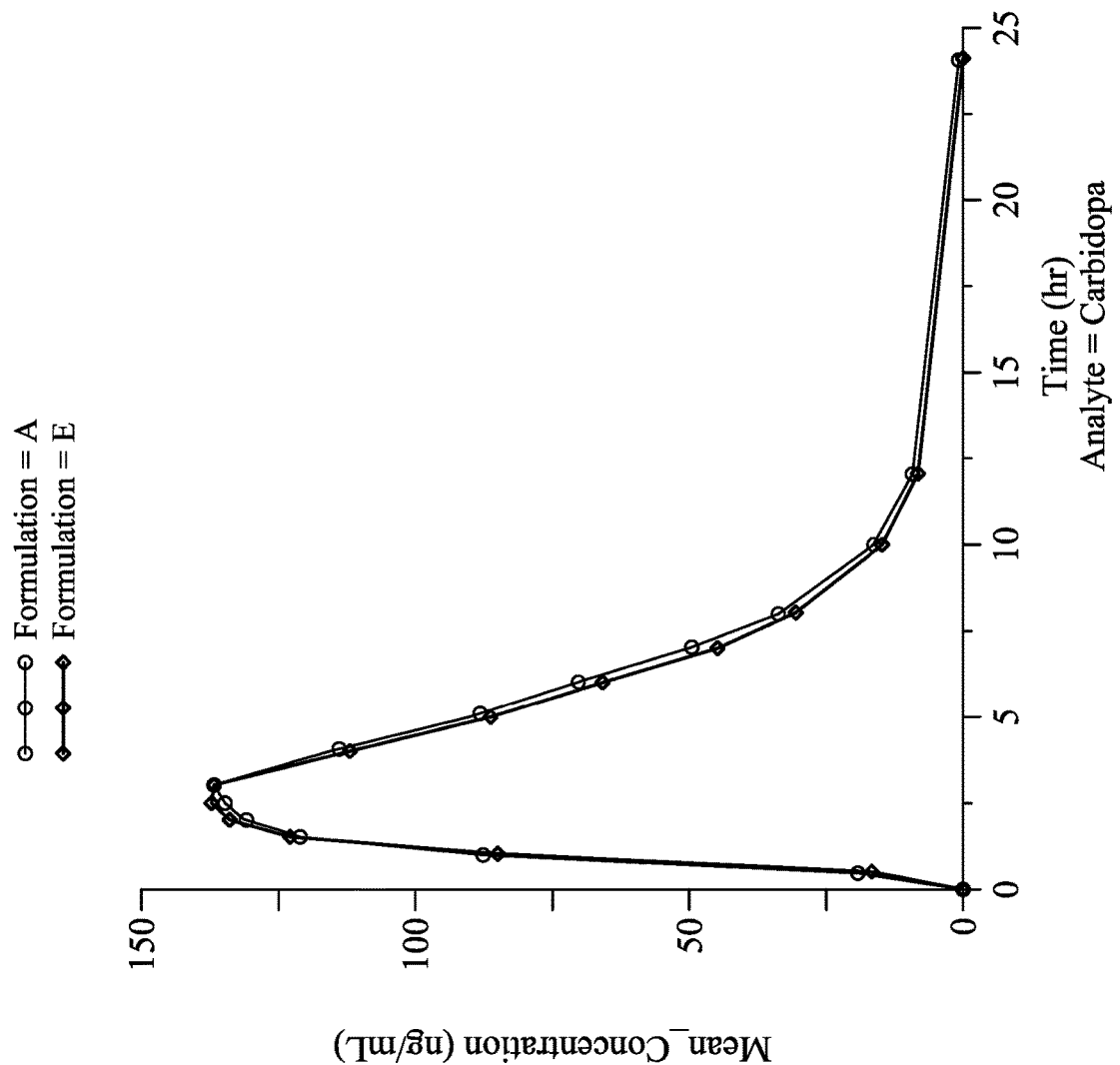
FIG. 16 shows the in vivo carbidopa plasma profiles for formulations A and E tested in Example 10.

The mean CD plasma profiles for Treatments A and E are shown in FIG. 16.

Example 11

630 PD patients with motor fluctuations were enrolled in a randomized double blind, active-controlled study to compare the safety and efficacy of the dosage forms described in Example 7 with a commercially available IR CD-LD tablet such as SINEMET® or a U.S. FDA approved AB rated generic of SINEMET®. The dosage forms described in Example 7 was administered to approximately 256 subjects with PD in a multicenter, randomized, double-blind, double dummy, active-controlled, parallel-group study. The study consisted of a 3-week, open-label IR CD-LD dose adjustment period using the commercially available IR CD-LD tablet such as SINEMET® or a U.S. FDA approved AB rated generic; a 4-week, open-label period for conversion to the dosage form of Example 7; followed by a 13-week double-blind treatment period with subjects randomized in approximately a 1:1 ratio, stratified by center, to received either the dosage form of Example 7, with matching IR, CD-LD placebo or IR CD-LD with matching Example 7 placebo.

Subjects were allowed to continue taking permitted non-CD-LD-based PD medications throughout the study if documented in their prestudy regimen and if dosing regimens have been stable for at least 4 weeks prior to Visit 1. A "stable dosing regimen" means no change in dose or in dosing frequency.

Within 4 weeks following the screening visit, eligible subjects completed their PD Diaries on each of the 3 consecutive days immediately prior to Visit 1.

Following Visit 1, qualified subjects entered a 3-week, open-label IR CD-LD treatment period allowing for dose adjustment. The dosing regimen of IR CD-LD could be adjusted during the dose adjustment period to minimize "Off" time without causing troublesome dyskinesia. The doses and regimens of the subject's other non-CD-LD PD medications (dopamine agonists, MAO-B inhibitors, amantadine, and anticholinergics) remained stable throughout this study. Any adjustments to the IR CD-LD dosing regimen were done in consultation with the Investigator or qualified site personnel and recorded. The IR CD-LD dosing regimen was stable for at least 5 days prior to returning for Visit 2. Rescue with additional or modified doses of concomitant PD medications or with use of CD-LD products other than the dispensed study medications was not permitted and triggered discontinuation from the study. Subjects completed their 3-day PD Diaries on each of the 3 consecutive days immediately prior to Visit 2.

Following completion of the IR CD-LD dose adjustment period, subjects began a 4-week open-label period for conversion to IPX203 (Example 7). The initial dosing regimen of IPX203 were based on the most frequent dose of the subject's dosing regimen of IR CD-LD at the end of the dose adjustment period (Visit 2). The following table outlines the recommended conversion:

| Most Frequent IR CD-LD Unit Dose (mg) | Recommended Starting IPX203 Daily Dosing Regimen CD-LD (mg) Every 8 Hours |
| --- | --- |
| 25-100[a] | 70-280 mg (2 × 35-140 mg) |
| >25-100-37.5-150 | 105-420 mg (3 × 35-140 mg) |

-continued

| Most Frequent IR CD-LD Unit Dose (mg) | Recommended Starting IPX203 Daily Dosing Regimen CD-LD (mg) Every 8 Hours |
|---|---|
| >37.5-150-50-200 | 140-560 mg (4 × 35-140 mg) |
| >50-200 | 175-700 mg (5 × 35-140 mg) |

It was recommended that IPX203 should be dosed approximately every 8 hours with the exception that subjects who were receiving a total daily dose of less than 125-500 mg IR CD-LD at the end of the dose adjustment period were initially administered every 12 hours. The dosing interval was reduced to approximately every 8 hours if the subject did not achieve an acceptable duration of effect. The dosing regimen of IPX203 could be adjusted during the dose conversion period to achieve the optimal balance of efficacy and tolerability (minimize "Off" time without causing troublesome dyskinesia or other dopaminergic side effects). The doses and regimens of the subject's other non-CD-LD PD medications (dopamine agonists, MAO-B inhibitors, amantadine, and anticholinergics) remained stable throughout this study. The subjects were on a stable dosing regimen of IPX203 (no change in dose or in dosing frequency) for at least 5 days prior to returning for Visit 4. Any adjustments to the IPX203 dosing regimen was done in consultation with the Investigator or qualified site personnel and will be recorded. Rescue with additional or modified doses of concomitant PD medications or with use of CD-LD products other than the dispensed study medications was not permitted and triggered discontinuation from the study. Subjects returned to the clinic in 2 weeks for Visit 3 followed by Visit 4, 2 weeks later. Subjects completed their 3-day PD Diaries on each of the 3 consecutive days immediately prior to Visit 4.

506 subjects successfully completed the IPX203 dose conversion period and were randomized in approximately a 1:1 ratio, at Visit 4 into one of two parallel treatment arms of IPX203 (with matching IR CD-LD placebo) or IR CD-LD (with matching IPX203 placebo). The subjects underwent 13 weeks of double-blind maintenance therapy with the stable dosing regimen established at the end of Week 3 (Visit 2) for IR CD-LD and at the end of Week 7 (Visit 4) for IPX203. Rescue with additional or modified doses of concomitant PD medications or with use of CD-LD products other than the dispensed study medications was not permitted and triggered discontinuation from the study. Subjects returned to the clinic for 3 visits (Visit 5 [week 10], Visit 6 [week 15], and Visit 7 [week 20]) and completed their 3-day PD Diaries on each of the 3 consecutive days immediately prior to each of these visits.

Inclusion Criteria
  Male or female subjects diagnosed at age ≥40 years with PD, consistent with the United Kingdom Parkinson's Disease Society Brain Bank Diagnostic Criteria and who are being treated with stable regimens of CD-LD but experiencing motor fluctuations.
  Hoehn and Yahr Stages 1, 2, 3, or 4 in the "On" state (part of Movement Disorders Society version of the Unified Parkinson's Disease Rating Scale [MDS-UPDRS] Part III).
  Montreal Cognitive Assessment (MoCA) score ≥24 at Screening Visit in "On" state.
  By history, for the 4 weeks prior to screening, the subject experienced daily "wearing-off" episodes with periods of bradykinesia in combination with at least one of rest tremor or rigidity, experiences an "Off" state upon awakening on most mornings, and reported an average of at least 2.5 cumulative hours per day of "Off" time during the waking hours.
  Able to differentiate "On" state from "Off" state as determined by at least 75% concordance with a trained rater in "On/Off" ratings for 8 ratings over a 4-hour training period. The concordance must include at least 1 "On" and 1 "Off" rating and must be achieved within two 4-hour training sessions.
  At Visit 1, review of the 3-day PD Diaries confirmed the following: that the subject was able to properly complete the Diaries with valid entries; and that the subject had an average of at least 2.5 hours per day of "Off" time during waking hours over the 3 days with at least 1.5 hours of cumulative "Off" time on each day.
  Responsive to CD-LD therapy and currently being treated on a stable regimen with CD-LD for at least 4 weeks prior to Visit 1 and:
    Required at least 100 mg of LD from IR CD-LD for the first morning dose;
    Required a total daily dose of at least 400 mg of LD and takes a maximum total daily dose of 2400 mg LD, from IR CD-LD alone or IR CD-LD in combination with a single daily bedtime dose of CR CD-LD;
    Had a dosing frequency of 4 to 9 times daily of CD-LD;
    By history, typically experienced an "On" response with the first dose of IR CD-LD of the day, but the efficacy of this dose typically lasts less than 4 hours.
  At screening, the subject had predictable "Off" periods defined by a score of 1 or 2 on Item #4.5 (Complexity of Motor Fluctuations) of the MDS-UPDRS Part IV B (Motor Fluctuations).
  At screening, the MDS-UPDRS Part III total score in the "Off" state was at least 20 units.
Exclusion Criteria
  Used any doses of controlled-release (CR) CD-LD apart from a single daily bedtime dose within 4 weeks prior to Visit 1.
  Used any dose of RYTARY® for the past 4 weeks prior to Visit 1 or were considered RYTARY® failures for reasons of efficacy or safety.
  Had prior neurosurgical treatment for PD or if such procedure was planned or anticipated during the study period.
  Allergic to any excipient in the study drugs.
  History of glaucoma with intraocular pressures that were elevated despite appropriate medical management.
  History of seizure or epilepsy and experienced at least 1 seizure during the past 12 months or had not been compliant with medically recommended therapy or visits.
  History of myocardial infarction with residual atrial, nodal, or ventricular arrhythmias that were not controlled with medical and/or surgical interventions. A recent (≤12 months) history of myocardial infarction with secondary arrhythmias was exclusionary regardless of the therapeutic control.
  Received within 4 weeks of screening or planning to take during participation in the clinical study:
    Any doses of a CR CD-LD apart from a single daily bedtime dose, any doses of RYTARY®, additional CD (e.g., LODOSYN®) or benserazide (e.g., SERAZIDE®), or catechol-O-methyl transferase inhibitors (entacapone or tolcapone) or medications containing these inhibitors (STALEVO®), Nonselective monoamine oxidase inhibitors (MAOI), apomorphine, or antidopaminergic agents, including antiemetics.

Subjects who had previously participated in an IPX203 study.

Criteria for Evaluation:

There were two types of baselines used in the evaluations and could be either the study entry baseline done at Visit 1 (study entry visit) or the double blind baseline defined as assessments done at Visit 4 (randomization visit).

The primary secondary endpoints were examined for the following subgroups:

Age: <65, ≥65 years old at study entry
Sex: Males, Females
Race: Caucasians, non-Caucasians.

Additionally the following subgroups were examined:
Region: North America or Europe
Ethnicity: Hispanic, Non-Hispanic or Unknown
Concomitant medications: the following non-exclusive subgroups were defined for subjects taking concomitant medications of the following categories:
  Amantadine
  Selective MAOB inhibitors
  Anticholinergic PD medications
  Dopamine agonists
  Other
Weight: <75 kg or ≥75 kg
Body Mass Index (BMI): <25 kg/m$^2$ or ≥25 kg/m$^2$
PD duration at screening: <8 years or ≥8 years
Age of PD onset: <65 years or ≥65 years
"Good On" time at study entry: <9 hours per day or ≥9 hours per day
"Off" time at study entry: average <6 hours per day or ≥6 hours per day.

Efficacy:

Primary endpoint: Change from baseline in "Good on" time in hours per day, averaged over the PD Diary days, at the end of double-blind treatment period (Visit 7 or early termination). "Good on" time is derived from the 3-day PD Diaries and is defined as the sum of "On" time without dyskinesia and "On" time with nontroublesome dyskinesia.

Key Secondary Endpoints:
  Change from baseline in "Off" time in hours per day, averaged over the PD Diary days at the end of double-blind treatment period (Visit 7 or early termination);
  Proportion of subjects with either "much improved" or "very much improved" in PGI-C scores at the end of double-blind treatment period (Visit 7 or early termination);
  Change from baseline in the MDS-UPDRS Part III at the end of double-blind treatment period (Visit 7 or early termination); and/or
  Change from baseline in the sum of MDS-UPDRS Parts II and III at the end of double blind treatment period (Visit 7 or early termination).

Additional Endpoints:

The following endpoints were evaluated (at the post-randomization visits) as change from baseline (Visit 4) as well as change from the study entry (Visit 1), when applicable, by visits:
  Percent "Off" time during waking hours derived from the 3-day PD Diaries—Average duration of each continuous "Good On" and each continuous "On";
  Average duration of each continuous "Good On" and each continuous "On";
  Hours of (1) "Off" time (from Visit 1), (2) "Good On" time (from Visit 1), (3) "On" time with dyskinesia, (4) "On" time with troublesome dyskinesia, and (5) "On" time with nontroublesome dyskinesia, and (6) asleep time derived from the 3-day PD Diaries;
  Proportion of subjects with an improvement in "Good on" time of at least 1, 1.5, 2, 2.5, and 3 hours;
  Proportion of subjects with a reduction in "Off" time of at least 0.5, 1, 1.5, 2, 2.5, and 3 hours;
  Proportions of subjects who are "On" upon awakening and "Good On" upon awakening;
  Average time to "On" upon awakening;
  Change from baseline in the average number of motor fluctuations per day averaged over the PD Diary days. A motor fluctuation is defined as a change from "Off" to "On" state or from "On" to "Off" state;
  MDS-UPDRS total score (sum of Parts I, II, III, and IV) and Parts I, II, and IV separately;
  MDS-UPDRS Part III and Parts II+III combined (from Visit 1);
  MDS-UPDRS Part II Question 2.9;
  39-Item Parkinson's Disease Questionnaire ("PDQ-39") total score and individual domain scores;
  Non-Motor Symptom Assessment Scale (NMSS) total score and individual domains;
  Parkinson's Disease Sleep Scale 2 (PDSS-2) total score and individual domains;
  PDSS-2 items 9, 10, 11, 12, and 13 combined;
  Parkinson Anxiety Scale (PAS) total score and individual domains;
  Patient Global Impression of Severity (PGI-S);
  Proportion of subjects with either "severely ill" or "extremely severely ill" on the PGI-S—Clinical Global Impression of Severity (CGI-S);
  Proportion of subjects with either "severely ill" or "among the most extremely ill of subjects" on the CGI-S;
  Patient Global Impression of Change (PGI-C) scores;
  Clinical Global Impression of Change (CGI-C) scores; and
  Proportion of subjects with either "much improved" or "very much improved" on the CGI-C.

Adverse events were monitored and recorded. Patients were administered a Gastroparesis Cardinal Symptom Index (GCSI) questionnaire at various time points throughout the study.

Unless otherwise described the evaluations followed the general procedure outline previously in Example 8 and 9.

Awakening from nocturnal sleep was defined as having at least one "asleep" status post-midnight and 3 consecutive hours of non-asleep after the post-midnight "asleep" episode. Those subjects who did not meet the above 3 consecutive hours of non-asleep were considered non-classifiable. Likewise, those who did not have any "asleep" status after 12:00 AM were considered non-classifiable.

Because the PD diaries started at 6:00 AM, the consideration of "3 consecutive hours of non-asleep" started at 6:00 AM and having an "asleep" status was not required. Thus, for Diary Day −3, awakening from nocturnal sleep was defined as having 3 consecutive hours of non-asleep after 6:00 AM.

Time of awakening was defined as the start of the 3 consecutive hours of non-asleep in the definition above. The number and percentage of subjects with 0 days, 1 day, 2 days, and 3 days in "On" and in "Good on" states in the first half-hour interval upon awakening from nocturnal sleep were summarized by visit (Visits 4, 5, 6, and 7 or ET) and treatment group. Subjects who were non-classifiable on at least one day in the PD Diary for a visit were excluded from analysis for that visit.

The baseline characteristics and demographics of the subjects enrolled in the study are:

| CHARACTERISTIC | IPX 203 (n = 256) | IR CD-LD (n = 250) |
|---|---|---|
| Mean Age ± SD (years) | 66.1 ± 9.02 | 66.5 ± 8.85 |
| Gender, n | | |
| Males | 159 (62.1%) | 177 (70.8%) |
| Females | 97 (37.9%) | 73 (29.2%) |
| Race | | |
| American Indian or Alaska Native | 3 (1.2%) | 0 |
| Asian | 5 (2.0%) | 3 (1.2%) |
| Black or African American | 2 (0.8%) | 3 (1.2%) |
| White | 244 (95.3%) | 242 (96.8%) |
| Unknown or not reported | 2 (0.8%) | 2 (0.8%) |
| Ethnicity | | |
| Non-Hispanic | 223 (87.1%) | 215 (86.0%) |
| Hispanic or Latino | 32 (12.5%) | 31 (12.4%) |
| Not Reported | 1 (0.4%) | 4 (1.6%) |
| Mean BMI (kg/m$^2$) ± SD | 27.41 ± 5.07 | 27.30 ± 4.68 |
| Hoehn & Yahr 2/3/4 (%) | 89.5% | 91.6% |
| Screening Montreal Cognitive Assessment ("MoCA") score: Mean | 27.3 | 27.2 |
| Age of Onset of PD (y): Mean (min-max) | 57.7 (40-83) | 58.3 (34-83) |
| MDS-UPDRS Part III (On): mean ± SD | 24.7 ± 15.96 | 24.9 ± 15.56 |
| MDS-UPDRS Part III (Off): mean ± SD | 45.5 ± 13.96 | 45.6 ± 14.11 |

The daily frequency of dosing in the IPX203 and JR CD-LD stable regimens used in the double-blind period (Visits 4-7) is shown in the following tables:

| Total Daily Dose (mg) | IPX203 (N = 256) | IR CD-LD (N = 250) | IPX203 to IR CD-LD Ratio |
|---|---|---|---|
| Mean ± SD | 1488.05 ± 592.8 | 856.9 ± 378.7 | 7.79 (0.5) |
| Median | 1400.0 | 800.0 | 1.70 |
| Min-max | 420-3360 | 400-2100 | 0.6-3.5 |

| Dose Frequency per Day | IPX203 | IR CD-LD |
|---|---|---|
| Mean ± SD | 3.0 ± 0.42$^a$ | 5.1 ± 1.2 |
| Median | 3.0 | 5.0 |
| Min-max | 2-4 | 3-10 |

$^a$n = 16 dosed twice a day (BID), and n = 28 dosed four times a day (QID).

A summary of the primary endpoint, Change from Baseline in "Good On" Time (hours) is shown in the following table:

| Visit | Statistic | IPX203 (N = 249) At Visit | Change from Baseline | IR CD-LD (N = 246) At Visit | Change from Baseline |
|---|---|---|---|---|---|
| Visit 4 | n | 249 | | 246 | |
| Baseline | Mean | 11.67 | | 11.72 | |
| | SD | 2.943 | | 2.759 | |
| | Median | 12.00 | | 11.67 | |
| | Min | 0.5 | | 1.8 | |
| | Max | 18.8 | | 18.0 | |
| Visit 5 | n | 237 | 237 | 235 | 235 |
| | Mean | 11.15 | −0.55 | 11.04 | −0.66 |
| | SD | 3.234 | 2.504 | 2.852 | 3.108 |
| | Median | 11.50 | −0.67 | 11.17 | −0.67 |
| | Min | 0.0 | −12.0 | 0.0 | −9.5 |
| | Max | 18.3 | 6.4 | 18.3 | 10.3 |
| | Missing | 12 | 12 | 11 | 11 |
| Visit 6 | n | 222 | 222 | 227 | 227 |
| | Mean | 11.35 | −0.47 | 10.85 | −0.87 |
| | SD | 3.053 | 2.519 | 2.859 | 3.172 |
| | Median | 11.67 | −0.33 | 10.67 | −0.83 |
| | Min | 0.0 | −9.7 | 0.0 | −9.0 |
| | Max | 19.3 | 7.2 | 18.3 | 9.8 |
| | Missing | 27 | 27 | 19 | 19 |
| Visit 7/ET | n | 235 | 235 | 241 | 241 |
| | Mean | 11.35 | −0.39 | 10.77 | −0.97 |
| | SD | 3.065 | 2.706 | 2.775 | 3.081 |
| | Median | 11.50 | −0.33 | 10.83 | −1.00 |
| | Min | 0.0 | −9.7 | 1.5 | −9.3 |
| | Max | 17.7 | 8.5 | 17.0 | 8.0 |
| | Missing | 14 | 14 | 5 | 5 |

A statistical analysis of the primary endpoint, Change from Baseline in "Good On" Time (hours) to Visit 7/End of Treatment (ET) is as follows:

| Statistic | IPX203 (N = 249) | IR CD-LD (N = 246) | Difference IPX203-IR CD-LD |
|---|---|---|---|
| LS Mean | −0.50 | −1.03 | 0.53 |
| Standard Error | 0.183 | 0.183 | 0.226 |
| 95% Confidence Intervals | −0.86, −0.14 | −1.39, −0.67 | 0.09, 0.97 |
| p-value (a) | | | 0.194 |

Figure 17:
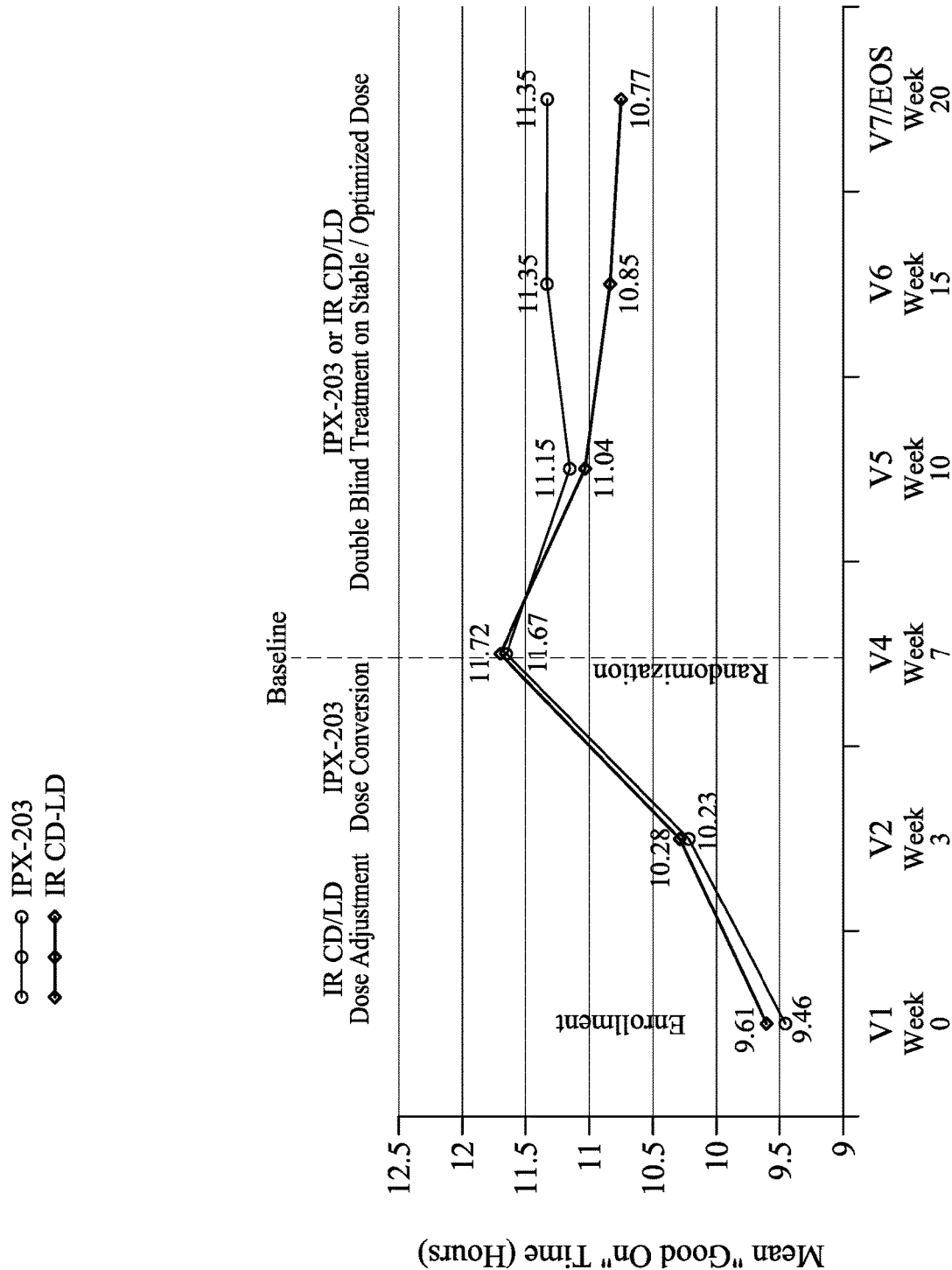
FIG. 17 shows the improvement in "Good On" time from baseline to the end of the study described in Example 11.

FIG. 17 is a graph of the following data points showing the improvement in "Good On" time from baseline to the end of the study:

| | Week 0 Visit 1 | Week 3 Visit 2 | Week 7 Visit 4 | Week 10 Visit 5 | Week 15 Visit 6 | Week 20 Visit 7 | p-value |
|---|---|---|---|---|---|---|---|
| IPX203 | 9.46 | 10.23 | 11.67 | 11.15 | 11.35 | 11.35 | 0.0194 |
| IR CD-LD | 9.61 | 10.28 | 11.72 | 11.04 | 10.85 | 10.77 | |

This data shows the treatment in accordance with the present invention (IPX203 dosed on average 3 times per day) resulted in at least 0.5 more hours (0.53 hours) of "Good On" time than IR CD-LD (dosed on average 5 times per day) when comparing change from baseline (Week 7) in both study arms. The data also showed a LS mean improvement from Visit 1 to Visit 7 of 1.76 hours for the IPX203 treatment and 1.06 hours for the IR CD-LD treatment.

A statistical analysis of the endpoint, "Good On" Time (hours) per dose at Visit 7/ET is as follows:

| Statistic | IPX203 (N = 249) | IR CD-LD (N = 246) | Difference IPX203-IR CD-LD |
|---|---|---|---|
| LS Mean | 3.76 | 2.21 | 1.55 |
| Standard Error | 0.074 | 0.074 | 0.091 |
| 95% Confidence Intervals | 3.62, 3.91 | 2.07, 2.36 | 1.37, 1.73 |
| p-value (a) | | | <0.0001 |

Figure 18:
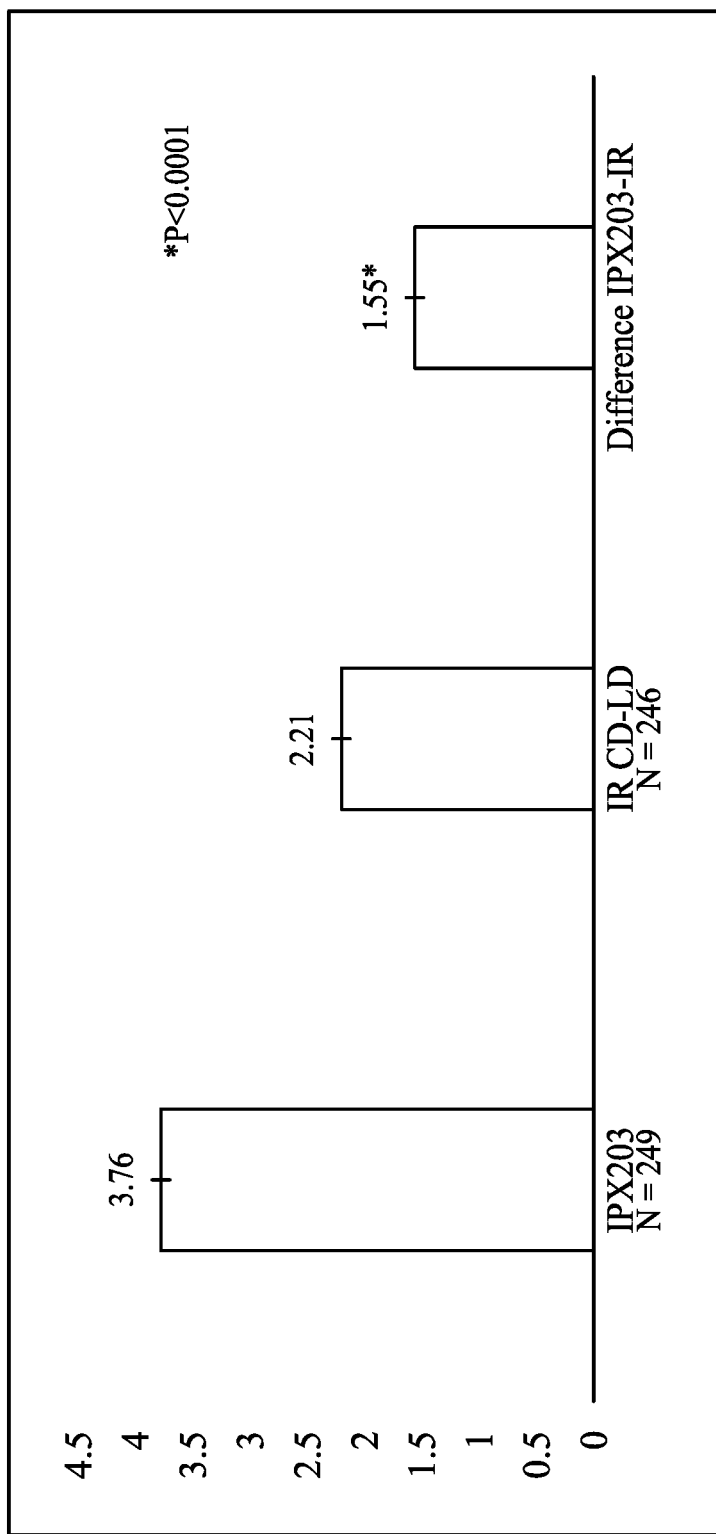
FIG. 18 shows the improvement in "Good On" time per dose at Visit 7 for the study described in Example 11.

FIG. 18 is a graph of the above "Good On" Time per dose.

A summary of the secondary endpoint, Change from Baseline in "Off" Time (hours) is shown in the following table:

| Visit | Statistic | IPX203 (N = 249) At Visit | Change from Baseline | IR CD-LD (N = 246) At Visit | Change from Baseline |
|---|---|---|---|---|---|
| Visit 4 | n | 249 | | 246 | |
| Baseline | Mean | 3.95 | | 4.02 | |
| | SD | 2.524 | | 2.466 | |
| | Median | 3.67 | | 3.71 | |
| | Min | 0.0 | | 0.0 | |
| | Max | 13.0 | | 13.7 | |
| Visit 5 | n | 237 | 237 | 235 | 235 |
| | Mean | 4.32 | 0.37 | 4.68 | 0.66 |
| | SD | 2.705 | 2.364 | 2.969 | 2.998 |
| | Median | 4.08 | 0.00 | 4.50 | 0.50 |
| | Min | 0.0 | −8.8 | 0.0 | −11.6 |
| | Max | 12.3 | 11.7 | 14.8 | 10.3 |
| | Missing | 12 | 12 | 11 | 11 |
| Visit 6 | N | 222 | 222 | 227 | 227 |
| | Mean | 4.21 | 0.31 | 4.83 | 0.82 |
| | SD | 2.709 | 2.190 | 2.857 | 3.090 |
| | Median | 4.00 | 0.29 | 4.67 | 0.83 |
| | Min | 0.0 | −6.0 | 0.0 | −11.6 |
| | Max | 16.5 | 8.2 | 18.2 | 9.8 |
| | Missing | 27 | 27 | 19 | 19 |
| Visit 7/ET | N | 235 | 235 | 241 | 241 |
| | Mean | 4.18 | 0.29 | 4.75 | 0.76 |
| | SD | 2.833 | 2.235 | 2.884 | 2.901 |
| | Median | 4.00 | 0.00 | 4.33 | 0.83 |
| | Min | 0.0 | −5.3 | 0.0 | −9.0 |
| | Max | 16.8 | 8.0 | 15.0 | 8.0 |
| | Missing | 14 | 14 | 5 | 5 |

A statistical analysis of the secondary endpoint, Change from Baseline in "Off" Time (hours) to Visit 7/ET is as follows:

| Statistic | IPX203 (N = 249) | IR CD-LD (N = 246) | Difference IPX203-IR CD-LD |
|---|---|---|---|
| LS Mean | 0.38 | 0.86 | −0.48 |
| Standard Error | 0.172 | 0.171 | 0.214 |
| 95% Confidence Intervals | 0.04, 0.71 | 0.52, 1.19 | −0.90, −0.06 |
| p-value (a) | | | 0.0252 |

Figure 19:
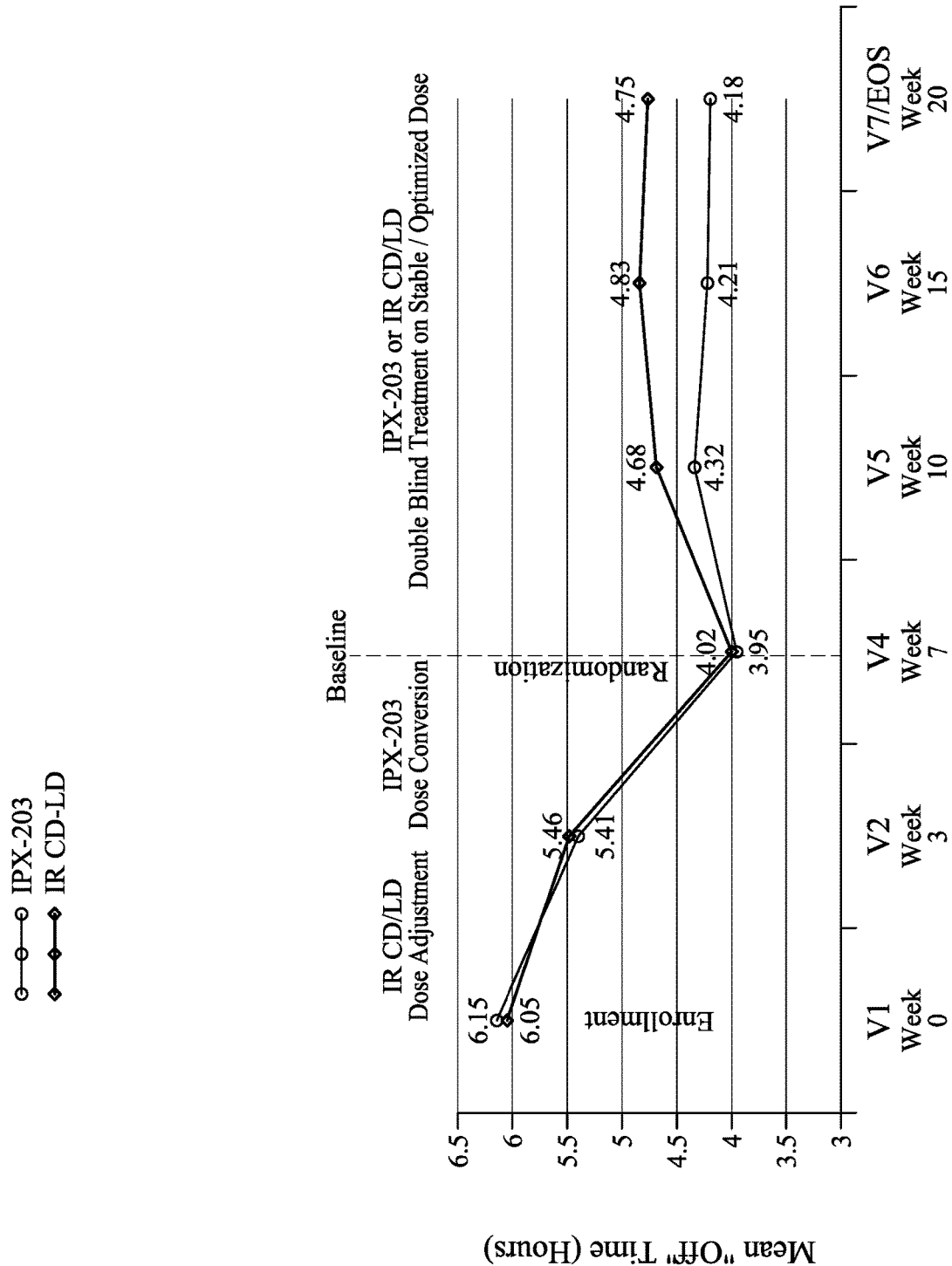
FIG. 19 shows the reduction in "Off" time from baseline to the end of the study described in Example 11.

FIG. 19 is a graph of the following data points showing the reduction in "Off" time from baseline to the end of the study:

| | Week 0 Visit 1 | Week 3 Visit 2 | Week 7 Visit 4 | Week 10 Visit 5 | Week 15 Visit 6 | Week 20 Visit 7 | p-value |
|---|---|---|---|---|---|---|---|
| IPX203 | 6.15 | 5.41 | 3.95 | 4.32 | 4.21 | 4.18 | 0.0252 |
| IR-CR/LD | 6.05 | 5.46 | 4.02 | 4.68 | 4.83 | 4.75 | |

This data shows the treatment in accordance with the present invention (IPX203 dosed on average 3 times per day) resulted in significantly less "Off" time or about 0.5 hours (0.48 hours) of "Off" time compared to IR CD-LD (dosed on average 5 times per day) when comparing change from baseline (Week 7) in both study arms.

The analysis of the data showed a greater improvement (lesser increase) in the mean percent "Off" time during waking hours from Visit 4 to Visit 7 for subjects receiving the present invention (IPX203 dosed on average 3 times per day compared to IR CD-LD (dosed on average 5 times per day). Specifically, the mean change in percent "Off" time during waking hours from Visit 4 to Visit 7 for the present invention is 1.75 and for the IR CD-LD is 4.55.

The statistical analysis of the percent "Off" time during waking hours from Visit 4 to Visit 7 is a follows:

| Statistic | IPX203 (N = 249) | IR CD-LD (N = 246) | Difference IPX203-IR CD-LD |
|---|---|---|---|
| LS Mean | 2.26 | 5.20 | −2.94 |
| Standard Error | 1.044 | 1.042 | 1.301 |
| 95% Confidence Intervals | 0.21, 4.32 | 3.15, 7.26 | −5.49, −0.38 |
| p-value (a) | | | 0.0246 |

The above analysis shows the percent "Off" time during waking hours increased less in the IPX203 group when compared to the IR CD-LD group.

The analysis of the data also showed a greater improvement (lesser decrease) in the average duration of continuous "Good On" intervals and continuous "On" intervals from Visit 4 to Visit 7 for subjects receiving the present invention (IPX203 dosed on average 3 times per day compared to JR CD-LD (dosed on average 5 times per day). Specifically, the mean change for continuous "Good On" interval from Visit 4 to Visit 7 for the present invention is −0.07 and for the JR CD-LD is −0.98. The mean change for continuous "On" interval from Visit 4 to Visit 7 for the present invention is −0.22 and for the JR CD-LD is −0.90.

The statistical analysis of the duration of continuous "Good On" interval and duration of continuous "On" interval is a follows:

| Statistic | IPX203 (N = 249) "Good On" | IPX203 (N = 249) "On" | IR CD-LD (N = 246) "Good On" | IR CD-LD (N = 246) "On" | Difference IPX203 − IR CD-LD "Good On" | Difference IPX203 − IR CD-LD "On" |
|---|---|---|---|---|---|---|
| LS Mean | −0.12 | −0.23 | −1.04 | −0.99 | 0.92 | 0.75 |
| Standard error | 0.184 | 0.196 | 0.183 | 0.195 | 0.247 | 0.263 |
| 95% confidence interval | −0.48, 0.25 | −0.62, 0.15 | −1.40, −0.68 | −1.37, −0.60 | 0.44, 1.41 | 0.23, 1.27 |
| p-value[a] | | | | | 0.0002 | 0.0045 |

The analysis of the PD Diary data showed the following:

| State Visit/Statistic | IPX203 (N = 249) At Visit | IPX203 (N = 249) Change from Baseline | IR CD-LD (N = 246) At Visit | IR CD-LD (N = 246) Change from Baseline |
|---|---|---|---|---|
| On Without Dyskinesia | | | | |
| *Visit 4 (Baseline)* | | | | |
| n | 249 | | 246 | |
| Mean (SD) | 9.56 (4.001) | | 9.67 (3.652) | |
| Median (min, max) | 10.17 (0.0, 18.8) | | 9.83 (0.0, 17.8) | |
| *Visit 7/ET* | | | | |
| n | 235 | 235 | 241 | 241 |
| Mean (SD) | 9.16 (4.079) | −0.43 (3.071) | 8.73 (3.565) | −0.97 (3.352) |
| Median (min, max) | 9.67 (0.0, 17.5) | −0.50 (−10.7, 10.8) | 9.00 (0.0, 16.3) | −0.83 (−11.7, 10.8) |
| On with Non-troublesome Dyskinesia | | | | |
| *Visit 4 (Baseline)* | | | | |
| n | 249 | | 246 | |
| Mean (SD) | 2.11 (2.960) | | 2.05 (2.684) | |
| Median (min, max) | 0.83 (0.0, 14.7) | | 1.00 (0.0, 12.2) | |
| *Visit 7/ET* | | | | |
| n | 235 | 235 | 241 | 241 |
| Mean (SD) | 2.19 (2.935) | 0.05 (2.375) | 2.04 (2.683) | 0.00 (2.330) |
| Median (min, max) | 0.83 (0.0, 14.0) | 0.00 (−12.0, 9.3) | 0.83 (0.0, 15.2) | 0.00 (−11.0, 11.3) |
| On with Troublesome Dyskinesia | | | | |
| *Visit 4 (Baseline)* | | | | |
| n | 249 | | 246 | |
| Mean (SD) | 0.54 (1.289) | | 0.35 (0.863) | |
| Median (min, max) | 0.00 (0.0, 7.8) | | 0.00 (0.0, 5.7) | |
| *Visit 7/ET* | | | | |
| n | 235 | 235 | 241 | 241 |
| Mean (SD) | 0.60 (1.413) | 0.05 (1.200) | 0.46 (1.186) | 0.10 (0.861) |
| Median (min, max) | 0.00 (0.0, 9.0) | 0.00 (−4.8, 5.2) | 0.00 (0.0, 9.0) | 0.00 (−3.0, 4.5) |
| Asleep | | | | |
| *Visit 4 (Baseline)* | | | | |
| n | 249 | | 246 | |
| Mean (SD) | 7.85 (1.721) | | 7.91 (1.698) | |
| Median (min, max) | 7.83 (2.8, 13.2) | | 7.88 (3.7, 14.3) | |
| *Visit 7/ET* | | | | |
| n | 235 | 235 | 241 | 241 |
| Mean (SD) | 7.88 (1.707) | 0.04 (1.308) | 8.02 (1.656) | 0.11 (1.382) |
| Median (min, max) | 7.83 (2.5, 14.5) | 0.00 (−4.5, 4.6) | 8.00 (4.2, 14.2) | 0.17 (−4.8, 4.8) |

-continued

|  | IPX203 (N = 249) | | IR CD-LD (N = 246) | |
| --- | --- | --- | --- | --- |
| State Visit/Statistic | At Visit | Change from Baseline | At Visit | Change from Baseline |
| On with Dyskinesia | | | | |
| Visit 4 (Baseline) | | | | |
| n | 249 | | 246 | |
| Mean (SD) | 2.65 (3.573) | | 2.40 (3.095) | |
| Median (min, max) | 1.00 (0.0, 15.0) | | 1.17 (0.0, 15.7) | |
| Visit 7/ET | | | | |
| n | 235 | 235 | 241 | 241 |
| Mean (SD) | 2.79 (3.671) | 0.09 (2.527) | 2.50 (3.297) | 0.11 (2.592) |
| Median (min, max) | 0.83 (0.0, 15.2) | 0.00 (−12.0, 9.3) | 1.00 (0.0, 15.7) | 0.00 (−11.0, 13.0) |

The above PD Diary data showed a greater improvement with IPX203 than IR CD-LD in the following states that were recorded on the PD Diary:

(i) "On" time without dyskinesia: mean change from study entry baseline to Visit 7/ET; IPX203: 1.45 and IR CD-LD: 1.01);
(ii) "On" time with non-troublesome dyskinesia: mean change from study entry baseline to Visit 7/ET; IPX203: 0.36 and IR CD-LD: 0.13);
(iii) "On" time with troublesome dyskinesia: mean change from study entry baseline to Visit 7/ET; IPX203: 0.04 and IR CD-LD: −0.02);
(iv) "On" time with dyskinesia: mean change from study entry baseline to Visit 7/ET; IPX203: 0.41 and IR CD-LD: 0.10);
(v) "Asleep" time: mean change from study entry baseline to Visit 7/ET; IPX203: 0.05 and IR CD-LD: 0.18).

The following is a summary of the proportion of subjects who were "On" upon awakening and "Good On" upon awakening obtained from the PD Diaries:

|  | Visit 4 | | Visit 5 | | Visit 6 | | Visit 7 | |
| --- | --- | --- | --- | --- | --- | --- | --- | --- |
|  | IPX203 | IR | IPX203 | IR | IPX203 | IR | IPX203 | IR |
| % Subjects "ON" Upon Awakening | | | | | | | | |
| 0 Days | 42.7 | 42.7 | 43.4 | 50.4 | 49 | 58.4 | 46.9 | 55.5 |
| 1 Day | 18.7 | 19.7 | 18.6 | 19.2 | 20 | 17.4 | 17.1 | 20.8 |
| 2 Days | 14.1 | 15.4 | 16.8 | 14.7 | 10.5 | 10.5 | 11.4 | 7.6 |
| 3 Days | 24.5 | 22.2 | 21.2 | 15.6 | 20.5 | 13.7 | 24.6 | 16.1 |
| % Subjects "GOOD ON" Upon Awakening | | | | | | | | |
| 0 Days | 44 | 42.7 | 44.7 | 51.3 | 49.5 | 58.9 | 46.9 | 55.5 |
| 1 Day | 18.7 | 19.7 | 19.5 | 18.8 | 21 | 17.8 | 18.4 | 21.6 |
| 2 Days | 12.9 | 15.8 | 16.4 | 15.2 | 11 | 10 | 11.4 | 7.2 |
| 3 Days | 24.5 | 21.8 | 19.5 | 14.7 | 18.6 | 13.2 | 23.2 | 15.7 |

The above data shows that at Visit 7, a significant difference was noted in the percentage of subjects who were in the "On" state upon awakening for at least 1 of the 3 recorded PD Diary days: IPX203 treatment, 53.1% of the subjects versus JR CD-LD treatment 44.5% (p=0.0046). Similar differences were noted in the subjects who were in the "Good On" state upon awaking.

The following is a summary of the average time to "On" upon awakening obtained from the PD Diaries:

| Visit Evaluable Days[a] | IPX203 (N = 249) | | IR CD-LD (N = 246) | |
|---|---|---|---|---|
| | n/M (%)[b] | Mean[c] | n/M (%)[b] | Mean[c] |
| Visit 4 | | | | |
| 0 days | 0/249 | | 0/246 | |
| 1 day | 2/249 (0.8) | 1.50 | 4/246 (1.6) | 1.00 |
| 2 days | 7/249 (2.8) | 1.54 | 9/246 (3.7) | 1.72 |
| 3 days | 240/249 (96.4) | 0.89 | 233/246 (94.7) | 0.86 |
| Visit 5 | | | | |
| 0 days | 1/237 (0.4) | | 1/235 (0.4) | |
| 1 day | 1/237 (0.4) | 1.50 | 4/235 (1.7) | 1.13 |
| 2 days | 13/237 (5.5) | 1.35 | 9/235 (3.8) | 0.92 |
| 3 days | 222/237 (93.7) | 0.88 | 221/235 (94.0) | 0.99 |
| Visit 6 | | | | |
| 0 days | 2/222 (0.9) | | 1/227 (0.4) | |
| 1 day | 2/222 (0.9) | 0.25 | 2/227 (0.9) | 0.75 |
| 2 days | 11/222 (5.0) | 1.30 | 6/227 (2.6) | 1.21 |
| 3 days | 207/222 (93.2) | 1.00 | 218/227 (96.0) | 1.09 |
| Visit 7/ET | | | | |
| 0 days | 1/235 (0.4) | | 0/241 | |
| 1 day | 2/235 (0.9) | 0.00 | 1/241 (0.4) | 0.00 |
| 2 days | 5/235 (2.1) | 0.55 | 4/241 (1.7) | 1.44 |
| 3 days | 227/235 (96.6) | 0.90 | 236/241 (97.9) | 0.99 |

Abbreviations:
ET: early termination
[a] A diary day was evaluable if the subject was classifiable in terms of time of awakening and reached "On" state.
[b] n = number of subjects with the given number of evaluable days. M = number of subjects with valid diaries.
[c] Time to "On" upon awakening was averaged for each subject across available evaluable days. Then mean was calculated across subjects.

The above data shows the IPX203 treatment resulted in a shorter average time to "On" upon awaking compared with the JR CD-LD treatment. Specifically the mean change from Visit 4 to Visit 7 for IPX203 treatment was 0.01 hours and the mean change from Visit 4 to Visit 7 for JR CD-LD treatment was 0.09. This difference was not significant (p=0.1664).

The analysis of the PD Diary data showed subjects receiving the IPX203 treatment exhibited a greater improvement (lesser increase) in the average number of motor fluctuations per day from Visit 4 to Visit 7/ET when compared with those receiving JR CD-LD treatment. The mean change from Visit 4 to Visit 7/ET for the subjects receiving IPX203 treatment was 0.17 and the mean change from Visit 4 to Visit 7/ET for the subjects receiving JR CD-LD was 1.47. The following is a statistical analysis of the average number of motor fluctuations per day obtained from the subjects PD Diary collected over 3 days prior to Visit 4 and prior to Visit 7/ET.

| Statistic | IPX203 (N = 249) | IR CD-LD (N = 246) | Difference IPX203-IR CD-LD |
|---|---|---|---|
| LS Mean | 0.19 | 1.54 | −1.35 |
| Standard error | 0.145 | 0.144 | 0.190 |
| 95% confidence interval | −0.10, 0.48 | 1.25, 1.82 | −1.72, −0.97 |
| p-value | | | <0.0001 |

A summary of the secondary endpoint, MDS-UPDRS Part III Total Score, is shown in the following table:

| Visit | Statistic | IPX203 (N = 256) At Visit | Change from Baseline | IR CD-LD (N = 250) At Visit | Change from Baseline |
|---|---|---|---|---|---|
| Visit 4 | n | 256 | | 250 | |
| | Mean | 26.9 | | 27.0 | |
| | SD | 16.62 | | 16.83 | |
| | Median | 24.0 | | 24.0 | |
| | Min | 1 | | 4 | |
| | Max | 111 | | 97 | |
| Visit 5 | n | 230 | 230 | 224 | 224 |
| | Mean | 27.2 | 0.0 | 27.7 | 0.6 |
| | SD | 17.79 | 9.15 | 17.07 | 11.78 |
| | Median | 24.0 | 0.0 | 24.0 | 0.0 |
| | Min | 1 | −29 | 1 | −46 |
| | Max | 109 | 35 | 95 | 41 |
| | Missing | 26 | 26 | 26 | 26 |
| Visit 6 | n | 215 | 215 | 217 | 217 |
| | Mean | 27.2 | 0.2 | 27.2 | 0.2 |
| | SD | 18.25 | 11.03 | 16.22 | 9.34 |
| | Median | 22.0 | 1.0 | 23.0 | 0.0 |
| | Min | 1 | −40 | 3 | −41 |
| | Max | 113 | 55 | 96 | 41 |
| | Missing | 41 | 41 | 33 | 33 |
| Visit 7/ET | n | 254 | 254 | 249 | 249 |
| | Mean | 27.8 | 1.1 | 28.0 | 0.9 |
| | SD | 17.74 | 11.07 | 16.64 | 10.10 |
| | Median | 23.0 | 0.0 | 25.0 | 1.0 |
| | Min | 1 | −30 | 2 | −36 |
| | Max | 112 | 49 | 97 | 33 |
| | Missing | 2 | 2 | 1 | 1 |

The week 0 enrollment values were 29.6 for the IPX203 group and 29.7 for the JR CD-LD group.

A statistical analysis of the secondary endpoint, MDS-UPDRS Part III Total Score at Visit 7/ET is as follows:

| Statistic | IPX203 (N = 256) | IR CD-LD (N = 250) | Difference IPX203-IR CD-LD |
|---|---|---|---|
| LS Mean | 0.8 | 0.8 | 0.0 |
| Standard Error | 0.71 | 0.72 | 0.89 |
| 95% Confidence Intervals | −0.6, 2.2 | −0.6, 2.2 | −1.8, 1.7 |
| p-value (a) | | | 0.9587 |

A summary of the secondary endpoint, MDS-UPDRS Parts II and III Total Score is shown in the following table:

| Visit | Statistic | IPX203 (N = 256) At Visit | Change from Baseline | IR CD-LD (N = 250) At Visit | Change from Baseline |
|---|---|---|---|---|---|
| Visit 4 | n | 256 | | 250 | |
| | Mean | 38.9 | | 39.3 | |
| | SD | 22.20 | | 21.65 | |
| | Median | 35.5 | | 35.0 | |
| | Min | 4 | | 8 | |
| | Max | 154 | | 136 | |
| Visit 5 | n | 230 | 230 | 224 | 224 |
| | Mean | 40.0 | 0.5 | 40.4 | 1.1 |
| | SD | 24.12 | 11.15 | 21.86 | 14.61 |
| | Median | 35.0 | 0.0 | 37.0 | 0.0 |

-continued

| Visit | Statistic | IPX203 (N = 256) At Visit | Change from Baseline | IR CD-LD (N = 250) At Visit | Change from Baseline |
|---|---|---|---|---|---|
| | Min | 3 | −27 | 5 | −61 |
| | Max | 153 | 64 | 136 | 59 |
| | Missing | 26 | 26 | 26 | 26 |
| Visit 6 | n | 215 | 215 | 217 | 217 |
| | Mean | 39.9 | 0.8 | 39.7 | 0.4 |
| | SD | 24.63 | 13.07 | 20.52 | 11.68 |
| | Median | 36.0 | 1.0 | 36.0 | 0.0 |
| | Min | 2 | −41 | 6 | −57 |
| | Max | 156 | 87 | 142 | 46 |
| | Missing | 41 | 41 | 33 | 33 |
| Visit 7/ET | n | 253 | 253 | 248 | 248 |
| | Mean | 40.6 | 2.0 | 41.1 | 1.8 |
| | SD | 24.25 | 13.54 | 21.69 | 12.39 |
| | Median | 36.0 | 0.0 | 37.5 | 1.0 |
| | Min | 4 | −32 | 2 | −42 |
| | Max | 155 | 79 | 142 | 39 |
| | Missing | 3 | 3 | 2 | 2 |

The week 0 enrollment values were 42.9 for the IPX203 group and 42.9 for the JR CD-LD group.

A statistical analysis of the secondary endpoint, MDS-UPDRS Parts II and III Total Score at Visit 7/ET is as follows:

| Statistic | IPX203 (N = 256) | IR CD-LD (N = 250) | Difference IPX203-IR CD-LD |
|---|---|---|---|
| LS Mean | 1.7 | 1.8 | 0.0 |
| Standard Error | 0.87 | 0.87 | 1.11 |
| 95% Confidence Intervals | 0.0, 3.4 | 0.0, 3.5 | −2.2, 2.1 |
| p-value (a) | | | 0.9668 |

A summary of the mean change in PDQ-39 scores from Visit 4 to Visit 7/ET is provided in the following table:

| Score Statistic | IPX203 (N = 256) | IR CD-LD (N = 250) | Difference IPX203-IR CD-LD |
|---|---|---|---|
| Total Score | | | |
| LS Mean | 2.6 | 1.8 | 0.8 |
| Standard error | 1.24 | 1.25 | 1.62 |
| 95% confidence interval | 0.2, 5.0 | −0.6, 4.3 | −2.4, 4.0 |
| p-value | | | 0.6246 |
| Emotional Well-being | | | |
| LS Mean | 0.6 | −0.1 | 0.7 |
| Standard error | 0.24 | 0.24 | 0.32 |
| 95% confidence interval | 0.2, 1.1 | −0.6, 0.4 | 0.1, 1.4 |
| p-value | | | 0.0222 |

As shown by the above data, no notable differences were observed with IPX203 treatment versus the JR CD-LD treatment in the PDQ-39 total score and other individual domain scores, except a statistically significant difference was noted in favor of IPX203 treatment for the emotional well-being score.

A summary of the mean change in NMSS scores from Visit 4 to Visit 7/ET is provided in the following table:

| Score Statistic | IPX203 (N = 256) | IR CD-LD (N = 250) | Difference IPX203-IR CD-LD |
|---|---|---|---|
| Total Score | | | |
| LS Mean | 3.8 | 2.2 | 1.7 |
| Standard error | 1.64 | 1.66 | 1.96 |
| 95% confidence interval | 0.6, 7.1 | −1.1, 5.4 | −2.2, 5.5 |
| p-value$^a$ | | | 0.3963 |
| Perceptual Problems/Hallucinations | | | |
| LS Mean | 0.4 | −0.2 | 0.6 |
| Standard error | 0.16 | 0.16 | 0.22 |
| 95% confidence interval | 0.1, 0.7 | −0.5, 0.2 | 0.1, 1.0 |
| p-value | | | 0.0094 |

As shown by the above data, no notable differences were observed with IPX203 treatment versus the JR CD-LD treatment in the NMSS total score and other individual domain scores, except for a statistically significant difference was noted in perceptual problems/hallucinations.

A summary of the secondary endpoint, PGI-C summary is shown in the following table:

| Visit | PGI-C Score | IPX203 (N = 256) n/M(%) | IR CD-LD (N = 250) n/M(%) |
|---|---|---|---|
| Visit 5 | 1: Very Much Worse | 3/238 (1.3%) | 3/233 (1.3%) |
| | 2: Much Worse | 16/238 (6.7%) | 13/233 (5.6%) |
| | 3: Minimally Worse | 27/238 (11.3%) | 38/233 (16.3%) |
| | 4: No Change | 37/238 (15.5%) | 44/233 (18.9%) |
| | 5: Minimally Improved | 85/238 (35.7%) | 91/233 (39.1%) |
| | 6: Much Improved | 60/238 (25.2%) | 39/233 (16.7%) |
| | 7: Very Much Improved | 10/238 (4.2%) | 5/233 (2.1%) |
| | Missing | 18 | 17 |
| | Much or Very Much Improved (a) | 70/256 (27.3%) | 44/250 (17.6%) |
| Visit 6 | 1: Very Much Worse | 2/222 (0.9%) | 4/227 (1.8%) |
| | 2: Much Worse | 17/222 (7.7%) | 11/227 (4.8%) |
| | 3: Minimally Worse | 33/222 (14.9%) | 35/227 (15.4%) |
| | 4: No Change | 35/222 (15.8%) | 52/227 (22.9%) |
| | 5: Minimally Improved | 62/222 (27.9%) | 69/227 (30.4%) |
| | 6: Much Improved | 62/222 (27.9%) | 53/227 (23.3%) |
| | 7: Very Much Improved | 11/222 (5.0%) | 3/227 (1.3%) |
| | Missing | 34 | 23 |
| | Much or Very Much Improved (a) | 73/256 (28.5%) | 56/250 (22.4%) |
| Visit 7/ET | 1: Very Much Worse | 6/255 (2.4%) | 2/248 (0.8%) |
| | 2: Much Worse | 22/255 (8.6%) | 19/248 (7.7%) |
| | 3: Minimally Worse | 50/255 (19.6%) | 59/248 (23.8%) |
| | 4: No Change | 32/255 (12.5%) | 53/248 (21.4%) |
| | 5: Minimally Improved | 69/255 (27.1%) | 68/248 (27.4%) |
| | 6: Much Improved | 68/255 (26.7%) | 46/248 (18.5%) |
| | 7: Very Much Improved | 8/255 (3.1%) | 1/248 (0.4%) |
| | Missing | 1 | 2 |
| | Much or Very Much Improved (a) | 76/256 (29.7%) | 47/250 (18.8%) |
| Percent Difference IPX203-IR CD-LD (95% CI) | | 10.9 (3.5, 18.3) | |
| p-value (b) | | 0.0015 | |

The PGI-C scores at Visit 7, end of treatment, showed an improvement (defined as minimally improved, much improved, or very much improved) in 56.9% of the IPX203 group (dosed on average 3 times per day) vs. 46.3% in the IR CD-LD group (dosed on average 5 times per day); 29.7% showed much or very improved in the IPX203 group vs. 18.8% in the IR CD-LD group, the latter difference is statistically significant (p=0.0015).

A summary of the CGI-C scores at Visit 7/ET is shown in the following table:

| CGI-C Score | IPX203 (N = 256) n/M (%) | IR CD-LD (N = 250) n/M (%) |
|---|---|---|
| 1: Very much worse | 3/253 (1.2) | 1/247 (0.4) |
| 2: Much worse | 13/253 (5.1) | 10/247 (4.0) |
| 3: Minimally worse | 32/253 (12.6) | 35/247 (14.2) |
| 4: No change | 58/253 (22.9) | 88/247 (35.6) |
| 5: Minimally improved | 61/253 (24.1) | 65/247 (26.3) |
| 6: Much improved | 76/253 (30.0) | 43/247 (17.4) |
| 7: Very much improved | 10/253 (4.0) | 5/247 (2.0) |
| Missing | 3 | 3 |
| Much or very much improved[a] | 86/256 (33.6) | 48/250 (19.2) |
| Percent difference IPX203 − IR CD-LD (95% CI) | 14.4 (6.8, 22.0) | |
| p-value | <0.0001 | | n = number of subjects with the given CGI-C score at a visit.
M = number of subjects with CGI-C assessment at a visit.

This CGI-C data shows 58.1% subjects receiving the IPX203 treatment reported improvement in CGI-C scores (defined as minimally improved, much improved, or very much improved) compared with 45.7% subjects receiving the JR CD-LD treatment. A statistically significant proportion of subjects (p<0.0001) reported "much improved" or "very much improved" response with the IPX203 treatment (33.6% subjects) when compared with the JR CD-LD treatment (19.2% subjects).

The following table provides a summary of the primary and secondary endpoint data obtained in this study:

| Endpoints | IPX203 (N = 249) | IR CD-LD (N = 246) | Difference (IPX203 vs. IR CD-LD) | p-value |
|---|---|---|---|---|
| Primary Endpoint | | | | |
| Change from Baseline to Visit 7/ET in "Good on" Time, LS Mean | −0.50 | −1.03 | 0.53 | 0.0194[a] |
| Key Secondary Endpoints | | | | |
| Change from Baseline to Visit 7/ET in "Off" Time, LS Mean | 0.38 | 0.86 | −0.48 | 0.0252[a] |
| Percentage of Subjects with "Much improved" or "Very Much Improved" PGI-C scores at Visit 7/ET[c] | 29.7% | 18.8% | 10.9% | 0.0015[b] |
| Change from Baseline to Visit 7/ET in MDS-UPDRS Part III Score, LS Mean[c] | 0.8 | 0.8 | 0.0 | 0.9587[a] |
| Change from Baseline to Visit 7/ET in the Sum of MDS-UPDRS Part II and III Scores, LS Mean[c] | 1.7 | 1.8 | 0.0 | 0.9668[a] |
| Additional Endpoints | | | | |
| Change from Baseline to Visit 7/ET in Percent "Off" Time During Waking Hours, LS Mean | 2.26 | 5.20 | −2.94 | 0.0246[a] |
| Change from Baseline to Visit 7/ET in Average Duration of Continuous "Good On" Interval, LS Mean | −0.12 | −1.04 | 0.92 | 0.0002[a] |
| Change from Baseline to Visit 7/ET in Average Duration of Continuous "On" Interval, LS Mean | −0.23 | −0.99 | 0.75 | 0.0045[a] |
| Change from Double-Blind Baseline (Visit 4) to Visit 7/ET in Time (h) by PD Diary State[d], Mean (SD) | | | | |
| On Without Dyskinesia | −0.43 (3.071) | −0.97 (3.352) | | |
| On with Non-troublesome Dyskinesia | 0.05 (2.375) | 0.00 (2.330) | | |
| On with Troublesome Dyskinesia | 0.05 (1.200) | 0.10 (0.861) | | |
| Asleep | 0.04 (1.308) | 0.11 (1.382) | | |
| On with Dyskinesia | 0.09 (2.527) | 0.11 (2.592) | | |
| Subjects with an Improvement in "Good on" Time at Visit 7/ET[e] | | | | |
| ≥1 hour | 27.2% | 23.7% | | 0.3973 |
| ≥1.5 hours | 22.6% | 19.5% | | 0.5195 |
| ≥2 hours | 17.0% | 16.2% | | 0.8633 |
| ≥2.5 hours | 13.2% | 12.9% | | 0.9336 |
| ≥3 hours | 9.4% | 10.4% | | 0.7154 |
| Subjects with a Reduction in "Off" Time at Visit 7/ET[f] | | | | |
| ≥0.5 hour | 36.2% | 33.6% | | 0.6684 |
| ≥1 hour | 27.2% | 25.7% | | 0.8792 |
| ≥1.5 hours | 20.0% | 22.4% | | 0.4576 |

| Endpoints | IPX203 (N = 249) | IR CD-LD (N = 246) | Difference (IPX203 vs. IR CD-LD) | p-value |
|---|---|---|---|---|
| ≥2 hours | 11.9% | 18.7% | | 0.0309 |
| ≥2.5 hours | 8.1% | 11.2% | | 0.2627 |
| ≥3 hours | 5.1% | 8.3% | | 0.2161 |
| Subjects who are "On" upon Awakening at Visit 7/ET | | | | |
| 0 days | 46.9% | 55.5% | | 0.0046[g] |
| 1 day | 17.1% | 20.8% | | |
| 2 days | 11.4% | 7.6% | | |
| 3 days | 24.6% | 16.1% | | |
| Subjects who are "Good on" upon Awakening at Visit 7/ET | | | | |
| 0 days | 46.9% | 55.5% | | 0.0060[g] |
| 1 day | 18.4% | 21.6% | | |
| 2 days | 11.4% | 7.2% | | |
| 3 days | 23.2% | 15.7% | | |
| Change from Baseline to Visit 7/ET in Average Time to "On" Upon Awakening (h), LS Mean | 0.01 | 0.11 | −0.10 | 0.1664[a] |
| Change from Baseline to Visit 7/ET in Average Number of Motor Fluctuations per Day, LS Mean | 0.19 | 1.54 | −1.35 | <0.0001[a] |
| Change from Baseline to Visit 7/ET in MDS-UPDRS Scores[a,c] | | | | |
| Part I | 0.7 | 0.9 | −0.2 | 0.5549 |
| Part II | 0.9 | 0.9 | 0 | 0.9186 |
| Part IV | 0.4 | 0.3 | 0 | 0.8735 |
| Total Score | 2.8 | 2.8 | −0.1 | 0.9639 |
| Change from Baseline to Visit 7/ET in PDQ-39 Scores, LS Mean[c] | | | | |
| Total Score | 2.6 | 1.8 | 0.8 | 0.6246[a] |
| Emotional Well-being | 0.6 | −0.1 | 0.7 | 0.0222[a] |
| Change from Baseline to Visit 7/ET in NMSS Scores, LS Mean[c] | | | | |
| Total Score | 3.8 | 2.2 | 1.7 | 0.3963[a] |
| Perceptual Problems/Hallucinations | 0.4 | −0.2 | 0.6 | 0.0094[a] |
| Change from baseline to Visit 7/ET in PDSS-2 Total Scores, LS Mean[c] | 1.8 | 1.8 | 0.0 | 0.9955[a] |
| Change from baseline to Visit 7/ET in PAS Total Scores, LS Mean[c] | 0.7 | 0.0 | 0.7 | 0.1889[a] |
| Percentage of Subjects with "Severely" or "Extremely severely ill" PGI-S scores at Visit 7/ET[c] | 3.5% | 3.2% | 0.3% | 0.8574[h] |
| Percentage of Subjects with "Severely" or "Among the most extremely ill" CGI-S scores at Visit 7/ET[c] | 2.3% | 1.6% | 0.7% | 0.4824[h] |
| Percentage of Subjects with "Much improved" or "Very Much Improved" CGI-C scores at Visit 7/ET[c] | 33.6% | 19.2% | 14.4% | <0.0001[b] |
| Sensitivity Analysis of Primary Endpoint | | | | |
| Change from Baseline to Visit 7 in "Good on" Time: Completers Analysis Set (N = 220, 226), LS Mean[d] | −0.38 | −1.00 | 0.62 | 0.0072[a] |
| Change from Baseline to Visit 7 in "Good on" Time: PP Analysis Set (N = 155, 158), LS Mean | −0.43 | −0.80 | 0.38 | 0.1718[a] |
| Post-Hoc Analysis | | | | |
| "Good on" Time (h) per Dose at Visit 7/ET, LS Mean | 3.76 | 2.21 | 1.55 | <0.0001[a] |

[a] p-value for the hypothesis of equal LS Means.
[b] p-value from the Cochran-Mantel-Haenszel ("CMH") test stratified by pooled center comparing the proportion of much or very much improved subjects between the treatment groups.
[c] IPX203; N = 256 and IR CD-LD; N = 250
[d] Double-blind baseline was defined as data obtained from PD Diary collected over 3 days prior to Visit 4/Randomization.
[e] Improvement is relative to the double-blind baseline, i.e., the diary collected over 3 days prior to Visit 4/Randomization. p-values from the CMH test stratified by pooled center comparing the proportion for each level of improvement between the treatment groups at Visit 7/ET.
[f] Reduction is relative to the double-blind baseline, i.e., the diary collected over 3 days prior to Visit 4/Randomization. p-values from the CMH test stratified by pooled center comparing the proportion for each level of reduction between the treatment groups at Visit 7/ET.
[g] p-values from the "row mean scores differ" CMH test stratified by pooled center comparing the proportions of subjects between the treatment groups at Visit 7/ET.
[h] p-value from the CMH test stratified by pooled center comparing the proportion of Severely or Extremely Severely Ill subjects for PGI-S and Severely or Among the most extremely ill of subjects for CGI-S between the treatment groups.

The results show that the PD-diary based endpoint, "Good On" time decreased less in the IPX203 group (Least Square (LS) mean=0.5 hr. reduction of "Good On" time) compared to IR CD-LD group (LS mean=1.03 hr. reduction of "Good On" time). The results also show that the PD-diary based endpoint "Off" time increased less in the IPX203 group (LS mean=0.38 hr. increase in "Off" time) compared to ID CD-LD group (LS mean=0.86 hr. increase of "Off" time). These results demonstrate a better clinical outcome in the IPX203 group with statistical significance (p=0.0194 for "Good On" time and p=0.0252 for "Off" time).

Example 12

The dosage forms described in Example 7 were administered to 27 healthy male and female subjects between the ages of 18 and 55 with a body weight of at least 55 kg and body mass index of 18.5 to 30.0 kg/m² in a single site, open label, single dose, 3-treatment, 3-period, crossover study. The subjects were fasted overnight for at least 10 hours and received a single dose of 350 mg LD and 87.5 CD for each treatment separated by a 6 to 7 day washout period.

Treatment A comprised the oral administration of one capsule prepared in accordance with Example 7 containing 350 mg LD and 87.5 mg of CD with 240 mL of water approximately 30 minutes after initiating a standardized high-fat (approximately 50% of the total caloric content of the meal), high-calorie (approximately 800-1000 calories) breakfast. No additional food was allowed for at least 4 hours post dose.

Treatment B comprised the oral administration of one capsule prepared in accordance with Example 7 containing 350 mg LD and 87.5 mg CD wherein the contents of the capsule were sprinkled onto 1 tablespoon of applesauce. No additional food was allowed for at least 4 hours post dose.

Treatment C comprised the oral administration of one capsule prepared in accordance with Example 7 containing 350 mg LD and 87.5 mg CD with 240 mL of water. No food was allowed for at least 4 hours post dose.

For Treatments A and C the subjects were instructed to swallow the capsule intact and not to chew, divide or crush the tablet.

For Treatment B, the subjects were instructed to consume all the applesauce without crushing or chewing the beads.

Figure 20:
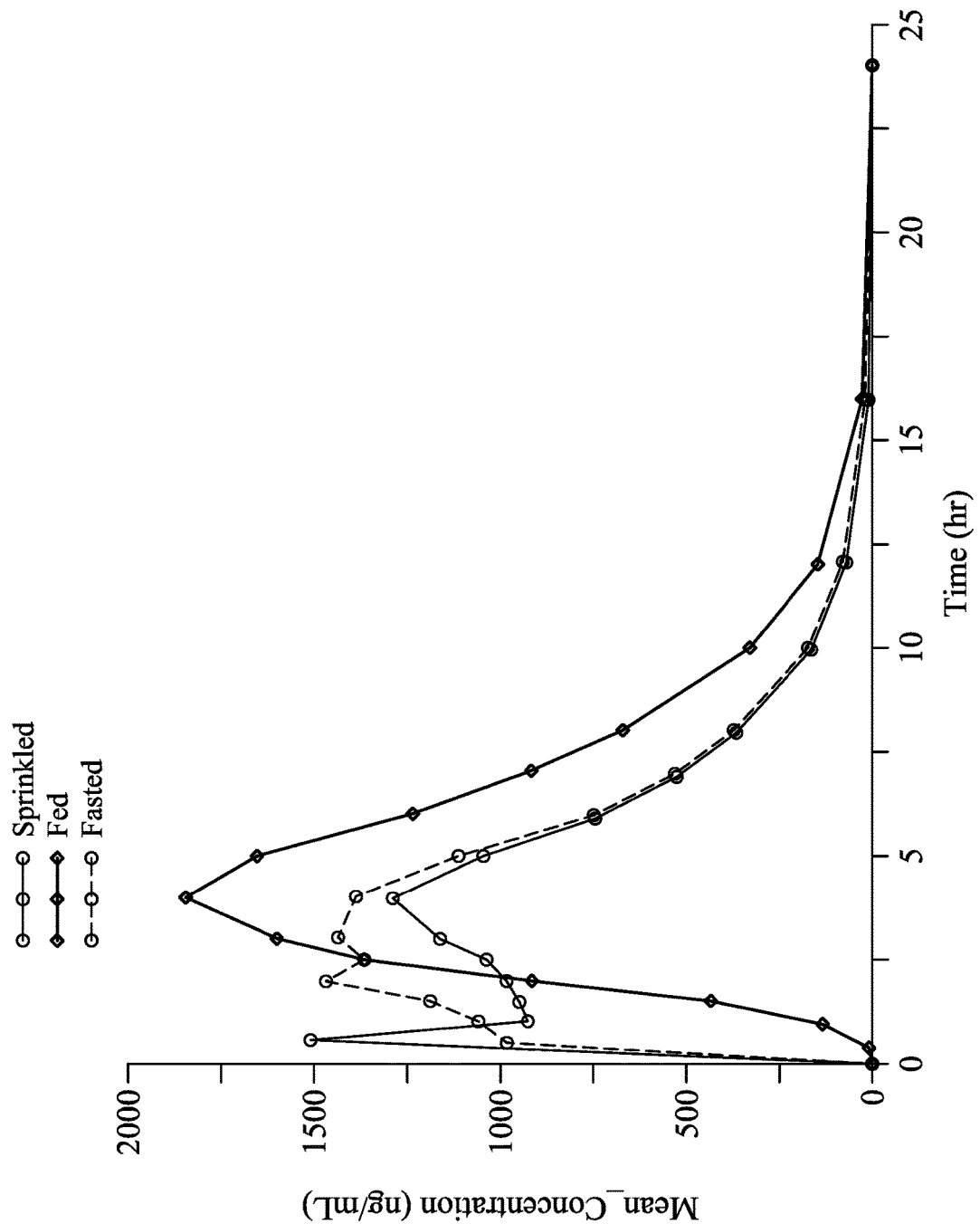
FIG. 20 shows the mean LD plasma concentration for the administrations described in Example 12.
Figure 21:
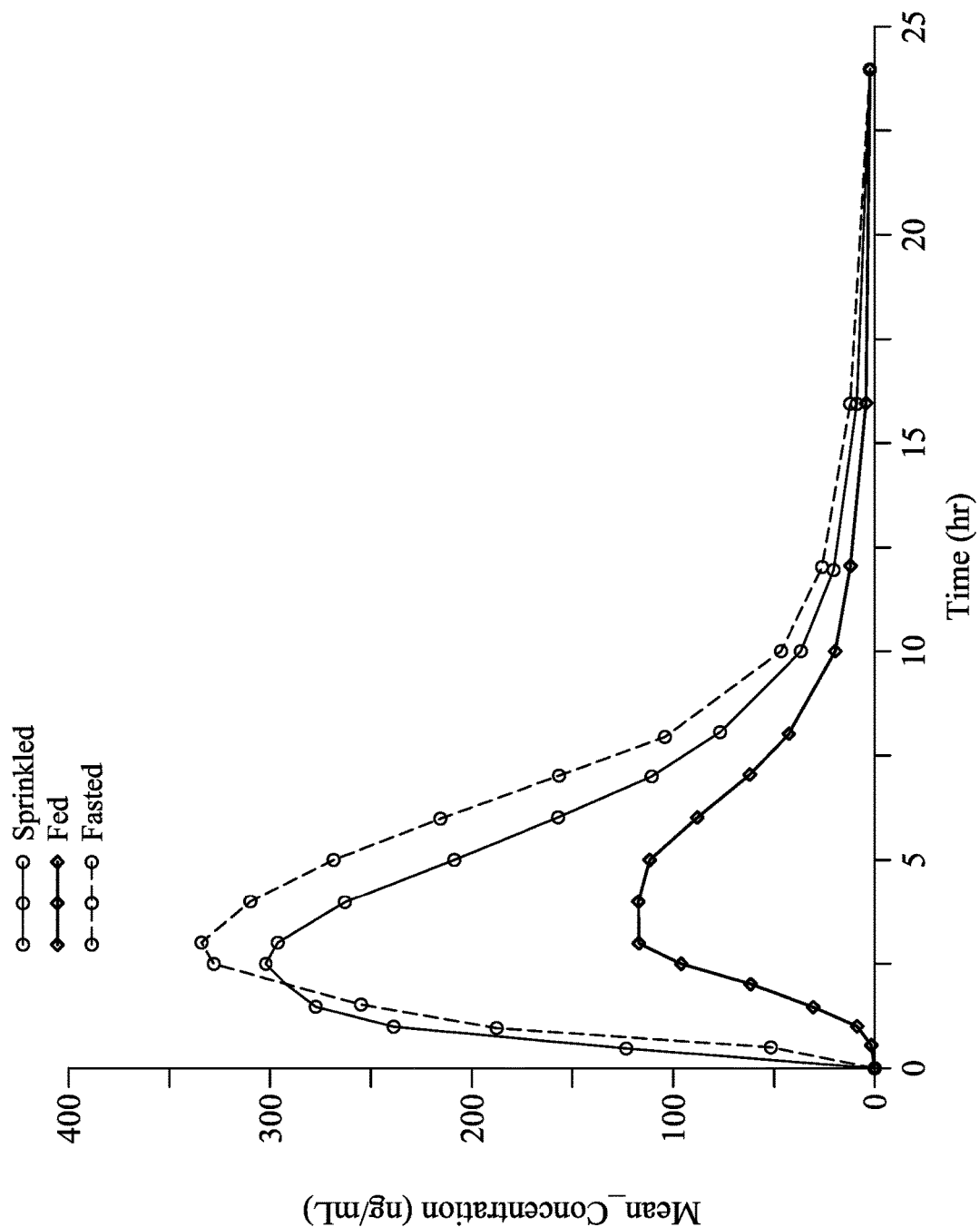
FIG. 21 shows the mean CD plasma concentration for the administrations described in Example 12.

Whole blood samples were taken prior to dosing and at 0.5, 1, 1.5, 2, 2.5, 3, 4, 5, 6, 7, 8, 10, 12, 16 and 24 hours post dose. The plasma samples were analyzed for concentrations of CD and LD by a validated liquid chromatography-tandem mass spectrometry (LC-MS/MS) method. Peak plasma ($C_{max}$), area under the plasma concentration-time curve ($AUC_t$ and $AUC_\infty$), and time to maximum concentration ($T_{max}$) for LD and CD were evaluated. The mean pharmacokinetic parameters are showing in the following table and in in FIGS. 20 and 21.

| Parameter | Fed | Sprinkled on Applesauce | Fasted |
| --- | --- | --- | --- |
| Levodopa | | | |
| $C_{max}$ (ng/mL) | 2185.6 ± 472.7 | 1634.2 ± 409.3 | 1826.9 ± 385.3 |
| $T_{max}$ (h) | 4.0 (2.0-5.0) | 0.5 (0.5-5.0) | 2.0 (0.5-5.0) |
| $AUC_{0-t}$ (ng · h/mL) | 10552.8 ± 1425.6 | 8330.9 ± 1965.0 | 9125.0 ± 2149.8 |
| $T_{1/2}$ (h) | 1.79 ± 0.3 | 2.02 ± 0.31 | 2.00 ± 0.30 |
| Carbidopa | | | |
| $C_{max}$ (ng/mL) | 140.8 ± 41.1 | 338.6 ± 91.8 | 403.6 ± 156.7 |
| $T_{max}$ (h) | 4.0 (2.0-6.0) | 2.5 (1.5-5.0) | 3.0 (1.0-6.0) |
| $AUC_{0-t}$ (ng · h/mL) | 751.0 ± 205.15 | 1909.2 ± 618.2 | 2175.0 ± 905.8 |
| $T_{1/2}$ (h) | 3.86 ± 0.78 | 3.95 ± 0.67 | 3.90 ± 0.56 |

All values in the above table are mean values ±SD except for $T_{max}$ which is reported as median (min-max) and the $AUC_{0-t}$ is the area under the concentration time curve from hour 0 to 24 hours.

After oral administration of the capsule in the fasted state, LD concentrations increased rapidly, reaching $T_{max}$ at a median of about 2 hours. The high-fat, high-calorie administration delayed LD median $T_{max}$ by about 2 hours, and increased LD $C_{max}$ and AUC by approximately 20% compared with the fasted state administration. The $C_{max}$ and $AUC_{0-t}$ values for CD were approximately 64% lower in the fed state versus the fasted state. Sprinkling the capsule content on applesauce did not substantially affect the pharmacokinetic parameters when compared with the administration in the fasted state.

Example 13

Based on the data in foregoing examples, including but not limited to Examples 11 and 12, the following is a recommended starting dose for converting a PD patient taking an oral immediate release CD-LD dosage form such as SINEMET© or a U.S FDA AB rated generic of SINEMET® to a starting dose of the capsules described in Example 7:

| Most Frequent IR CD-LD Unit Dose (mg) | Recommended Starting IPX203 Daily Dosing Regimen CD-LD (mg) |
| --- | --- |
| 25-100a | 70-280 mg (2 × 35-140 mg) |
| >25-100-37.5-150 | 105-420 mg (3 × 35-140 mg) |
| >37.5-150-50-200 | 140-560 mg (4 × 35-140 mg) |
| >50-200 | 175-700 mg (5 × 35-140 mg) |

Alternatively the starting daily doses of the IPX203 product as described in the above table may be administered by one or more dosage forms that comprise 35-140 mg CD-LD, 52.5-210 mg CD-LD, 70-280 mg CD-LD or 87.5-350 mg CD-LD.

PD patients who are on a total daily dose of less than 125-500 mg CD-LD from an oral IR CD-LD dosage form such as SINEMET® or a U.S. FDA AB rated generic version of SINEMET® can take one or more of the controlled release dosage forms described herein including those of Examples 1-7, preferably Example 7, or a U.S. FDA AB rated generic equivalent thereto every 12 hours. This dosing interval may be reduced to approximately every 8 hours if the subject does not achieve an acceptable duration effect.

PD patients who are newly diagnosed with PD or who are LD naïve can take one or more of the controlled release dosage forms described herein including those of Examples 1-7, preferably Example 7 or a U.S. FDA AB rated generic equivalent thereto every 12 hours. This dosing interval may be reduced to approximately every 8 hours if the subject does not achieve an acceptable duration effect.

PD patients taking a total daily dose of more than 125-500 mg CD-LD from an oral IR CD-LD dosage form such as SINEMET® or a U.S. FDA AB rated generic version of SINEMET® may take one or more of the controlled release dosage forms described herein, such as those of Examples 1-7 or an FDA AB rated generic equivalent thereto every 8 hours.

PD patients can take one or more of the controlled release dosage forms described herein including Examples 1-7 and preferably Example 7 or a U.S. FDA AB rated generic equivalent thereto every 12 hours or every six, seven or eight hours according to the dosing table of this example and exhibit:

(i) a total "Off" time during in a 24 hour period, i.e., a day, of less than 5 hours, less than 4 hours, less than 3 hours, less than 2 hours, less than 1 hour and less than 0.5 hours during the 24 hour period;

(ii) a total "Off" time during waking hours of less than 5 hours, less than 4 hours, less than 3 hours, less than 2 hours, less than 1 hour and less than 0.5 hours during waking hours in a 24 hour period;

(iii) a total "On" time of more than 5 hours, more than 6 hours, more than 7 hours, or 8 hours during the dosing time interval;

(iv) a total "Good On" time to more than 5 hours, more than 6 hours, more than 7 hours or 8 hours during the dosing time interval;

(v) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes or longer of a patient's "On" time per dose, per day and/or during waking hours per day compared to a comparable oral dose of an immediate release CD-LD dosage form or the total immediate release CD-LD doses per day or per waking hours;

(vi) an increase of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes or longer of a patient's "Good On" time per dose, per day and/or during waking hours per day compared to a comparable oral dose of an immediate release CD-LD dosage form or the total immediate release CD-LD doses per day or per waking hours;

(vii) a decrease of at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175 180 minutes or longer of a patient's "Off" time per dose, per day and/or during waking hours per day compared to a comparable oral dose of an immediate release CD-LD dosage form or the total immediate release CD-LD doses per day or per waking hours; or (viii) any combination of the foregoing.

With respect to forgoing increase of at least 30 to 180 minutes or longer of a patient's "On" or "Good On" time and decrease of a patient's "Off" time per dose, per day and/or during waking hours per day compared to a comparable oral dose of an immediate release CD-LD dosage form or the total immediate release CD-LD doses per day or per waking hours, it should be understood that the per day or waking hour comparison is based on the total amount of LD administered via the controlled release dosage form per day or waking hour period compared to the total amount of LD administered via the immediate release formulation per day or waking hours. This comparison may be the sum total of include 2, 3 or 4 controlled release administrations compared to the sum total of 4, 5 or 6 immediate release administrations during the day (24 hour period) or 12 to 18 hour waking period.

PD patients can take one or more of the controlled release dosage forms described herein including Examples 1-7, preferably Example 7, or a U.S. FDA AB rated generic equivalent thereto every 12 hours or every six, seven or eight hours according to the dosing table of this example and exhibit a substantial reduction in total "Off" time during waking hours. The reduction in total "Off" time should be at least a 5%, 10%, 15%, 20%, 25%, 30%, 35%, 40% or 50% reduction in the total "Off" time during waking hours such as 16 hours in a 24 hour period compared to treatment with an immediate release CD-LD oral dosage form such as SINEMET® or a U.S. FDA AB rated generic version of SINEMET®.

PD patients can take one or more of the controlled release dosage forms described herein including Examples 1-7, preferably Example 7, or a U.S. FDA AB rated generic equivalent thereto every 12 hours or every six, seven or eight hours according to the dosing table of this example and exhibit a total "Off" time during the dosing interval of 180 minutes or less, 160 minutes or less, 140 minutes or less, 120 minutes or less, 100 minutes or less, 90 minutes or less, 75 minutes or less, 60 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less or 0 minutes. For the PD patients in the twice a day dosing group the dosing interval is about every 12 hours. For the PD patients in the three times a day dosing group the dosing interval is about 8 hours. For the PD patients in a four times a day dosing group the dosing interval is about 6 hours.

PD patients being administered the controlled release dosage form as described herein including Examples 1-7, preferably Example 7, or a U.S. FDA AB rated generic equivalent thereto every 12 hours or every six, seven or eight hours and according to the dosing table of this example do not require an increase in the LD amounts administered in the morning or first daily dose upon waking. Rather the PD patients may take the same dose at each dosing time throughout the day thereby avoiding the need for different, morning, afternoon and/or evening doses which may complicate the dosing regimen, confuse the caregiver or PD patient and result in over or under dosing. Moreover, these PD patients being administered the controlled release dosage form as described herein and according to the dosing table of this example on a schedule that allows dosing about 30 minutes or less before bedtime, allows the PD patient to experience an improved night sleep and wake in the morning in an "On" or "Good On" state and thereby eliminate the need for a rescue dose of LD. These PD patients being administered the controlled release dosage form as described herein and according to the dosing table of this example on a schedule that allows dosing about 30 minutes or less before bedtime, further allows the PD patient to experience a quicker time to an "On" or "Good On" state following the first morning dose of the controlled release dosage form compared to treatment with an immediate release CD-LD oral dosage form such as SINEMET® or a U.S. FDA AB rated generic version of SINEMET®. The quicker time to an On" or "Good On" state following the first morning dose of the controlled release dosage form can range from about 5, 6, 7, 8, 9, 10, 11, 12, 13, 14, 15, 16, 17, 18, 19, Or 20 minutes faster compared to the treatment with an immediate release CD-LD oral dosage form such as SINEMET® or a U.S. FDA AB rated generic version of SINEMET®.

PD patients can take one or more of the controlled release dosage forms described herein including Examples 1-7, preferably Example 7, or a U.S. FDA AB rated generic equivalent thereto every 12 hours or every six, seven or eight hours according to the dosing table of this example and exhibit a substantial improvement in their PGI-C or CGI-C scores, i.e. report a value of "much improved" or "very much improved" compared to treatment with an immediate release CD-LD oral dosage form such as SINEMET® or a U.S. FDA AB rated generic version of SINEMET®.

PD patients can take one or more of the controlled release dosage forms described herein including Examples 1-7, preferably Example 7, or a U.S. FDA AB rated generic equivalent thereto every 12 hours or every six, seven or eight hours according to the dosing table of this example and exhibit an improved emotional well-being as determined by PDQ-39 compared to treatment with an immediate release CD-LD oral dosage form such as SINEMET© or a U.S. FDA AB rated generic version of SINEMET®.

PD patients can take one or more of the controlled release dosage forms described herein including Examples 1-7, preferably Example 7, or a U.S. FDA AB rated generic equivalent thereto every 12 hours or every six, seven or eight hours according to the dosing table of this example and exhibit a decrease in perceptual problems and or hallucinations as determined by the NMSS score compared to treatment with an immediate release CD-LD oral dosage form such as SINEMET® or a U.S. FDA AB rated generic version of SINEMET®.

PD patients may take the controlled release dosage form as described herein including Examples 1-7, preferably Example 7, or a U.S. FDA AB rated generic equivalent thereto with or without food and if taken with food will exhibit at least a 10%, 11%, 12%, 13%, 14%, 15%, 16%, 17%, 18% 19%, 20%, 21%, 22%, 23%, 24% or 25% or greater increase in LD $C_{max}$ and/or LD AUC values when compared to the administration after at least ten hours of fasting, preferably after 10 hours of overnight fasting. The increase in LD $C_{max}$ and/or LD AUC when administered with food compared to administration after fasting may be determined using the conditions outlined in Example 12 above. In another embodiment, oral administration of the controlled release dosage form in fed state, e.g., after a high-fat, high-calorie meal, may increase $C_{max}$ approximately 19% and $AUC_{0-\infty}$ approximately 18% for LD compared to administration in fasted state. There may be a delay of approximately 2 hours in the absorption of LD when the controlled release dosage form is taken with a high-fat, high calorie meal. In addition, absorption of LD may be decreased by a high protein meal.

PD patients may further take the controlled release dosage form as described herein including Examples 1-7, preferably Example 7, or a U.S. FDA AB rated generic equivalent thereto with or without food and if taken with food will exhibit a change (i.e. ±) in LD $T_{max}$ and/or CD $T_{max}$ of less than 5 hour, less than 4.5 hours, less than 4.0 hours, less than 3.5 hours, less than 3.0 hours, less than 2.5 hours, less than 2.0 hours, less than 1.5 hours, less than 1.0 hours or less than 0.5 hours when compared to the administration after at least ten hours of fasting, preferably after 10 hours of overnight fasting. The change in LD $T_{max}$ and/or CD $T_{max}$ when administered with food compared to administration after fasting may be determined using the conditions outlined in Example 12 above. The change in $T_{max}$ is preferably an increase time to $T_{max}$ under fed conditions of less than 5 hour, less than 4.5 hours, less than 4.0 hours, less than 3.5 hours, less than 3.0 hours, less than 2.5 hours, less than 2.0 hours, less than 1.5 hours, less than 1.0 hours or less than 0.5 hours compared to the administration after fasting.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating a levodopa naïve patient with Parkinson's disease comprising an oral administration of a multiparticulate controlled release levodopa dosage form comprising:
    a) a controlled release component comprising a plurality of beads that pass through a 12 mesh screen but are retained on a 24 mesh screen wherein the beads are substantially free of carbidopa, free of a catechol-O-methyl transferase inhibitor and comprise: (i) a core comprising levodopa, (ii) a controlled release coating surrounding the core, (iii) a coating comprising a muco-adhesive polymer surrounding the controlled release coating and (iv) a coating comprising an enteric coating polymer surrounding the coating comprising the muco-adhesive polymer; and
    (b) an immediate release component comprising levodopa and carbidopa;
wherein the controlled release dosage form is administered twice a day with each dose administered each time comprising 140 mg of levodopa and a total daily administered levodopa dose of 280 mg;
wherein the patient is not being treated with a catechol-O-methyl transferase inhibitor and the patient has not been previously treated with levodopa; and
wherein twice a day dosing improves the patient's motor state by about 10% to 50% as determined by patient's Parkinson's disease diary.

2. The method of claim 1, wherein the immediate release component comprises from about 80% to about 100% of the total amount of carbidopa in the multiparticulate controlled release formulation.

3. The method of claim 2, wherein the multiparticulate controlled release dosage form when tested using a USP Apparatus I at 75 rpms and 37°±0.5° C. with 500-900 ml of simulated gastric fluid for 2 hours and pH 6.8 phosphate buffer thereafter exhibits the following levodopa release profile:
   20% to 60% of levodopa is released after 2 hours;
   40% to 80% of levodopa is released after 3 hours;
   60% to 100% of levodopa is released after 4 hours; and
   not less than 80% is released after 7 hours,
wherein the simulated gastric fluid has a pH of about 1 to about 4.

4. The method of claim 2, wherein the controlled release coating comprises a controlled release material selected from the group consisting of ethyl cellulose, cellulose acetate, and mixtures thereof.

5. The method of claim 2, wherein the mucoadhesive polymer is capable of forming a positive ionic charge at pHs present in the human gastrointestinal tract.

6. The method of claim 5, wherein the mucoadhesive polymer is an amino methacrylate copolymer.

7. The method of claim 6, wherein the amino methacrylate copolymer is poly(butyl methacrylate-co-(2-dimethylaminoethyl)methacrylate-co-methylmethacrylate).

8. The method of claim 2, wherein after administration the controlled release dosage form provides a levodopa plasma level of at least about 300 ng/mL within about 1 hour after administration and after twice a day administration of the controlled release dosage form for at least 7 days provides a minimum levodopa plasma level at least about 250 ng/mL at about six hours after dosing.

9. The method of claim 2, wherein after administration of the controlled release dosage form twice a day for at least 7 days, the minimum carbidopa plasma level is at least about 40 ng/mL seven to eight hours after dosing.

10. The method of claim 2, wherein the patient is newly diagnosed with Parkinson's disease.

11. The method of claim 2, wherein the Parkinson's disease is primary parkinsonism, postencephalitic parkinsonism, parkinsonism following carbon monoxide intoxication, or parkinsonism following manganese intoxication.

12. A method for treating a levodopa naïve patient with Parkinson's disease comprising an oral administration of a multiparticulate controlled release levodopa dosage form comprising:
  a) a controlled release component comprising a plurality of beads that pass through a 12 mesh screen but are retained on a 24 mesh screen wherein the beads are substantially free of carbidopa, free of a catechol-O-methyl transferase inhibitor and comprise: (i) a core comprising levodopa, (ii) a controlled release coating surrounding the core, (iii) a coating comprising a muco-adhesive polymer surrounding the controlled release coating, and (iv) a coating comprising an enteric coating polymer surrounding the coating comprising the muco-adhesive polymer; and
  (b) an immediate release component comprising levodopa and carbidopa;
wherein the controlled release dosage form is administered twice a day with each dose administered each time comprising 140 mg of levodopa and a total daily administered levodopa dose of 280 mg;
wherein the patient is not being treated with a catechol-O-methyl transferase inhibitor and the patient has not been previously treated with levodopa; and
wherein the twice a day dosing provides a reduction of from about 10%-40% in the patient's tremor, dyskinesia, and/or mobility.

13. The method of claim 12, wherein the immediate release component comprises from about 80% to about 100% of the total amount of carbidopa in the multiparticulate controlled release formulation.

14. The method of claim 13, wherein the multiparticulate controlled release dosage form when tested using a USP Apparatus I at 75 rpms and 37°±0.5° C. with 500-900 ml of simulated gastric fluid for 2 hours and pH 6.8 phosphate buffer thereafter exhibits the following levodopa release profile:

20% to 60% of levodopa is released after 2 hours;
40% to 80% of levodopa is released after 3 hours;
60% to 100% of levodopa is released after 4 hours; and
not less than 80% is released after 7 hours,
wherein the simulated gastric fluid has a pH of about 1 to about 4.

15. The method of claim 13, wherein the controlled release coating comprises a controlled release material selected from the group consisting of ethyl cellulose, cellulose acetate, and mixtures thereof.

16. The method of claim 13, wherein the mucoadhesive polymer is capable of forming a positive ionic charge at pHs present in the human gastrointestinal tract.

17. The method of claim 16, wherein the mucoadhesive polymer is an amino methacrylate copolymer.

18. The method of claim 17, wherein the amino methacrylate copolymer is poly(butyl methacrylate-co-(2-dimethylaminoethyl)methacrylate-co-methylmethacrylate).

19. The method of claim 13, wherein after administration the controlled release dosage form provides a levodopa plasma level of at least about 300 ng/mL within about 1 hour after administration and after twice a day administration of the controlled release dosage form for at least 7 days provides a minimum levodopa plasma level at least about 250 ng/mL at about six hours after dosing.

20. The method of claim 13, wherein after administration of the controlled release dosage form twice a day for at least 7 days, the minimum carbidopa plasma level is at least about 40 ng/mL seven to eight hours after dosing.

21. The method of claim 13, wherein the patient is newly diagnosed with Parkinson's disease.

22. The method of claim 13, wherein the Parkinson's disease is primary parkinsonism, postencephalitic parkinsonism, parkinsonism following carbon monoxide intoxication, or parkinsonism following manganese intoxication.

23. A method for treating a levodopa naïve patient with Parkinson's disease comprising an oral administration of a multiparticulate controlled release levodopa dosage form comprising:
  a) a controlled release component comprising a plurality of beads that pass through a 12 mesh screen but are retained on a 24 mesh screen wherein the beads are substantially free of carbidopa, free of a catechol-O-methyl transferase inhibitor and comprise: (i) a core comprising levodopa, (ii) a controlled release coating surrounding the core, (iii) a coating comprising a muco-adhesive polymer surrounding the controlled release coating, and (iv) a coating comprising an enteric coating polymer surrounding the coating comprising the muco-adhesive polymer; and
  (b) an immediate release component comprising levodopa and carbidopa; wherein the controlled release dosage form is administered twice a day with each dose administered each time comprising 140 mg of levodopa and a total daily administered levodopa dose of 280 mg;
wherein the patient is not being treated with a catechol-O-methyl transferase inhibitor and the patient has not been previously treated with levodopa; and
wherein the twice a day dosing reduces the patient's Movement Disorders Society version of the Unified Parkinson's Disease Rating Scale (MDS-UPDRS) scores by at least 3 points.

24. The method of claim 23, wherein the twice a day dosing reduces the patient's MDS-UPDRS scores from about 3 points to about 15 points.

25. The method of claim 23, wherein the immediate release component comprises from about 80% to about 100% of the total amount of carbidopa in the multiparticulate controlled release formulation.

26. The method of claim 25, wherein the multiparticulate controlled release dosage form when tested using a USP Apparatus I at 75 rpms and 37°±0.5° C. with 500-900 ml of simulated gastric fluid for 2 hours and pH 6.8 phosphate buffer thereafter exhibits the following levodopa release profile:

20% to 60% of levodopa is released after 2 hours;
40% to 80% of levodopa is released after 3 hours;
60% to 100% of levodopa is released after 4 hours; and
not less than 80% is released after 7 hours, wherein the simulated gastric fluid has a pH of about 1 to about 4.

27. The method of claim 25, wherein the controlled release coating comprises a controlled release material selected from the group consisting of ethyl cellulose, cellulose acetate, and mixtures thereof.

28. The method of claim 25, wherein the mucoadhesive polymer is capable of forming a positive ionic charge at pHs present in the human gastrointestinal tract.

29. The method of claim 28, wherein the mucoadhesive polymer is an amino methacrylate copolymer.

30. The method of claim 29, wherein the amino methacrylate copolymer is poly(butyl methacrylate-co-(2-dimethylaminoethyl)methacrylate-co-methylmethacrylate).

31. The method of claim 25, wherein the patient is newly diagnosed with Parkinson's disease.

32. The method of claim 25, wherein the Parkinson's disease is primary parkinsonism, postencephalitic parkinsonism, parkinsonism following carbon monoxide intoxication, or parkinsonism following manganese intoxication.

\* \* \* \* \*